| (12) | United States Patent | (10) Patent No.: | US 9,597,106 B2 |
|---|---|---|---|
| | Tsubuku | (45) Date of Patent: | Mar. 21, 2017 |

(54) ULTRASONIC TREATMENT APPARATUS

(71) Applicant: OLYMPUS CORPORATION, Hachioji-shi, Tokyo (JP)

(72) Inventor: Yoshihiro Tsubuku, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/156,969

(22) Filed: May 17, 2016

(65) Prior Publication Data

US 2016/0256190 A1 Sep. 8, 2016

Related U.S. Application Data

(63) Continuation of application No. PCT/JP2015/052868, filed on Feb. 2, 2015.

(30) Foreign Application Priority Data

Feb. 17, 2014 (JP) .................................. 2014-027990

(51) Int. Cl.

| B60B 1/06 | (2006.01) |
|---|---|
| H01L 41/04 | (2006.01) |
| A61B 17/32 | (2006.01) |
| B06B 1/06 | (2006.01) |
| A61B 17/00 | (2006.01) |

(Continued)

(52) U.S. Cl.
CPC ........ *A61B 17/320092* (2013.01); *B06B 1/06* (2013.01); *H01L 41/042* (2013.01); *A61B 2017/0003* (2013.01); *A61B 2017/00026* (2013.01); *A61B 2017/2825* (2013.01); *A61B 2018/00875* (2013.01)

(58) Field of Classification Search
CPC .. A61B 17/320092; H01L 41/042; B06B 1/06
USPC .................. 310/317, 322, 334; 600/437, 439
See application file for complete search history.

(56) References Cited

U.S. PATENT DOCUMENTS

2004/0176717 A1 9/2004 Honda et al.
2009/0254080 A1 10/2009 Honda
(Continued)

FOREIGN PATENT DOCUMENTS

JP 2002-119518 A 4/2002
JP 2004-267462 A 9/2004
(Continued)

OTHER PUBLICATIONS

Mar. 17, 2015 Search Report issued in International Patent Application No. PCT/JP2015/052868.

*Primary Examiner* — Derek Rosenau
(74) *Attorney, Agent, or Firm* — Oliff PLC

(57) ABSTRACT

An ultrasonic treatment apparatus includes an impedance detecting section detecting an ultrasonic impedance value with time, and a gradual decrease detecting section detecting a gradual decrease start point to start gradual decrease of the ultrasonic impedance value. The ultrasonic treatment apparatus includes a tentative peak value holding section holding the ultrasonic impedance value at the detected gradual decrease start point as a tentative peak value, and a peak judging section judging whether the held tentative peak value is a target peak by comparing, relative to the held tentative peak value, changes with time of the ultrasonic impedance value after the gradual decrease start point.

30 Claims, 31 Drawing Sheets

(51) Int. Cl.
   *A61B 18/00*          (2006.01)
   *A61B 17/28*          (2006.01)

(56)          References Cited

U.S. PATENT DOCUMENTS

| | | | |
|---|---|---|---|
| 2009/0259221 | A1 | 10/2009 | Tahara et al. |
| 2010/0179423 | A1* | 7/2010 | Ramstein ........... A61B 5/02007 |
| | | | 600/437 |
| 2011/0290853 | A1* | 12/2011 | Shelton, IV ..... A61B 17/07207 |
| | | | 227/177.1 |
| 2012/0310264 | A1 | 12/2012 | Messerly et al. |
| 2013/0030328 | A1 | 1/2013 | Dycus et al. |
| 2013/0066238 | A1 | 3/2013 | Irisawa et al. |

FOREIGN PATENT DOCUMENTS

| | | |
|---|---|---|
| JP | 2009-247887 A | 10/2009 |
| JP | 2009-254818 | 11/2009 |
| JP | 6259883 B2 | 8/2013 |
| JP | 2013-541987 A | 11/2013 |
| WO | 2012/044600 A2 | 4/2012 |
| WO | 2012/108295 A1 | 8/2012 |
| WO | 2014/125983 A1 | 8/2014 |

* cited by examiner

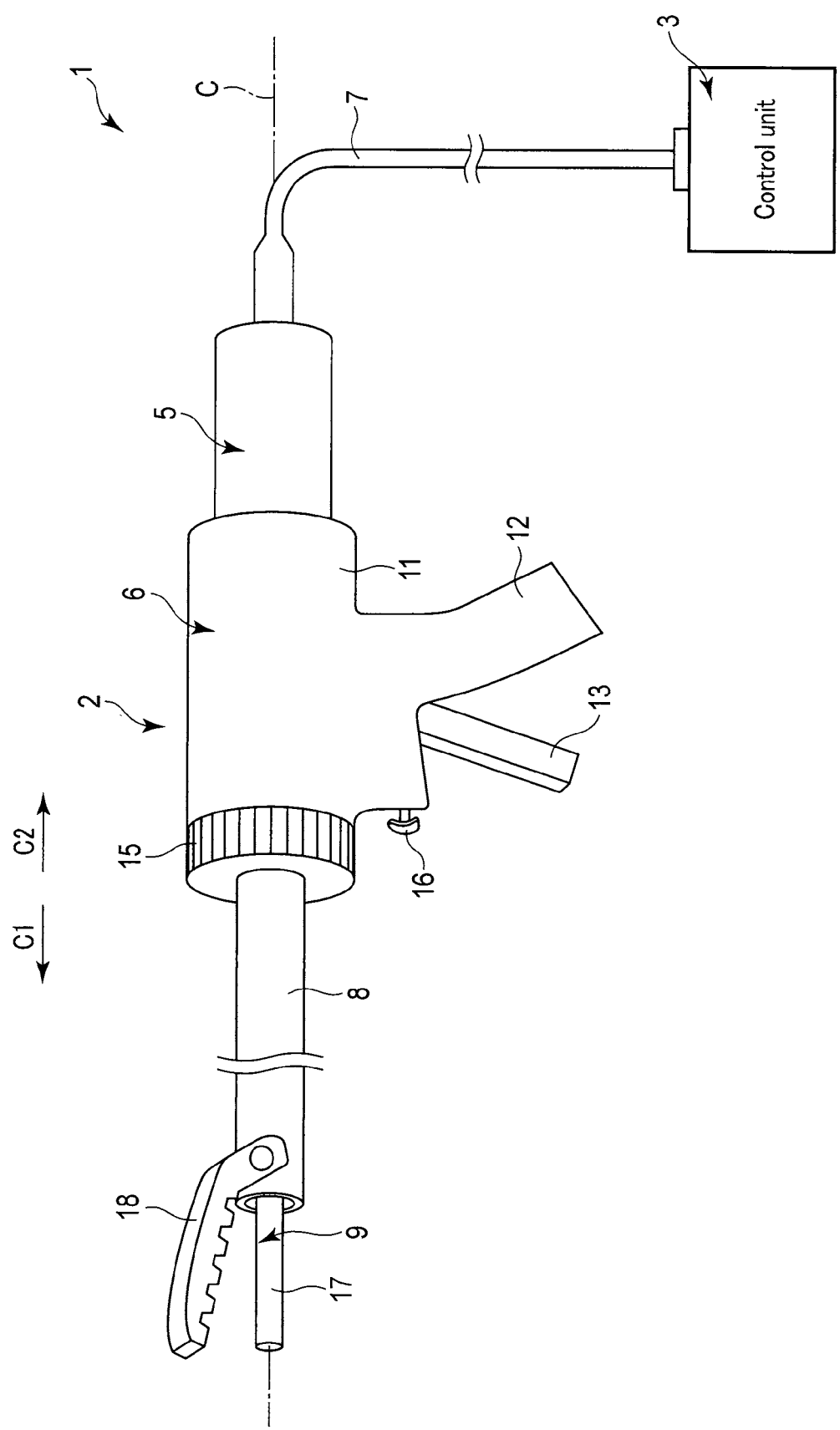
F I G. 1

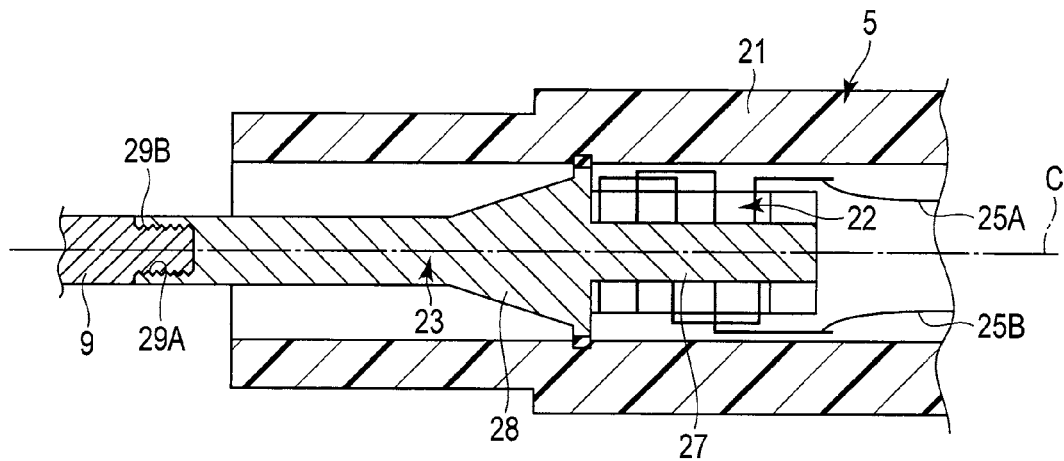
F I G. 2
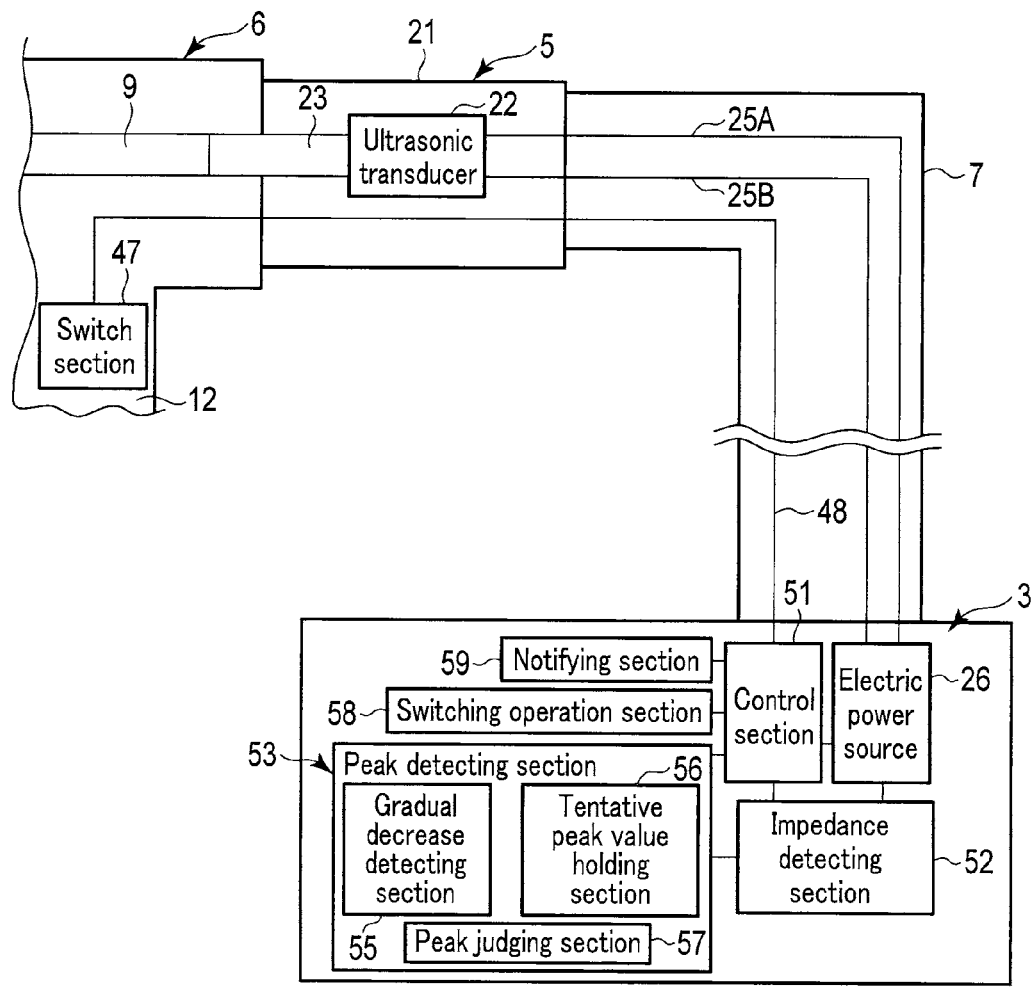
F I G. 3

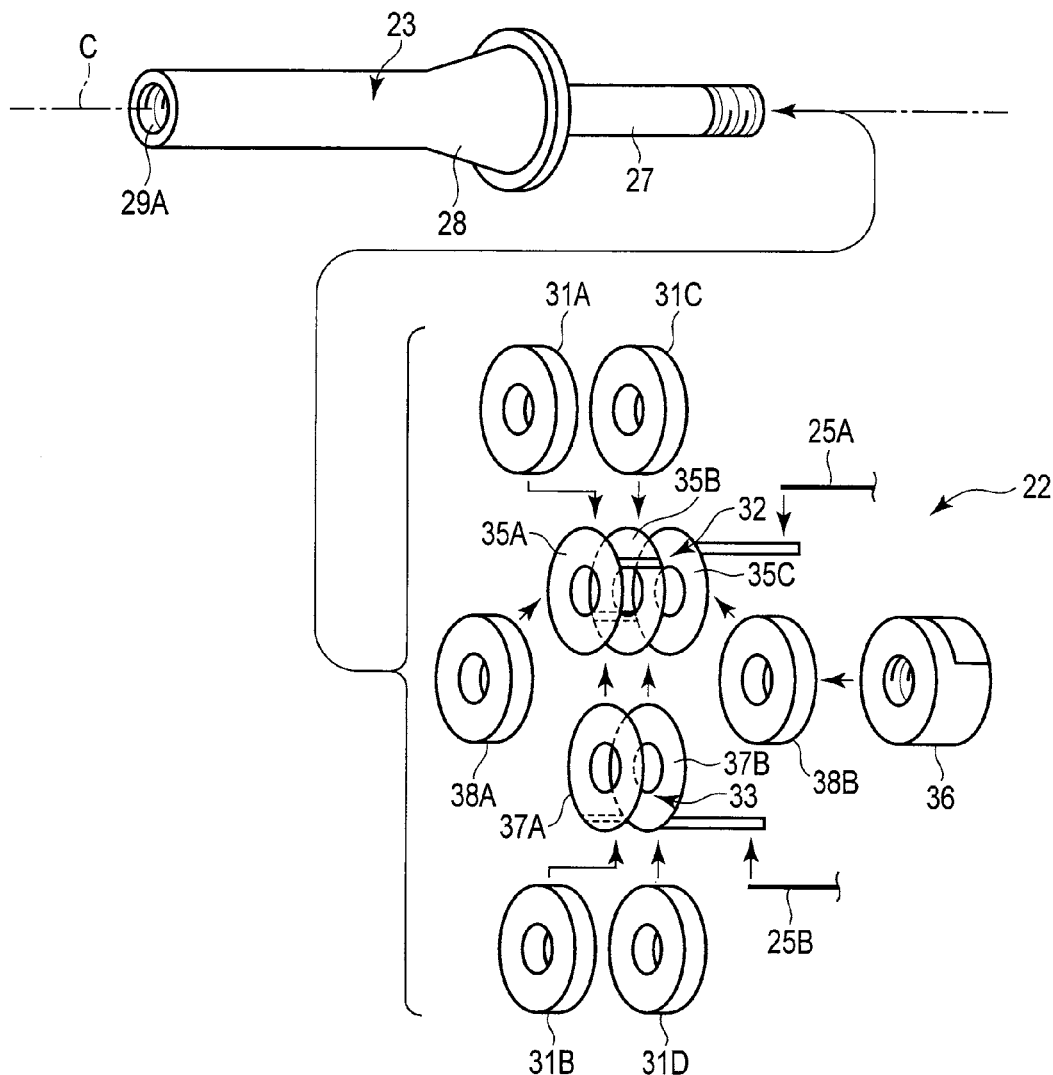
F I G. 4
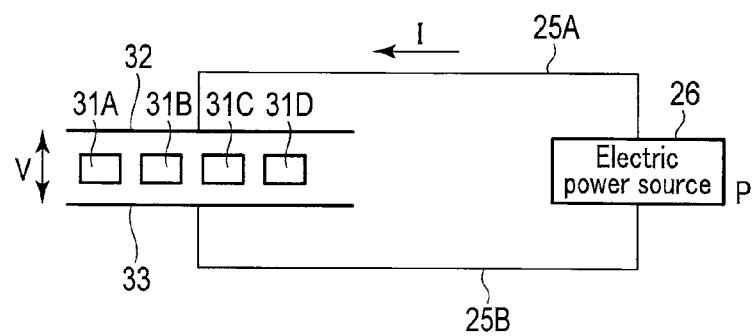
F I G. 5

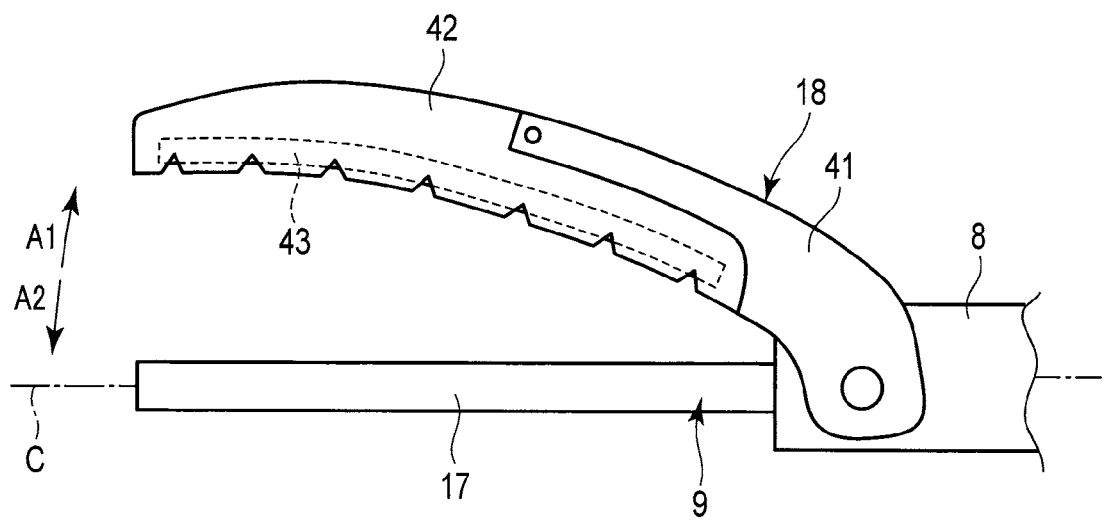
F I G. 6
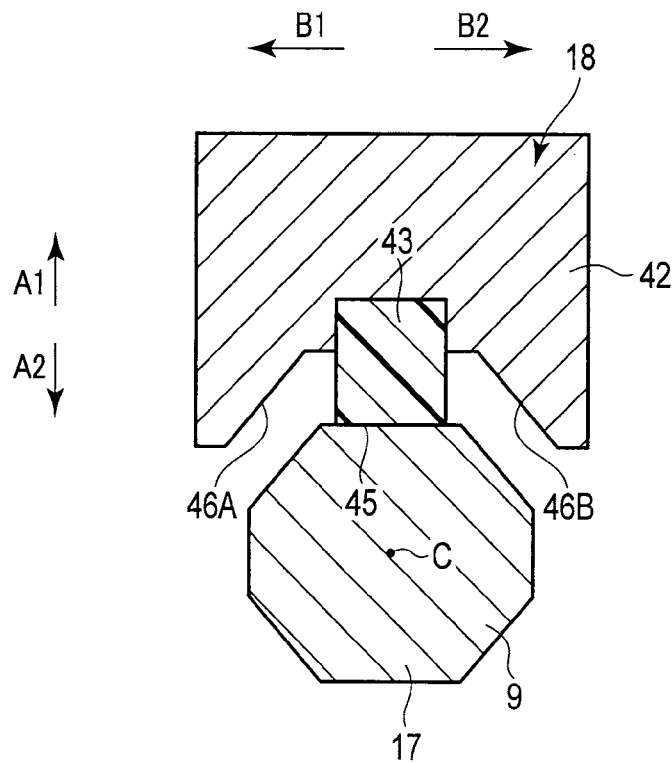
F I G. 7

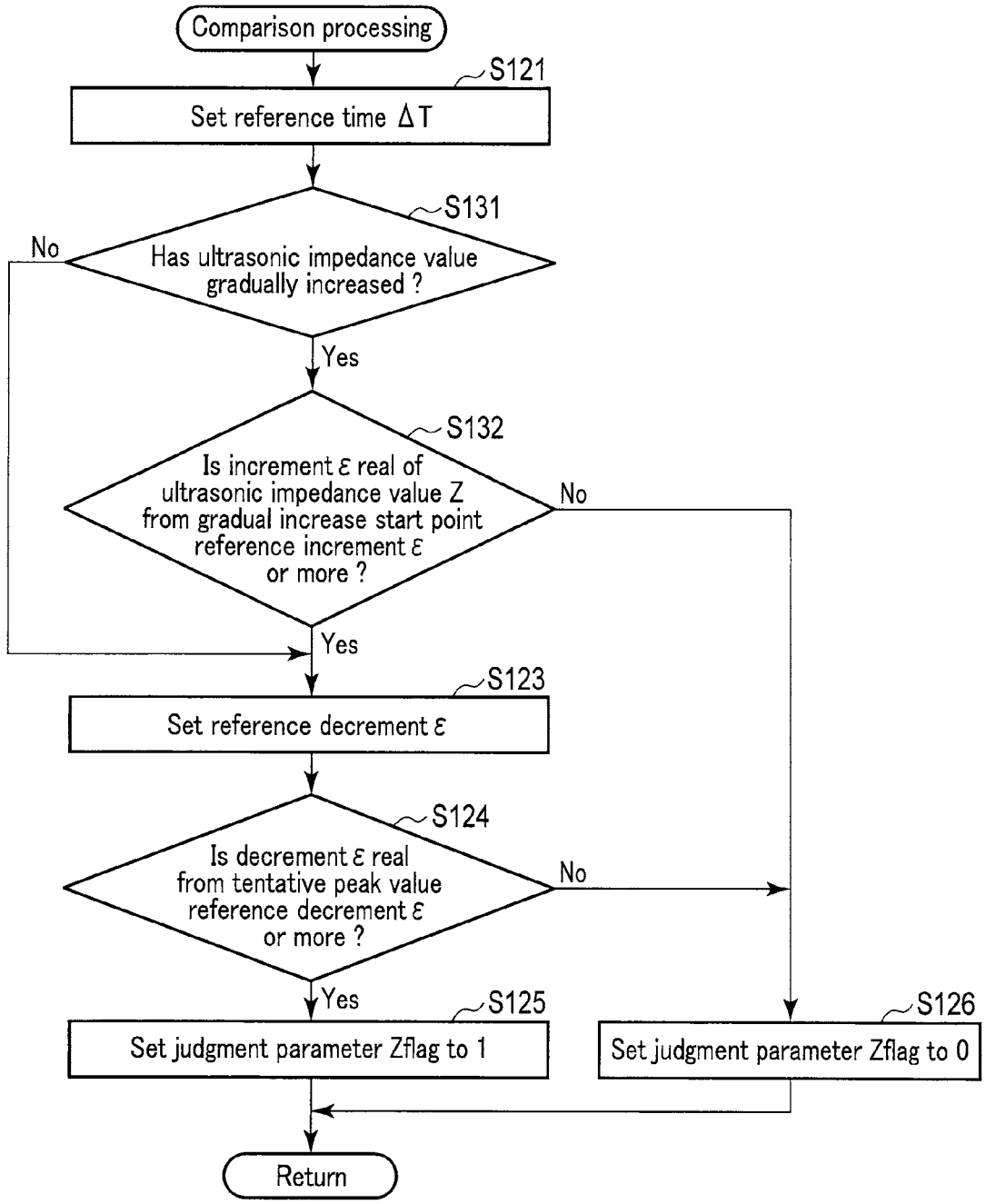
F I G. 15

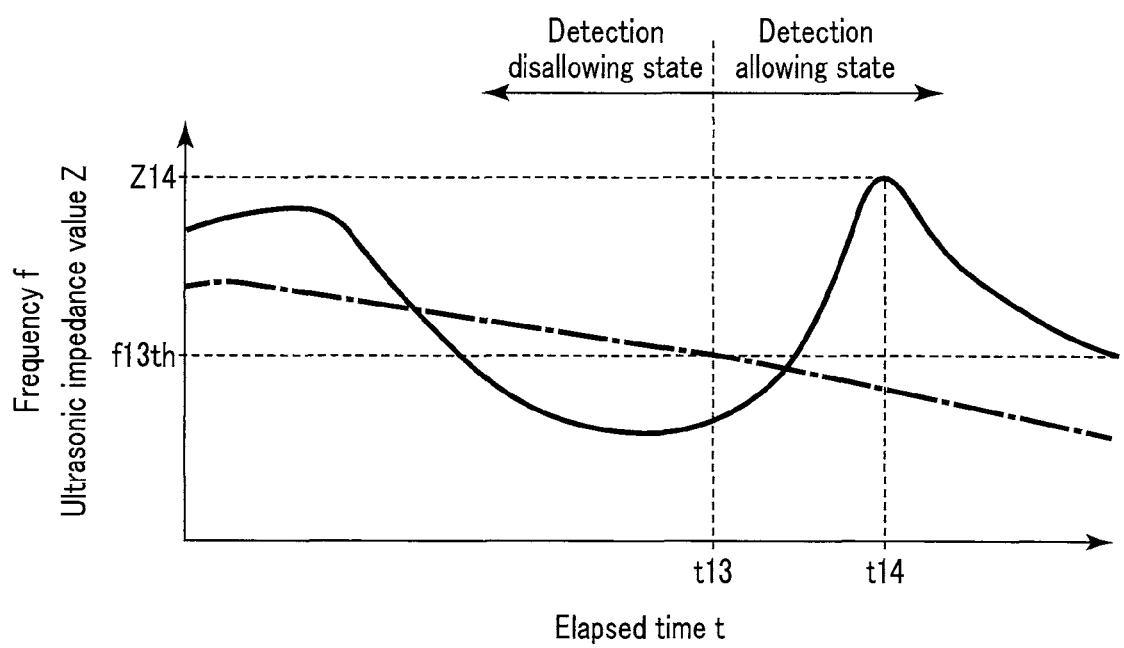
F I G. 25

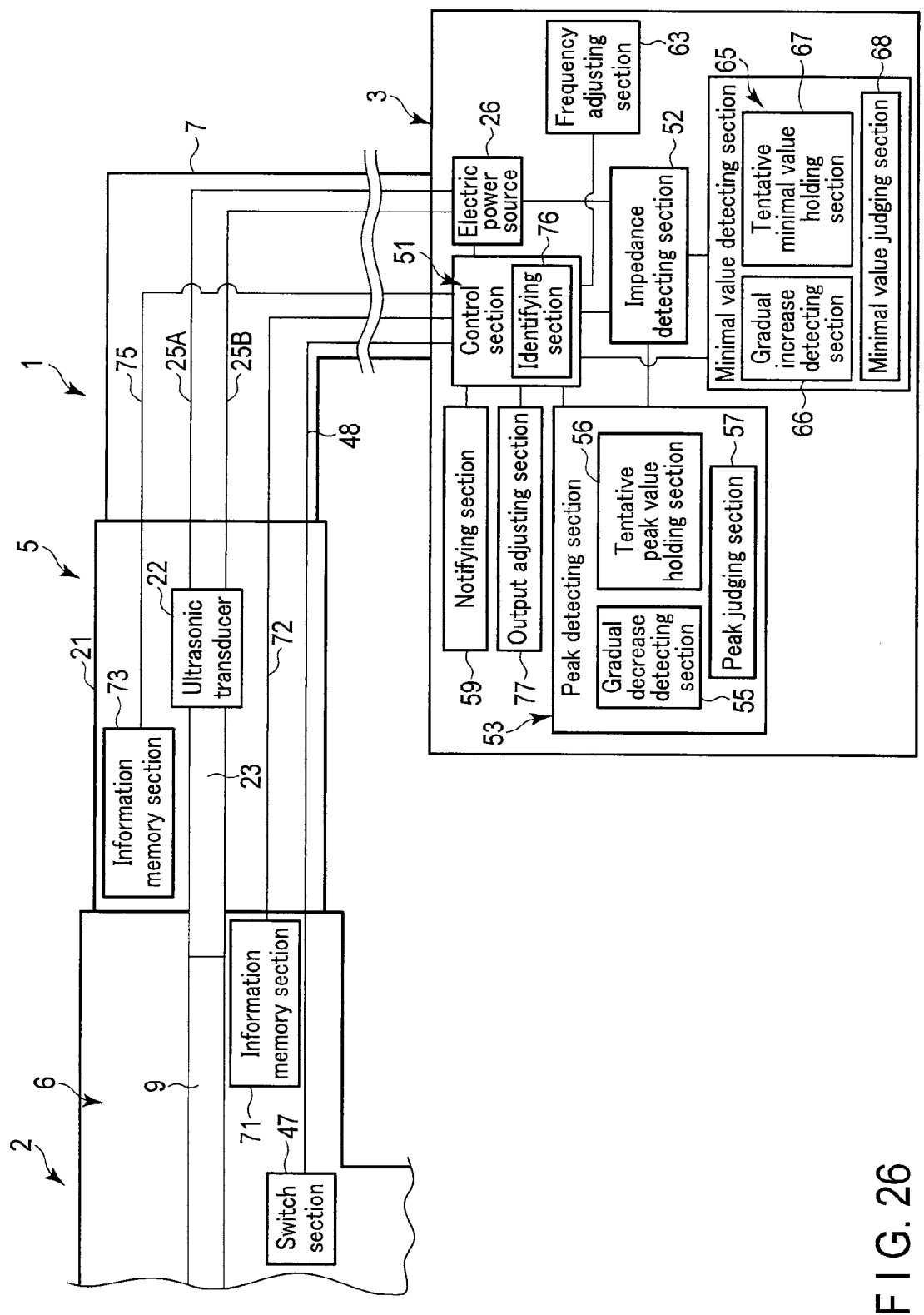
F I G. 26

| Output level 1 | Type of ultrasonic treatment instrument 2 (ultrasonic probe 9) | | | |
|---|---|---|---|---|
| | Type K1 | Type K2 | Type K3 | Without information memory section 73 |
| Type of ultrasonic transducer 22 — Type J1 | Set value L1 | Set value L2 | Set value L3 | Set value L4 |
| Type J2 | Set value L5 | Set value L6 | Set value L7 | Set value L8 |
| Type J3 | Set value L9 | Set value L10 | Set value L11 | Set value L12 |
| Without information memory section 71 | Set value L13 | Set value L14 | Set value L15 | Set value L16 |

F I G. 28

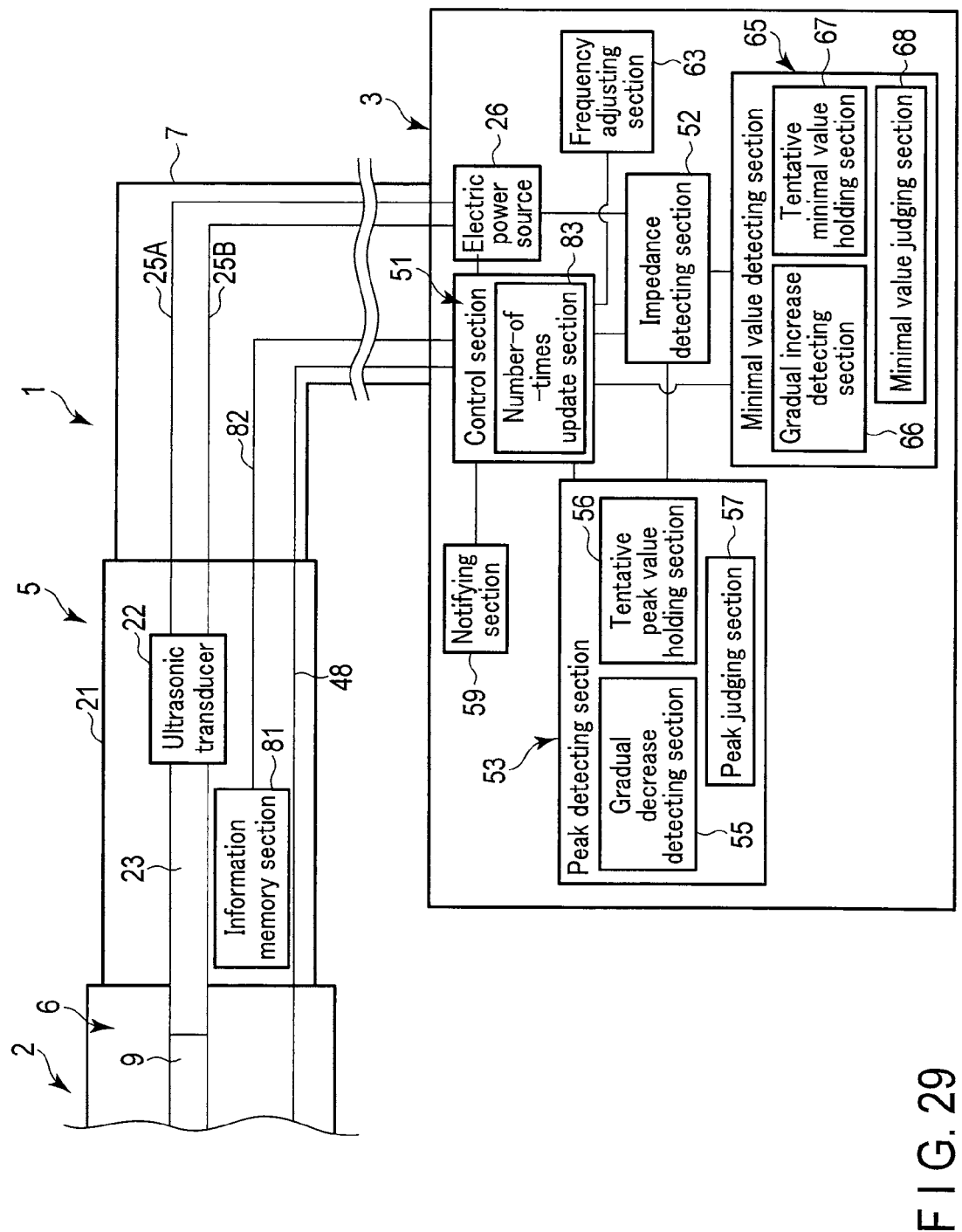
F I G. 29

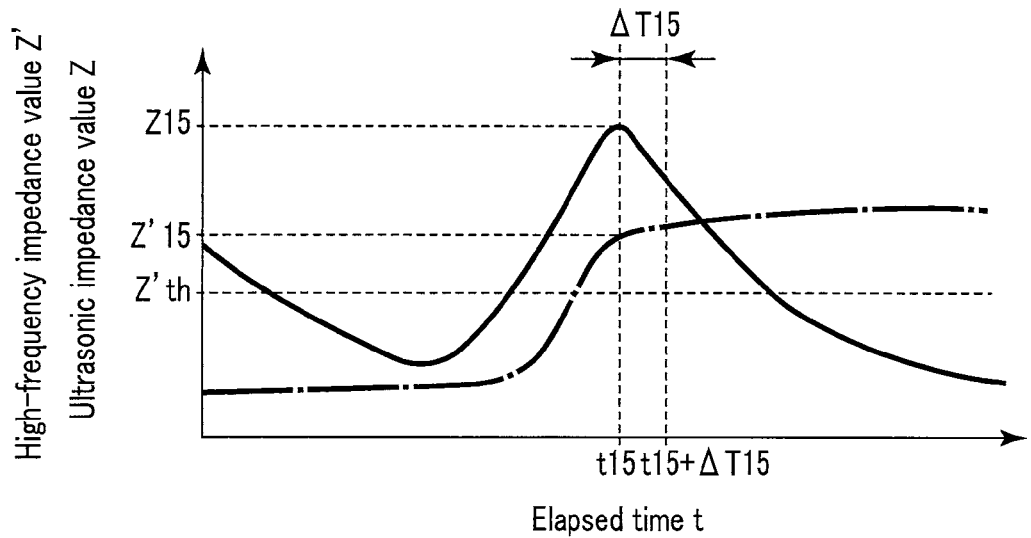
F I G. 34
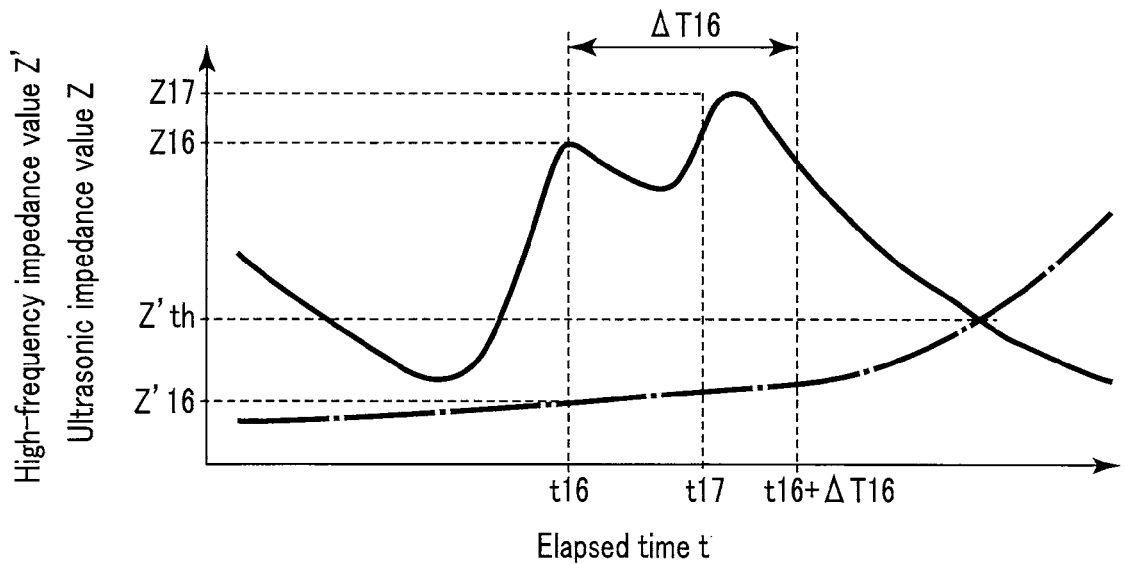
F I G. 35

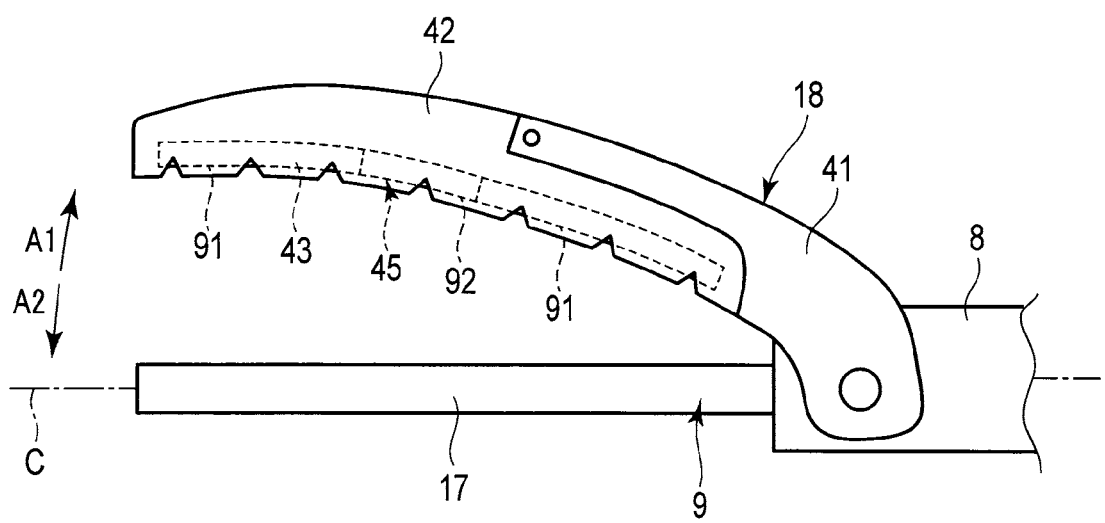
F I G. 36
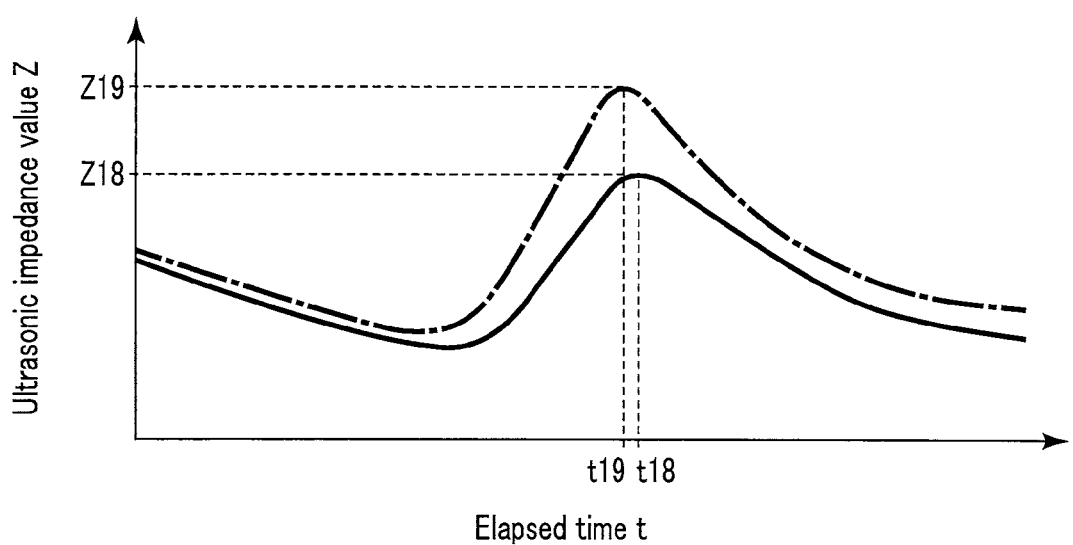
F I G. 37

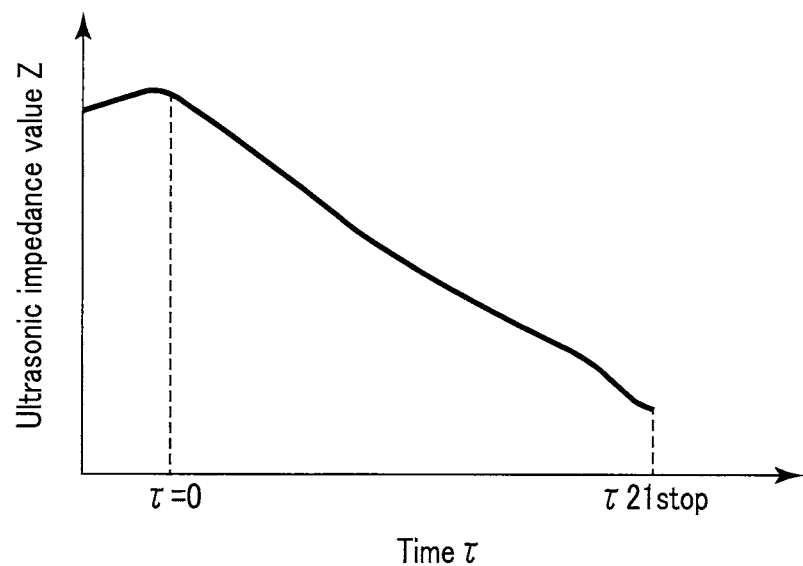
F I G. 42
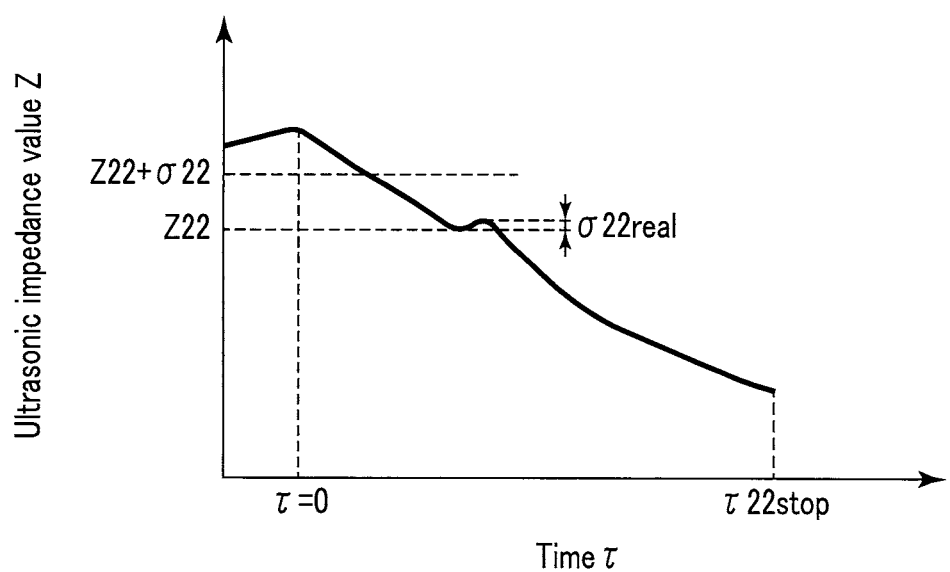
F I G. 43

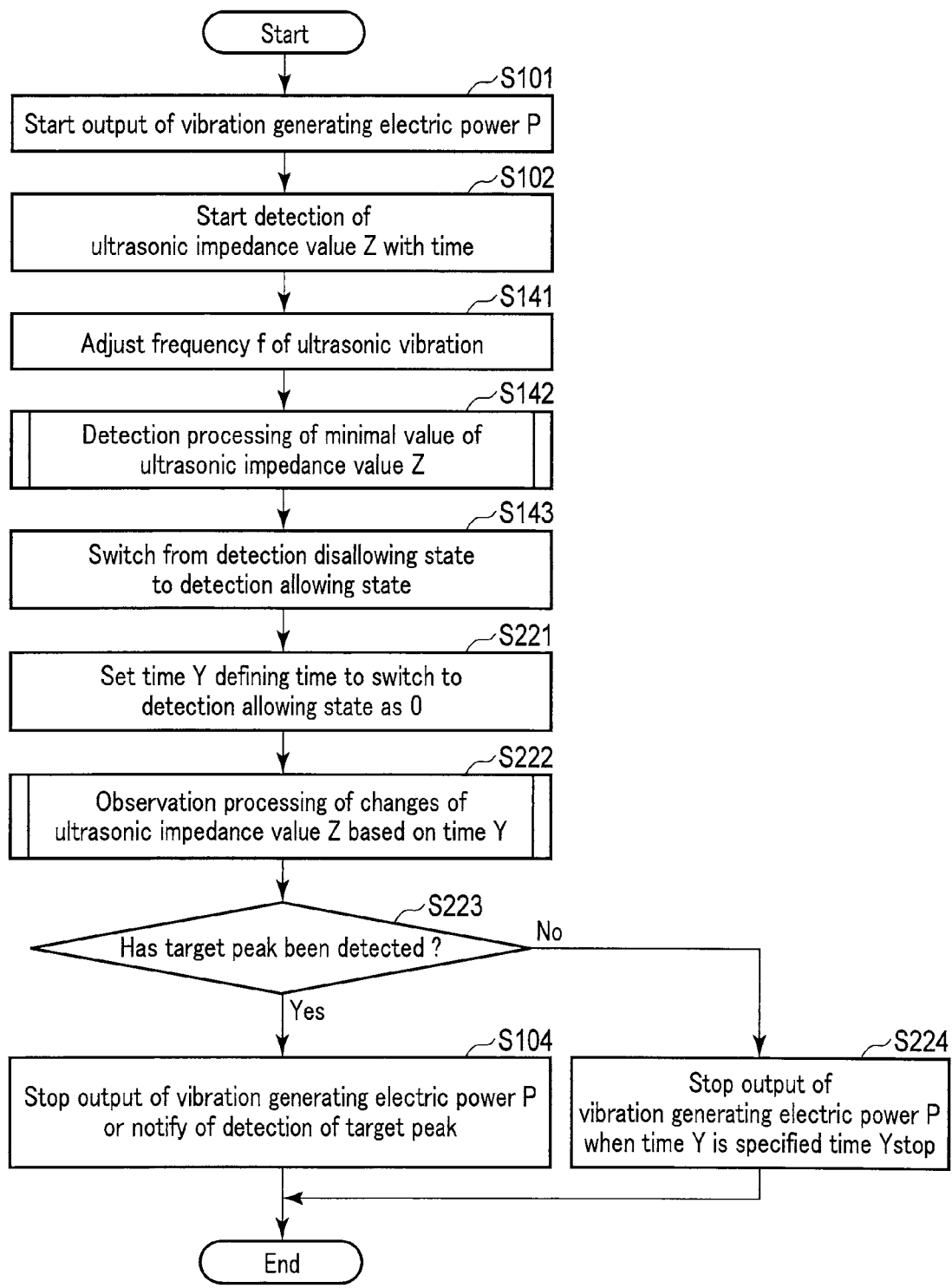
F I G. 44

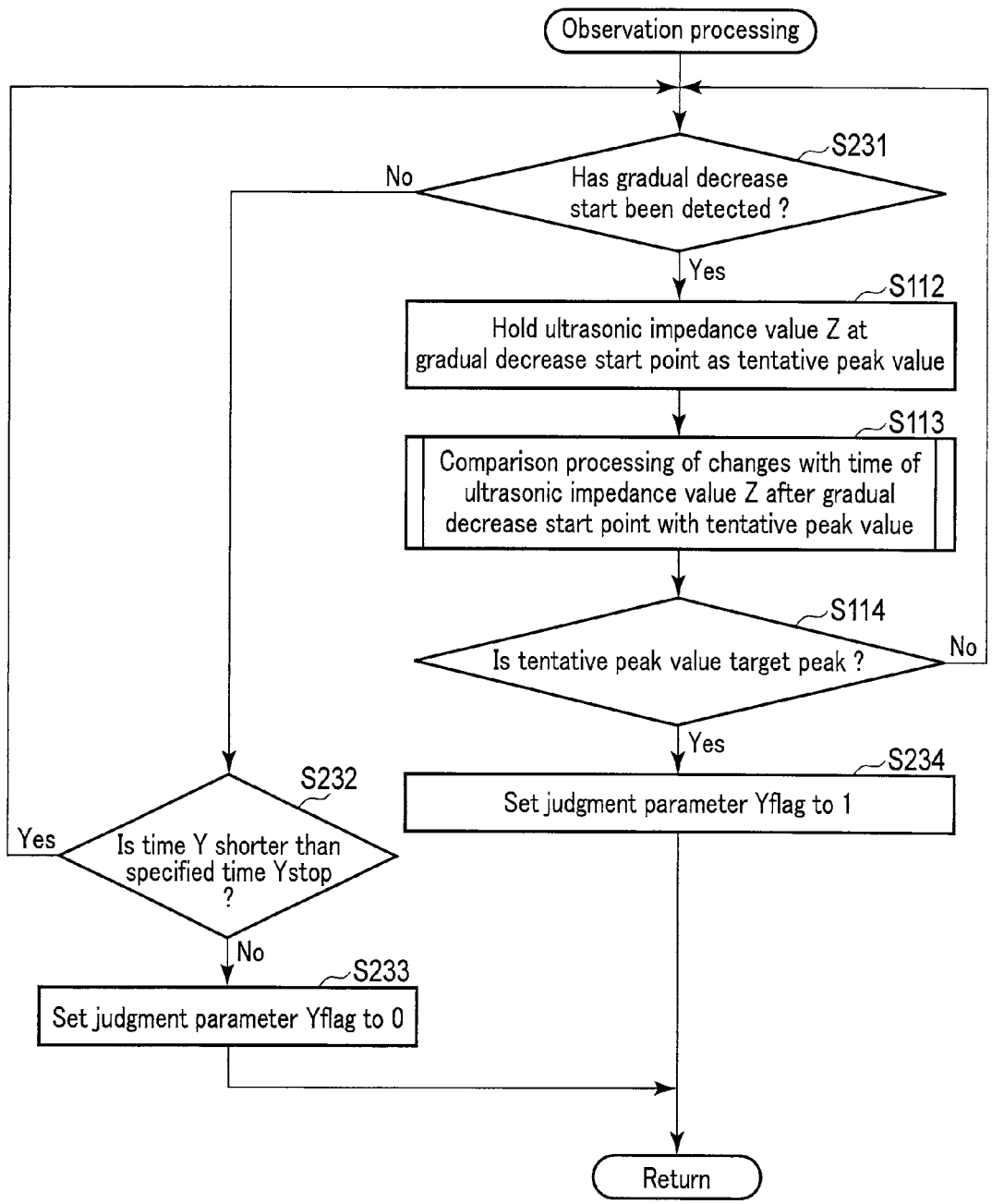
F I G. 45

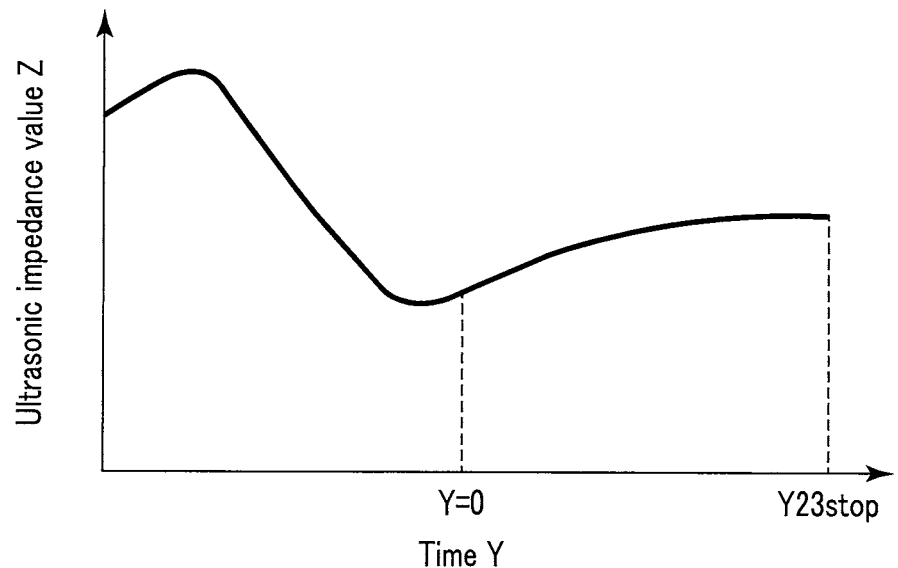
F I G. 46
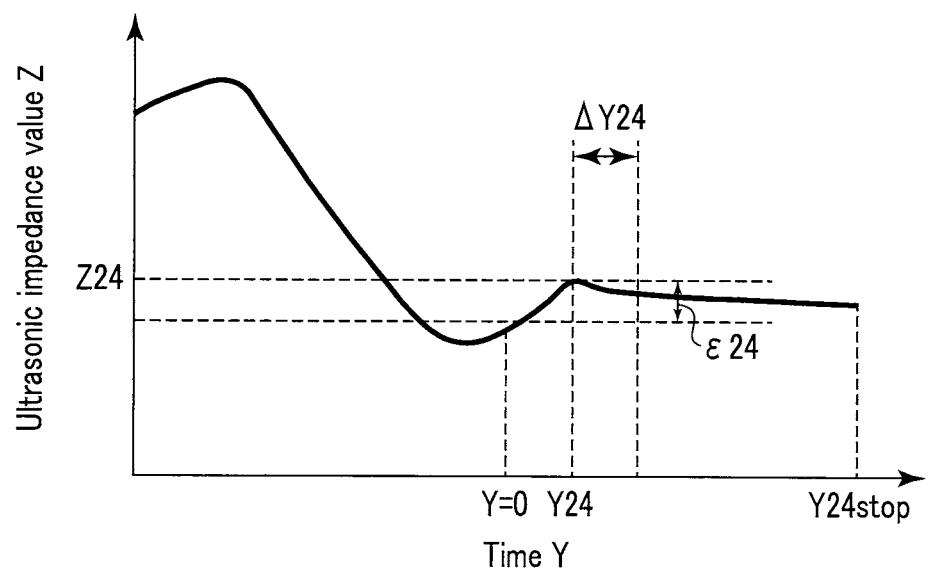
F I G. 47

ULTRASONIC TREATMENT APPARATUS

CROSS-REFERENCE TO RELATED APPLICATIONS

This is a Continuation Application of PCT Application No. PCT/JP2015/052868, filed Feb. 2, 2015 and based upon and claiming the benefit of priority from prior Japanese Patent Application No. 2014-027990, filed Feb. 17, 2014, the entire contents of which are incorporated herein by reference.

BACKGROUND OF THE INVENTION

1. Field of the Invention

The present invention relates to an ultrasonic treatment apparatus which grasps a treated target between a treatment section to which an ultrasonic vibration is transmitted and a jaw openable and closable relative to the treatment section, so as to treat the grasped treated target by use of the ultrasonic vibration.

2. Description of the Related Art

For example, U.S. Patent Application Publication No. 2012/0310264 discloses an ultrasonic treatment apparatus which includes a treatment section to which an ultrasonic vibration is transmitted and a jaw openable and closable relative to the treatment section. In this ultrasonic treatment apparatus, when vibration generating electric power is transmitted from an electric power source to a vibration generating section, the ultrasonic vibration is generated in an ultrasonic transducer which is the vibration generating section. Then, the generated ultrasonic vibration is transmitted to the treatment section, and the treatment section treats a treated target such as a biological tissue by use of the transmitted ultrasonic vibration. Here, opening and closing directions of the jaw are perpendicular (transverse) to a transmitting direction of the ultrasonic vibration. When the ultrasonic vibration is transmitted to the treatment section in a state where the treated target is grasped between the treatment section and the jaw, frictional heat is generated between the treated target and the treatment section. By the frictional heat, the treated target is coagulated and simultaneously incised. Furthermore, in the ultrasonic treatment apparatus, an ultrasonic impedance value of the vibration generating electric power is detected with time, and it is judged whether the ultrasonic impedance value is within a range of a first default threshold or more and a second default threshold or less, the second threshold being greater than the first threshold.

BRIEF SUMMARY OF THE INVENTION

According to one aspect of the invention, an ultrasonic treatment apparatus includes that: an electric power source which is configured to output vibration generating electric power; a vibration generating section which is configured to generate an ultrasonic vibration by supplying the vibration generating electric power from the electric power source; a treatment section to which the ultrasonic vibration generated in the vibration generating section is transmitted, and which is configured to perform a treatment by use of the transmitted ultrasonic vibration; a jaw which is openable and closable relative to the treatment section, and which includes a contact portion contactable with the treatment section in a state where the jaw is closed relative to the treatment section; an impedance detecting section which is configured to detect an ultrasonic impedance value of the vibration generating electric power with time, in a state where the vibration generating electric power is output from the electric power source; a gradual decrease detecting section which is configured to detect a gradual decrease start point to start gradual decrease of the ultrasonic impedance value on the basis of a detection result in the impedance detecting section; a tentative peak value holding section which is configured to hold the ultrasonic impedance value at the detected gradual decrease start point as a tentative peak value; and a peak judging section which is configured to judges whether the held tentative peak value is a target peak of a detection target by comparing, relative to the held tentative peak value, changes with time of the ultrasonic impedance value after the gradual decrease start point.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing an ultrasonic treatment apparatus according to a first embodiment;

FIG. 2 is a longitudinal cross-sectional view schematically showing a configuration of a transducer unit according to the first embodiment;

FIG. 3 is a schematic view showing an electrical connection state of an ultrasonic treatment instrument, a transducer unit, and a control unit according to the first embodiment;

FIG. 4 is a schematic exploded perspective view showing each member in a horn member and an ultrasonic transducer according to the first embodiment;

FIG. 5 is a schematic view showing an electrical connection state between the ultrasonic transducer and an electric power source according to the first embodiment;

FIG. 6 is a side elevation schematically showing a treatment section and a jaw according to the first embodiment;

FIG. 7 is a transverse cross-sectional view schematically showing cross sections of the treatment section and the jaw perpendicular to a longitudinal axis according to the first embodiment;

FIG. 15 is a flowchart showing comparison processing of changes with time of an ultrasonic impedance value relative to a tentative peak value executed by a peak judging section according to the first modification;

FIG. 25 is a schematic view showing an example of changes with time of an ultrasonic impedance value and changes with time of a frequency of ultrasonic vibration from an output start of the vibration generating electric power from an electric power source according to the third modification;

FIG. 26 is a schematic view showing an electrical connection state of an ultrasonic treatment instrument, a transducer unit, and a control unit according to a fourth modification;

FIG. 28 is a schematic view showing an example of a table stored in a memory section of the control unit according to the fourth modification;

FIG. 29 is a schematic view showing an electrical connection state of a transducer unit and a control unit according to a fifth modification;

FIG. 34 is a schematic view showing an example of changes with time of the ultrasonic impedance value and changes with time of a high-frequency impedance value from an output start of a vibration generating electric power and an output of a high-frequency electric power from an electric power source according to the third embodiment;

FIG. 35 is a schematic view schematically showing an example, which is different from the example depicted in FIG. 34, of changes with time of the ultrasonic impedance value and changes with time of the high-frequency impedance value from an output start of the vibration generating electric power and an output start of the high-frequency electric power from the electric power source according to the third embodiment;

FIG. 36 is a side elevation schematically showing a treatment section and a jaw according to a sixth modification;

FIG. 37 is a schematic view showing an example of changes with time of an ultrasonic impedance value from an output start of a vibration generating electric power from an electric power source according to the sixth modification;

FIG. 42 is a schematic view showing an example of changes with time of an ultrasonic impedance value from an output start of vibration generating electric power from an electric power source according to a second reference example;

FIG. 43 is a schematic view showing an example, which is different from the example depicted in FIG. 42, of changes with time of the ultrasonic impedance value from an output start of the vibration generating electric power from the electric power source according to the second reference example;

FIG. 44 is a flowchart showing an actuating state of a control unit from an output start of a vibration generating electric power according to a third reference example;

FIG. 45 is a flowchart showing an observation processing of changes of an ultrasonic impedance value executed by the control section and a peak detecting section according to the third reference example based on a time where a switching point to a detection allowing state is zero;

FIG. 46 is a schematic view showing an example of changes with time of the ultrasonic impedance value from an output start of a vibration generating electric power from an electric power source according to the third reference example; and FIG. 47 is a schematic view showing an example, which is different from the example depicted in FIG. 46, of changes with time of the ultrasonic impedance value from an output start of the vibration generating electric power from the electric power source according to the third reference example.

DETAILED DESCRIPTION OF THE INVENTION

First Embodiment

Figure 8:
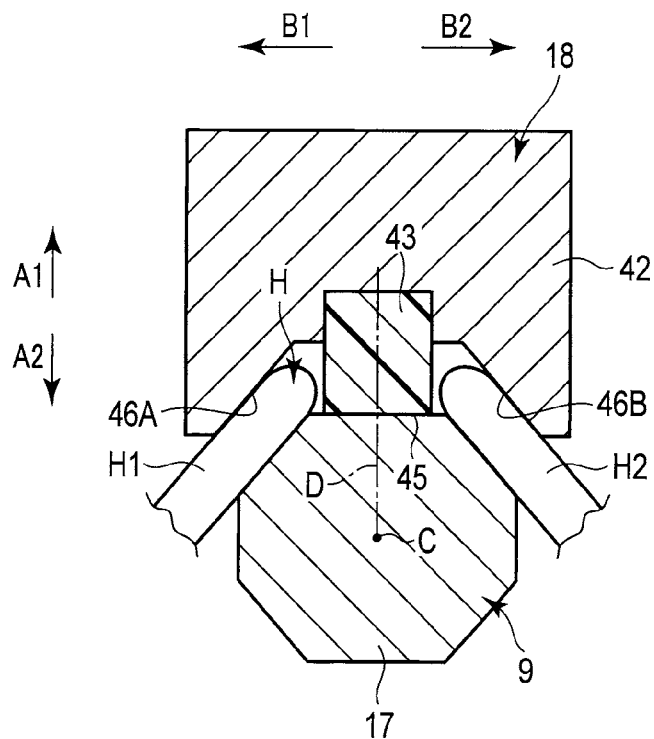
FIG. 8 is a schematic view for explaining cut-and-divided of a treated target grasped between the treatment section and the jaw according to the first embodiment.

A first embodiment according to the present invention will now be described with reference to FIG. 1 to FIG. 13. FIG. 1 is a view showing an ultrasonic treatment apparatus 1. As shown in FIG. 1, the ultrasonic treatment system 1 includes an ultrasonic treatment instrument (a hand piece) 2, a control unit (an energy control device) 3, and a transducer unit 5. The ultrasonic treatment tool 2 has a longitudinal axis C. One of two directions parallel to the longitudinal axis C is a distal direction (a direction of an arrow C1 in FIG. 1), and an opposite direction of the distal direction is a proximal direction (a direction of an arrow C2 in FIG. 1). The ultrasonic treatment instrument 2 includes a handle unit 6. The vibrator unit 5 is detachably coupled with a proximal direction side of the handle unit 6. One end of a cable 7 is connected to a proximal portion of the transducer unit 5. The other end of the cable 7 is connected to the control unit 3.

The handle unit 6 includes a tubular case portion 11 extended along the longitudinal axis C, a fixed handle 12 integrally formed with the tubular case portion 11, and a movable handle 13 coupled to the tubular case portion 11 to allow its turning motion. The fixed handle 12 is extended in a state that it is apart from the tubular case portion 11 to the longitudinal axis C. When the movable handle 13 turns around a position at which it is attached to the tubular case portion 11, the movable handle 13 opens or closes relative to the fixed handle 12. Further, the handle unit 6 includes a rotary operation knob 15 attached on a distal direction side of the tubular case portion 11. The rotary operation knob 15 can rotate around the longitudinal axis C relative to the tubular case portion 11. Furthermore, an energy operation input button 16 which is an energy operation input section is provided to the fixed handle 12.

The ultrasonic treatment instrument 2 includes a sheath 8 extended along the longitudinal axis C. The sheath 8 is inserted into the rotary operation knob 15 and into the tubular case portion 11 from the distal direction side, and the sheath 8 is attached to the handle unit 6. Moreover, the ultrasonic treatment instrument 2 includes an ultrasonic probe 9. The ultrasonic probe 9 is extended along the longitudinal axis C from an inside of the tubular case portion 11 through an inside of the sheath 8. The ultrasonic probe 9 is inserted through the sheath 8. Additionally, a treatment section 17 protruding from a distal end of the sheath 8 toward the distal direction is provided in a distal portion of the ultrasonic probe 9.

A jaw 18 is attached to the distal portion of the sheath 8 to allow its turning motion. Inside the tubular case portion 11, the movable handle 13 is connected to a movable tubular portion (not shown) that is arranged in a region located on an inner peripheral direction side of the sheath 8. A distal end of the movable tubular portion is connected to the jaw 18. When the movable handle 13 is opened or closed relative to the fixed handle 12, the movable tubular portion moves along the longitudinal axis C. Consequently, the jaw 18 turns around a position at which it is attached to the sheath 8. When the jaw 18 pivots relative the sheath 8, the jaw 18 is opened or closed relative to the treatment section 17. The sheath 8, the ultrasonic probe 9, and the jaw 18 can rotate together with the rotary operation knob 15 around the longitudinal axis C relative to the tubular case portion 11.

Further, the transducer unit 5 includes a transducer case 21. When the vibrator case 21 is inserted into the tubular case portion 11 from the proximal direction side, the transducer unit 5 is coupled to the handle unit 6 (the ultrasonic treatment instrument 2). Inside the tubular case portion 11, the vibrator case 21 is coupled with the sheath 8. The oscillator case 21 can rotate together with the rotary operation knob 15 around the longitudinal axis C relative to the tubular case portion 11.

FIG. 2 is a view showing a configuration of the transducer unit 5. As shown in FIG. 2, the transducer unit 5 includes the transducer case 21, an ultrasonic transducer 22 which is a vibration generating section provided inside the vibrator case 21, and a horn member 23 to which the ultrasonic vibrator 22 is attached. FIG. 3 is a view showing an electrical connection state of the ultrasonic treatment instrument 2, the transducer unit 5, and the control unit 3. As shown in FIG. 2 and FIG. 3, one end of each of electrical wiring portions 25A and 25B is connected to the ultrasonic oscillator 22. The control unit 3 includes an electric power source 26 that can output a vibration generating electric power P. In the electric power source 26, for example, an electric power from, e.g., a receptacle outlet or a direct-current power source is converted into the vibration generating electric power P by a conversion circuit or the like, and the vibration generating electric power P is output. The other end of each of the electrical wiring portions 25A and 25B is connected to the electric power source 26. The vibration generating electric power P output from the electric power source 26 is supplied to the ultrasonic transducer 22 through the electrical wiring portions 25A and 25B. When the vibration generating electric power P is supplied, an ultrasonic vibration is produced in the ultrasonic transducer 22.

A transducer mounting portion 27 to which the ultrasonic transducer 22 is mounted is provided to the horn member 23. The ultrasonic vibration produced by the ultrasonic vibrator 22 is transmitted to the horn member 23. Furthermore, a sectional area change portion 28 is provided to the horn member 23 on the distal direction side with respect to the transducer mounting portion 27. In the sectional area change portion 28, a sectional area perpendicular to the longitudinal axis C decreases toward the distal direction. The sectional area change portion 28 enlarges an amplitude of the ultrasonic vibration. A female screw portion 29A is provided in a distal portion of the horn member 23. Moreover, a male screw portion 29B is provided in a proximal portion of the ultrasonic probe 9. When the male screw portion 29B is screwed into the female screw portion 29A, the ultrasonic probe 9 is connected to the distal direction side of the horn member 23. The ultrasonic probe 9 is connected to the horn member 23 inside the tubular case portion 11. Consequently, the ultrasonic probe 9 is coupled with the ultrasonic transducer (the vibration generating section) 22 through the horn member 23.

The ultrasonic vibration transmitted to the horn member 23 is transmitted from the proximal direction toward the distal direction along the longitudinal axis C in the horn member 23 and the ultrasonic probe 9. That is, the horn member 23 and the ultrasonic probe 9 are a vibration transmitting portion configured to transmit the generated ultrasonic vibration. The ultrasonic vibration is transmitted toward the distal direction until it reaches the treatment section 17. The treatment section 17 gives a treatment to, e.g., a biological tissue by using the transmitted ultrasonic vibration. It is to be noted that, in the vibration transmitting portion (the horn member 23 and the ultrasonic probe 9), the proximal end (the proximal end of the horn member 23) and the distal end (the distal end of the ultrasonic probe 9) are antinode positions of the ultrasonic vibration. Additionally, the ultrasonic vibration is longitudinal vibration whose vibrating direction and whose transmitting direction are parallel to the longitudinal axis C (the longitudinal axial direction). Thus, the distal direction parallel to the longitudinal axis C is the transmitting direction of the ultrasonic vibration.

FIG. 4 is an exploded view showing each member in the horn member 23 and the ultrasonic transducer 22. As shown in FIG. 4, the ultrasonic vibrator 22 includes (four in this embodiment) ring-like piezoelectric elements 31A to 31D. The vibrator mounting portion 27 of the horn member 23 is inserted through the respective piezoelectric elements 31A to 31D. Further, the respective piezoelectric elements 31A to 31D are disposed on the transducer mounting portion 27 in a state that each of their thickness direction is parallel to the transmitting direction of the ultrasonic vibration (i.e., the longitudinal axis C) and each of their radial direction is perpendicular to the transmitting direction of the ultrasonic vibration (i.e., the distal end direction).

The ultrasonic oscillator 22 includes a first electrode portion 32 and a second electrode portion 33. One end of the electrical wiring portion 25A is connected to the first electrode portion 32, and one end of the electrical wiring portion 25B is connected to the second electrode portion 33. The first electrode portion 32 includes first electrode ring portions 35A to 35C. The first electrode ring portion 35A is placed on the distal direction side of the piezoelectric element 31A, and the first electrode ring portion 35B is placed between the piezoelectric element 31B and the piezoelectric element 31C in the longitudinal axial direction parallel to the longitudinal axis C. Furthermore, the first electrode ring unit 35C is placed on the proximal direction side of the piezoelectric element 31D. The transducer mounting portion 27 is inserted through the respective first electrode ring portions 35A to 35C.

The second electrode portion 33 includes second electrode ring portions 37A and 37B. The second electrode ring portion 37A is placed between the piezoelectric element 31A and the piezoelectric element 31B in the longitudinal axial direction parallel to the longitudinal axis C. Moreover, the second electrode ring portion 37B is placed between the piezoelectric element 31C and the piezoelectric element 31D in the longitudinal axial direction. The vibrator mounting unit 27 is inserted through the respective second electrode ring portions 37A and 37B.

With the above-described configuration, the piezoelectric element 31A is held between the first electrode ring portion 35A and the second electrode ring portion 37A, and the piezoelectric element 31B is sandwiched between the second electrode ring portion 37A and the first electrode ring portion 35B. Additionally, the piezoelectric element 31C is held between the first electrode ring portion 35B and the second electrode ring portion 37B, and the piezoelectric element 31D is held between the second electrode ring portion 37B and the first electrode ring portion 35C. Thus, the respective piezoelectric elements 31A to 31D are held between the first electrode portion 32 and the second electrode portion 33.

Further, the ultrasonic transducer 22 includes insulation rings 38A and 38B. The insulation ring 38A is placed on the distal direction side of the first electrode ring portion 35A of the first electrode portion 32. The insulation ring 38B is placed on the proximal direction side of the first electrode ring portion 35C of the first electrode portion 32. The transducer mounting portion 27 is inserted through the respective insulation rings 38A and 38B. Furthermore, the ultrasonic transducer 22 includes a back mass 36. The back mass 36 is placed on the proximal direction side of the insulation ring 38B. The piezoelectric elements 31A to 31D, the first electrode portion 32, the second electrode portion 33, and the insulation rings 38A and 38B are pressed toward the distal direction by the back mass 36. Consequently, the piezoelectric elements 31A to 31D, the first electrode portion 32, the second electrode portion 33, and the insulation rings 38A and 38B are held between the horn member 23 and the back mass 36.

FIG. 5 is a view showing an electrical connection state between the ultrasonic transducer 22 which is a vibration generating section and the electric power source 26. As shown in FIG. 5, the electric power source 26 is electrically connected to the first electrode portion 32 by the electrical wiring portion 25A. Further, the electric power source 26 is electrically connected to the second electrode portion 33 by the electrical wiring portion 25B. When the vibration generating electric power P is output from the electric power source 26, a vibration generating voltage V is applied between the first electrode portion 32 and the second electrode portion 33. When the vibration generating voltage V is applied, a vibration generating current I flows through the piezoelectric elements 31A to 31D sandwiched between the first electrode portion 32 and the second electrode portion 33. The vibration generating current I is an alternating current whose current direction periodically changes. Furthermore, an ultrasonic impedance value Z which is an impedance value of the vibration generating electric power P is represented by Expression (1).

[Expression 1]

$$Z = V/I = V^2/P \tag{1}$$

FIG. 6 and FIG. 7 are views showing configurations of the treatment section 17 and the jaw 18. Here, FIG. 6 shows a state where the jaw 18 is opened relative to the treating section 17, and FIG. 7 shows a state where a treated target is not present between the jaw 18 and the treatment section 17 and the jaw 18 is closed relative to the treatment section 17. Moreover, FIG. 7 shows a cross section perpendicular to the longitudinal axis C. As shown in FIG. 6 and FIG. 7, the jaw 18 includes a jaw main body 41 whose proximal portion is attached to the sheath 8, and a grasp member 42 attached to the jaw main body 41. The jaw main body 41 and the grip member 42 are formed of, e.g., a metal having electrical conductivity. Additionally, the jaw 18 includes a pad member 43 attached to the grasp member 42. The pad member 43 is made of, e.g., PTFE (polytetrafluoroethylene) having electrical insulation properties.

A contact portion (a contact surface) 45, which is contactable with the treatment section 17 in a state where the jaw 18 is closed relative to the treatment section 17, is formed on the pad member 43. When the jaw 18 is closed relative to the treatment section 17 in a state where no treated target is present between the jaw 18 and the treatment section 17, the abutment portion section 45 of the pad member 43 comes into contact with the treatment section 17. The contact portion 45 is opposed to the treatment section 17. Moreover, in this embodiment, the abutment portion 45 is perpendicular to an opening direction (a direction of an arrow A1 in each of FIG. 6 and FIG. 7) and a closing direction (a direction of an arrow A2 in each of FIG. 6 and FIG. 7) of the jaw 18.

Here, two directions which are perpendicular (transverse) to the longitudinal axis C and also perpendicular to the opening and closing directions of the jaw 18 are defined as a first width direction (a direction of an arrow B1 in FIG. 7) and a second width direction (a direction of an arrow B2 in FIG. 7). An inclined facing portion 46A that faces the treatment section 17 in a state where it is inclined relative to the contact portion 45 is formed on the first width direction side of the contact portion 45 by the grasp member 42. Further, an inclined facing portion 46B opposed to the treatment section 17 in a state where it is inclined relative to the abutment portion 45 is formed on the second width direction side of the contact portion 45 by the grip member 42. In a state where the contact portion 45 is in abutment with the treatment section 17, the inclined facing portions 46A and 46B are apart from the treatment section 17. Thus, in a state where the contact portion 45 is in contact with the treatment section 17, the grasp member 42 does not come into contact with the treatment section 17.

As shown in FIG. 3, the control unit 3 includes a control section 51 electrically connected to the electric power source 26. A switch portion 47 is provided inside the fixed handle 12. Opened and closed states of the switch portion 47 are changed over based on input of an energy operation using the energy operation input button 16. The switch portion 47 is connected to the control section 51 via a signal path portion 48 extended through the transducer case 21 and the inside of the cable 7. When the switch portion 47 is closed, an operation signal is transmitted to the control section 51 through the signal path portion 48. The control section 51 controls an output state of the vibration generating electric power P from the electric power source 26 based on the transmitted operation signal.

Furthermore, the control unit 3 includes an impedance detecting section 52 electrically connected to the electric power source 26 and the control section 51, and a peak detecting section 53 electrically connected to the impedance detecting section 52 and the control section 51. In a state where the vibration generating electric power P is output from the electric power source 26, the impedance detecting section 52 detects an ultrasonic impedance value Z of the vibration generating electric power P with time. The peak detecting section 53 detects a peak of the ultrasonic impedance value Z (a target peak) based on changes with time of the detected ultrasonic impedance value Z. The peak detecting section 53 includes a gradual decrease detecting section 55, a tentative peak value holding section 56, and a peak judging section 57. Details of the gradual decrease detecting section 55, the tentative peak value holding section 56, and the peak judging section 57 will be described later. It is to be noted that the impedance detecting section 52 is, e.g., a detection circuit. Furthermore, each of the control section 51 and the peak detecting section 53 is formed of, e.g., a processor including a CPU (Central Processing Unit) or an ASIC (application specific integrated circuit) or a logic circuit such as an FPGA (Field Programmable Gate Array), and a memory (a memory section).

Moreover, the control unit 3 includes a switching operation section 58 and a notifying section 59 such as a buzzer or a lamp. The switching operation section 58 is electrically connected to the control section 51. The switching operation section 58 inputs a switching operation between a detection disallowing state (a non-detection state) in which the peak detecting section 53 does not perform detection and judgment (determination) of a tentative peak and a target peak and a detection allowing state in which the peak detecting section 53 performs detection of the tentative peak and the target peak. Additionally, the notifying section 59 is electrically connected to the control section 51. The notifying section 59 notifies that the target peak has been detected. It is to be noted that an explanation of the target peak and a detection method of the target peak will be described later.

A function and an effect of the ultrasonic treatment apparatus 1 will now be described later. At the time of giving a treatment to a treated target such as a biological tissue by using the ultrasonic treatment system 1, the sheath 8, the ultrasonic probe 9, and the jaw 18 are inserted into a body or the like in which a treated target is present. Further, the treatment section 17 and the jaw 18 are moved until the treated target is placed between the jaw 18 opened relative to the treating section 17 and the treatment section 17. Furthermore, when the movable handle 13 is closed relative to the fixed handle 12, the treated target is grasped between the treatment section 17 and the jaw 18. In this state, an energy operation is input by the energy operation input button 16, an operation signal is transmitted to the control section 51, and output of the vibration generating electric power P from the electric power source 26 begins. When the vibration generating electric power P is supplied, the vibration generating current I is converted into an ultrasonic vibration by the piezoelectric elements 31A to 31D. At this time, the control section 51 controls an output state of the vibration generating electric power P by a constant-current control that maintains (a wave height of) the vibration generating current I constant. Thus, the vibration generating voltage V is adjusted in accordance with changes in ultrasonic impedance value Z so as to realize a state where the vibration generating current I becomes constant.

The ultrasonic vibration generated by the ultrasonic transducer 22 is transmitted to the treatment section 17 through the horn member 23 and the ultrasonic probe 9, and the treatment section 17 longitudinally vibrates. When the treatment section 17 longitudinally vibrates in a state where the treated target is griped between the treatment section 17 and the jaw 18, frictional heat is generated between the treated target and the treatment section 17. The frictional heat enables coagulating and simultaneously incising the treated target.

When a treatment is given to the treated target held between the treatment section 17 and the jaw 18, cut-and-divided of the treated target occurs in at least a part range of the treated target in the transmitting direction of the ultrasonic vibration. FIG. 8 is a view for explaining the cut-and-divided of the treated target H grasped between the treatment section 17 and the jaw 18. It is to be noted the cut-and-divided occurs over the entire range of the treated target in the transmitting direction (the longitudinal axial direction) of the ultrasonic vibration in some cases, or it occurs only in a part range the treated target in the transmitting direction (the longitudinal axis direction) of the ultrasonic vibration in some cases. In a region where the cutoff has occurred, the treated target H is divided at a dividing face D that is parallel to the transmitting direction of the ultrasonic vibration and also parallel to the opening and closing directions of the jaw (a direction of an arrow A1 in FIG. 8 and a direction of an arrow A2 in FIG. 8). The dividing face D is perpendicular to the first width direction (a direction of an arrow B1 in FIG. 8) and a second width direction (a direction of an arrow B2 in FIG. 8). Thus, in the range where the cut-and-divided has occurred, the treated target H is divided into a region H1 on the first width direction side of the dividing face D and a region H2 on the second width direction side of the dividing face D.

In the range where the treated target H is divided by the cut-and-divided, the contact portion 45 of the jaw 18 comes into contact with the treatment section 17. When the abutment portion 45 of the jaw 18 vibrates (longitudinally vibrates) by the ultrasonic vibration in a state where it is in contact with the treatment section 17, the contact portion 45 of the jaw 18 is destroyed due to wear, thermal deformation, or the like. Thus, it is important to appropriately judge whether the treated target H has been cut-and-divided.

Figure 9:
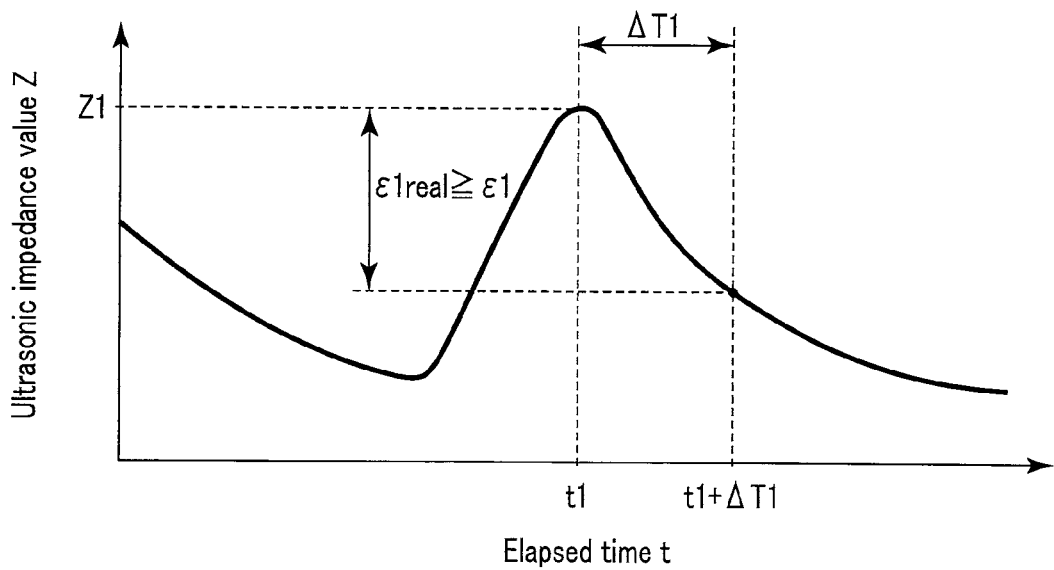
FIG. 9 is a schematic view showing an example of changes with time of an ultrasonic impedance value from an output start of a vibration generating electric power from the electric power source according to the first embodiment.

Here, the ultrasonic impedance value Z of the vibration generating electric power P changes in accordance with a load to the ultrasonic probe 9, i.e., a load to the ultrasonic transducer 22 connected to the ultrasonic probe 9. FIG. 9 shows an example of changes with time in an ultrasonic impedance value Z from an output start of the vibration generating electric power P from the electric power source 26. In FIG. 9, an axis of ordinate represents the ultrasonic impedance value Z, and an axis of abscissa represents an elapsed time t from an output start of the vibration generating electric power P. Pressing force to the treatment section 17 from the jaw 18 gradually increases up to the vicinity of a time point at which the treated target H is cut-and-divided due to, e.g., changes in a state of the treated target H between the contact portion 45 of the jaw 18 and the treatment section 17. Thus, the ultrasonic impedance value Z gradually increases with time until the treatment target H is cut-and-divided. Here, the term of the gradual increase with time means that the ultrasonic impedance value Z gradually increases as the elapsed time t advances, and it also includes that the ultrasonic impedance value Z gradually increases while including a small increase or decrease of tens of $\Omega$ or less.

When the treated target H is cut-and-divided, since the contact portion 45 of the jaw 18 is placed near the treatment section 17, a surface of the pad member 43 (the contact portion 45) denatures due to frictional heat generated by the ultrasonic vibration of the treatment section 17. Thus, the load to the ultrasonic probe 9 is gradually decreased. Therefore, the ultrasonic impedance value Z gradually decreases subsequent to the vicinity of the time point where the treated target H is cut off. Here, gradually decreasing with time means that the ultrasonic impedance value Z gradually decreases as the elapsed time t advances, and it also includes that the ultrasonic impedance value Z gradually decreases while including a small increase or decrease of tens of $\Omega$ or less.

Since the ultrasonic impedance value Z changes due to the cut-and-divided as described above, the ultrasonic impedance value Z becomes a peak (a maximal value) with time in the vicinity of a time point when the treated target H is cut-and-divided (for example, in the vicinity of a time point when the contact portion 45 of the jaw 18 begins to come into contact with the treatment section 17). When the time-dependent peak of the ultrasonic impedance value Z is detected, it can be appropriately judged whether the treated target H has been cut-and-divided. Here, in the example shown in FIG. 9, an ultrasonic impedance value Z1 becomes a target peak which is a peak (peak value) caused due to the cut-and-divided of the treated target H. Further, an elapsed time t1 is a target peak point at which the target peak is produced.

Figure 10:
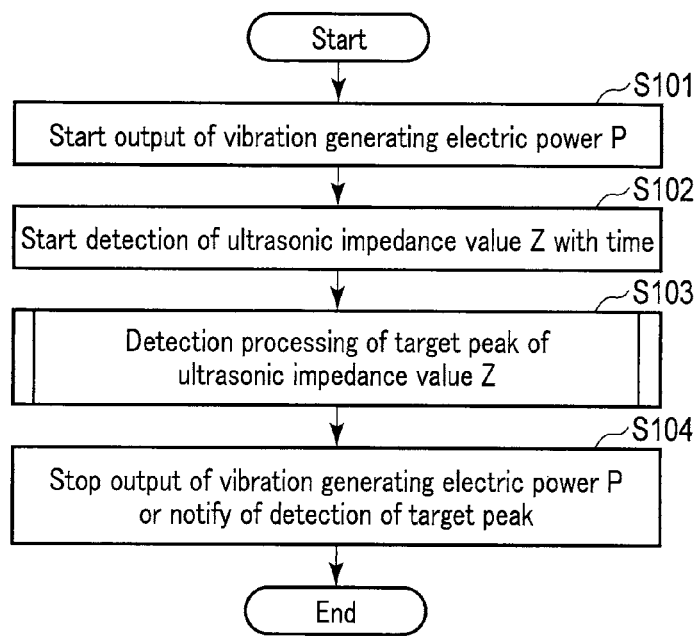
FIG. 10 is a flowchart showing an actuating state of the control unit from an output start of the vibration generating electric power according to the first embodiment in a detection allowing state.

FIG. 10 is a view showing an actuating state of the control unit 3 from an output start of the vibration generating electric power P in the detection allowing state. As shown in FIG. 10, when output of the vibration generating electric power P from the electric power source 26 is started (a step S101), the impedance detecting section 52 starts detection of the ultrasonic impedance value Z of the vibration generating electric power P with time (a step S102). Consequently, the ultrasonic impedance value Z is detected with time. For example, to fix an amplitude of the ultrasonic vibration, when constant-current control that maintains (a wave height of) the vibration generating current I is performed, changes with time of at least one of the vibration generating electric power P and the vibration generating voltage V are detected. Furthermore, based on the detected vibration generating electric power P and/or the vibration generating voltage V, the ultrasonic impedance value Z is calculated by using Expression (1). Consequently, the ultrasonic impedance value Z is detected with time. Moreover, in a given embodiment, the impedance detecting section 52 detects the vibration generating voltage V and the vibration generating current I with time, and calculates the ultrasonic impedance value Z by using Expression (1).

Additionally, the peak detecting section 53 executes detection processing of a target peak of the ultrasonic impedance value Z produced due to the cut-and-divided of the treated target H based on the changes with time of the ultrasonic impedance value Z (a step S103). At this time, a target peak point at which the ultrasonic impedance value Z becomes the target peak (a target peak value) may be detected. It is to be noted that, when a state is changed to the detection disallowing state by the switching operation in the switching operation section 58, the target peak is not detected by the peak detecting section 53. Thus, the control section 51 controls the peak detecting section 53 (the gradual decrease detecting section 55, the tentative peak value holding section 56, and the peak judging section 57) to the detection disallowing state or the detection allowing state based on the switching operation by the switching operation section 58. For example, even though the target peak is not detected by the peak detecting section 53, and when an operator who can judge whether the treated target has been cut-and-divided uses the ultrasonic treatment apparatus 1, the state is switched to the detection disallowing state, and a treatment is given.

When the target peak is detected, in a given example, the control section 51 stops output of the vibration generating electric power P from the electric power source 26 or gradually decreases the output with time (a step S104). When the output is gradually decreased, for example, the output is linearly, stepwisely, or exponentially decreased with time. Consequently, the ultrasonic probe 9 no longer longitudinally vibrates, and wear of the contact portion 45 is avoided even though the abutment portion 45 of the jaw 18 comes into contact with the treatment section 17. In particular, when the output is gradually decreased with time, incomplete cutoff of the treated target H can be avoided, and heat generation of the treatment section 17 can be prevented. Further, in another embodiment, the notifying section 59 notifies that the target peak has been detected (the step S104). Here, electronic sound is produced when the notifying section 59 is a buzzer, or lighting is performed when the notifying section 59 is a lamp. Thus, a surgeon judges whether the treated target H has been cut-and-divided by use of the notifying section 59.

Figure 11:
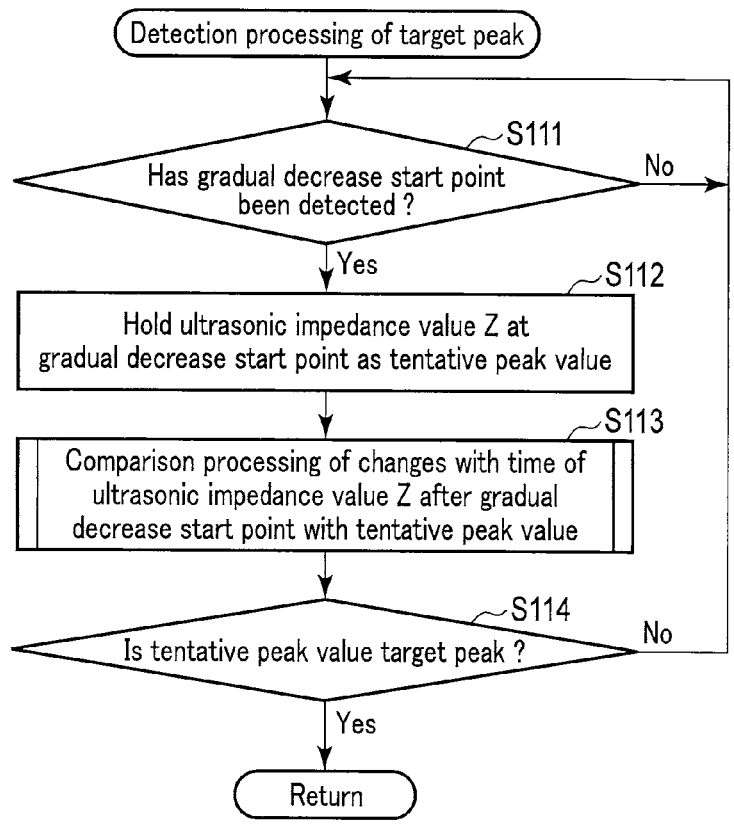
FIG. 11 is a flowchart showing detection processing of a target peak executed by a peak detecting section according to the first embodiment.

FIG. 11 is a view showing the detection processing (the step S103 in FIG. 10) of the target peak of the ultrasonic impedance value Z executed by the peak detecting section 53. That is, FIG. 11 shows a method of detecting the target peak by the peak detecting unit 53 in the detection allowing state. As shown in FIG. 11, in the detection processing of the target peak, first, the gradual decrease detecting section 55 detects a gradual decrease start point at which the ultrasonic impedance value Z starts to gradually decrease based on a detection result of the ultrasonic impedance value Z in the impedance detecting unit 52 (a step S111). In the example shown in FIG. 9, the elapsed time tl is detected as the gradual decrease start point. When the gradual decrease start point is detected (the step S111—Yes), the tentative peak value holding section 56 holds the ultrasonic impedance value Z at the detected gradual decrease start point as a tentative peak value (a step S112). In the example shown in FIG. 9, the ultrasonic impedance value Z1 at the elapsed time tl is held as the tentative peak value.

Furthermore, the peak judging section 57 executes comparison processing of changes with time of the ultrasonic impedance value after the gradual decrease start point relative to the held tentative peak value (a step S113). In the example shown in FIG. 9, in the comparison processing of the step S113, changes with time of the ultrasonic impedance value Z after the elapsed time tl are compared relative to the ultrasonic impedance value Z1 held as the tentative peak value. Moreover, based on the comparison of the changes with time of the ultrasonic impedance value Z relative to the tentative peak value, the peak judging section 57 judges whether the tentative peak value is the target peak caused due to the cut-and-divided of the treated target H (a step S114). In the example shown in FIG. 9, a judgment is made upon whether the ultrasonic impedance value Z1 held as the tentative peak value is the target peak (the target peak value). At this time, whether the detected gradual decrease start point is a target peak point may be judged. In the example shown in FIG. 9, the elapsed time t1 which is the gradual decrease start point is judged to be the target peak point at a time point which is the elapsed time t1+$\Delta$T1. In this case, the peak judging section 57 outputs a signal to the control section 51, and the control section 51 actuates the notifying section 59 and others.

Figure 12:
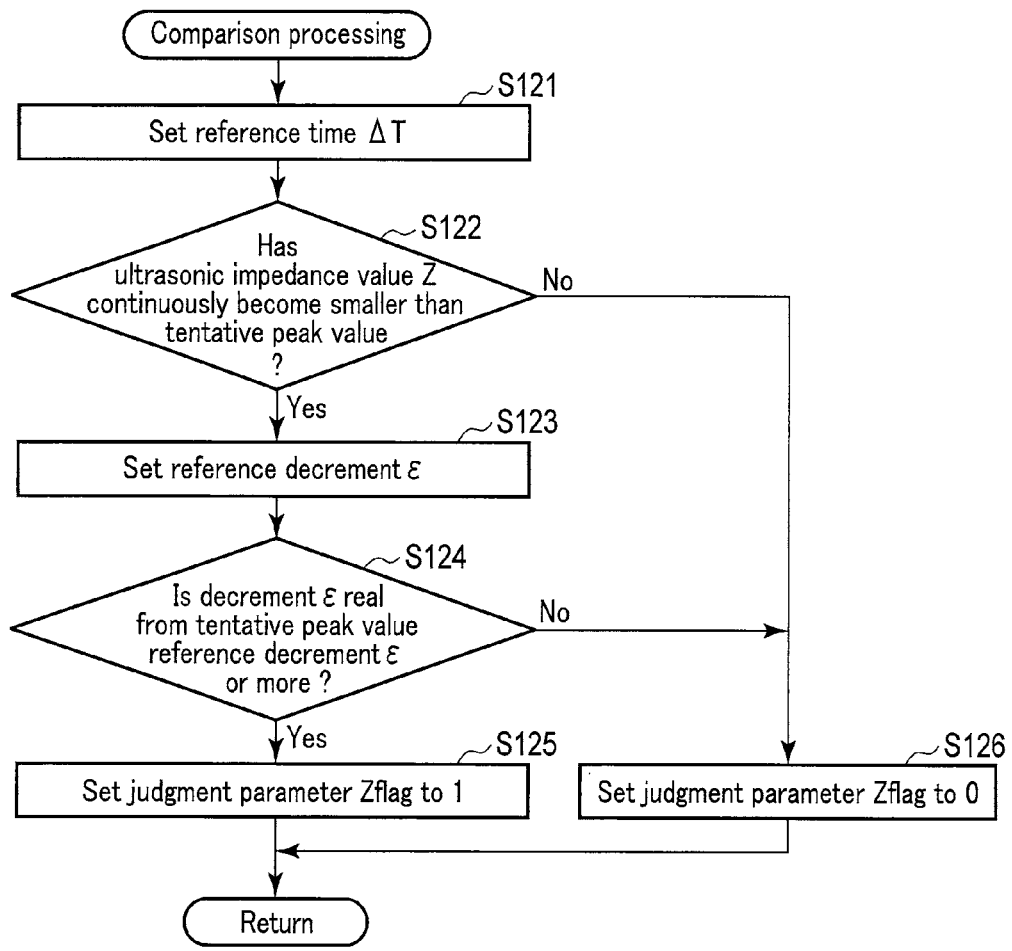
FIG. 12 is a flowchart showing comparison processing of changes with time of the ultrasonic impedance value relative to a tentative peak value executed by a peak judging section according to the first embodiment.

FIG. 12 is a view showing the comparison processing (the step S113 of FIG. 11) of changes with time of the ultrasonic impedance value Z after the gradual decrease start point relative to the tentative peak value executed by the peak judging section 57. That is, FIG. 12 shows a method of comparing changes with time of the ultrasonic impedance value Z relative to the tentative peak value by the peak judging section 57 in the detection allowing state. As shown in FIG. 12, at the time of comparing changes with time of the ultrasonic impedance value Z relative to the tentative peak value, a reference time $\Delta$T during which the comparison is performed is first set (a step S121). During the reference time $\Delta$T from the gradual decrease start point, the changes with time of the ultrasonic impedance value Z are compared relative to the tentative peak value. Moreover, after elapse of the reference time $\Delta$T from the gradual decrease start point, a judgment on whether the tentative peak value is the target peak is started. In the example shown in FIG. 9, the reference time during which the comparison is performed is set to $\Delta$T1, and whether the ultrasonic impedance value Z1 held as the tentative peak value is the target peak is judged after the elapsed time t1+$\Delta$T1.

Here, the reference time $\Delta$T is not set to a specified length, and it may be set in accordance with changes with time or the like of the ultrasonic impedance value Z. In this case, a length of the reference time $\Delta$T varies depending on situations. In a given example, the length of the reference time $\Delta$T is set based on the tentative peak value, i.e., the ultrasonic impedance value Z at the gradual decrease start point. Additionally, in another example, the length of the reference time $\Delta$T is set based on an average value Zave of the ultrasonic impedance value Z during a period from an output start of the vibration generating electric power P from the electric power source 26 to the gradual decrease start point.

Further, after elapse of the reference time $\Delta$T, the peak judging section 57 judges whether the ultrasonic impedance value Z has continuously become smaller than the tentative peak value after the gradual decrease start point by comparison (a step S122). In the example shown in FIG. 9, it is judged by comparison whether the ultrasonic impedance value Z has continuously become smaller than the tentative peak value Zl. When the ultrasonic impedance peak value Z has reach the tentative peak value or more after the gradual decrease start point (the step S122—No), a judgment parameter Zflag is set to 0 (a step S126). When the judgment parameter Zflag is 0, it is judged in the step S114 of FIG. 11 that the tentative peak value which is the ultrasonic impedance value Z at the gradual decrease start point is not the target peak (the target peak value) caused due to the cut-and-divided (the step S114—No).

Figure 13:
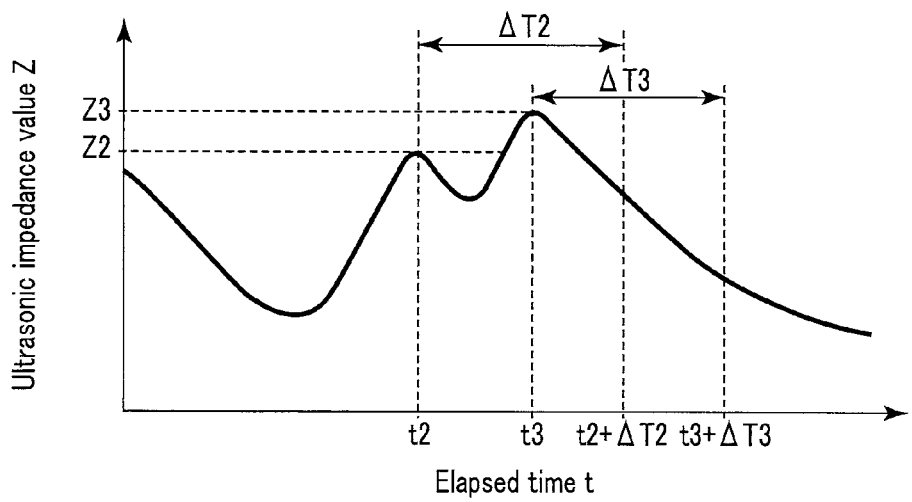
FIG. 13 is a schematic view showing an example, which is different from the example depicted in FIG. 9, of changes with time of the ultrasonic impedance value from an output start of the vibration generating electric power from the electric power source according to the first embodiment.

FIG. 13 shows an example, which is different from FIG. 9, of changes with time of the ultrasonic impedance value Z from an output start of the vibration generating electric power P from the electric power source 26. In FIG. 13, like FIG. 9, an axis of ordinate represents the ultrasonic impedance value Z, and an axis of abscissa represents the elapsed time t from an output start of the vibration generating electric power P. For example, when the treated target H is thick (a dimension of the treated target H is large in the opening and closing directions of the jaw 18), a peak of the ultrasonic impedance value Z is produced at a moment when the contact portion 45 of the jaw 18 comes into contact with the treated target H and a contact surface of the treated target H to the jaw 17 starts to be incised. In this case, the peak of the ultrasonic impedance value Z due to the contact of the contact portion 45 with the treated target H is produced before the target peak caused by the cut-and-divided. In the example shown in FIG. 13, at an elapsed time t2, the ultrasonic impedance value Z reaches a peak (a peak value) Z2 due to the contact of the contact portion 45 with the treated target H. Moreover, at an elapsed time t3 after the elapsed time t2, the ultrasonic impedance value Z turns to a target peak (a target peak value) Z3 due to the cut-and-divided of the treated target H. It is to be noted that, in the example shown in FIG. 13, the target peak value Z3 is larger than the peak Z2.

When the ultrasonic impedance value Z has changed with time as shown in FIG. 13, the elapsed time t2 is detected as the gradual decrease start point of the ultrasonic impedance value Z in the step S111, and the peak Z2 is held as a tentative peak value in the step S112. In this embodiment, the comparison of the step S122 is performed, and even if the ultrasonic impedance value Z has changed with time as shown in FIG. 13, it is judged in the judgment of the step S114 that the peak Z2 held as the tentative peak value is not the target peak due to the cut-and-divided.

That is, when the ultrasonic impedance value Z changes with time as shown in FIG. 13, a reference time ΔT2 is set in the step S112. A length of the reference time ΔT2 is set to be longer than a length from the elapsed time t2 to the elapsed time t3. Here, in the example shown in FIG. 13, the target peak Z3 at the elapsed time t3 is higher than the peak Z2 at the elapsed time t2. Thus, during elapse of the reference time ΔT2 from the elapsed time t2 which is the gradual decrease start point, the ultrasonic impedance value Z becomes equal to or higher than the peak Z2 that is held as the tentative peak value. Thus, by the comparison of the step S122, the ultrasonic impedance value Z is judged to have become the tentative peak value (Z2) or more. Further, in a step S126, the judgment parameter Zflag is set to 0, and in the step S114 of FIG. 11, it is judged that the peak Z2 is not the target peak (the target peak value) caused due to the cut-and-divided, and the tentative peak value holding section 56 updates the tentative peak value Z2 to the new tentative peak value Z3 and holds the new tentative peak value Z3 together with the time t3.

As shown in FIG. 12, when the ultrasonic impedance value Z continuously falls below the tentative peak value during the reference time ΔT (the step S122—Yes), a reference decrement 6 of the ultrasonic impedance value Z is set (a step S123). Furthermore, whether a decrement εreal of the ultrasonic impedance value Z from the tentative peak value is equal to or higher than the reference decrement 6 after elapse of the reference time ΔT from the decrease start point is judged by comparison (a step S124). The reference time ΔT and the reference decrement 6 are parameters for use in a judgment upon whether the tentative peak value is the target peak made by the peak judging section 57.

Here, the reference decrement ε is not set to a specific magnitude, and it may be set in accordance with, e.g., changes with time of the ultrasonic impedance value.

Thus, the magnitude of the reference decrement 6 changes in accordance with situations. In a given example, the magnitude of the reference decrement ε is set based on the tentative peak value, i.e., the ultrasonic impedance value Z at the gradual decrease start point. For example, as the tentative peak value increases, the reference decrement ε is also set to be higher. Moreover, in another example, the magnitude of the reference decrement ε is set based on an average value Zave of the ultrasonic impedance value Z in a period from an output start of the vibration generating electric power P from the electric power source 26 to the gradual decrease start point. For example, as the average value Zave increases, the reference decrement E is also set to be higher.

When the decrement εreal of the ultrasonic impedance value Z falls below the reference decrement E during elapse of the reference time ΔT (the step S124—No), the judgment parameter Zflag is set to 0 (the step S126). Thus, in the step S114 of FIG. 11, it is judged that the tentative peak value which is the ultrasonic impedance value Z at the gradual decrease start point is not the target peak (the target peak value) caused due to the cutoff (the step S114—No). On the other hand, when the decrement Ereal of the ultrasonic impedance value Z becomes equal to or more than the reference decrement ε during elapse of the reference time ΔT (the step S124—Yes), the judgment parameter Zflag is set to 1 (a step S125). When the judgment parameter Zflag is 1, in the step S114 of FIG. 11, the tentative peak value which is the ultrasonic impedance value Z at the gradual decrease start point is judged to be the target peak (the target peak value) caused due to the cut-and-divided (the step S114—Yes). When the tentative peak value at the gradual decrease start point is judged to be the target peak, the target peak is detected. When the target peak is detected (identified) by the peak judging section 57, an information signal of this detection is transmitted to the control section 51.

In the example shown in FIG. 9, in the step S123, the reference decrement ε1 is set. Additionally, a decrement ε1real of the ultrasonic impedance value Z during elapse of the reference time ΔT1 from the elapsed time t1 which is the gradual decrease start point is a reference decrement ε1 or more. Thus, at the step S124, the decrement s1real of the ultrasonic impedance value Z is judged to be the reference decrement ε1 or more. Further, in the step S125, the judgment parameter Zflag is set to 1, and in the step S114 of FIG. 11, the peak Z1 is judged to be the target peak (the target peak value) caused due to the cut-and-divided.

When the tentative peak value at the gradual decrease start point is judged not to be the target peak caused due to the cut-and-divided (the step S114—No), the processing returns to the step S111. In the example shown in FIG. 13, after the ultrasonic impedance value Z becomes the tentative peak value Z2 or more, the ultrasonic impedance value Z starts again to gradually decrease. In this case, in the step Sill, the gradual decrease detecting section 55 detects the elapsed time t3 which is a gradual decrease start point at which the gradual decrease restarts (a gradual decrease restart point). Furthermore, in the step S112, the tentative peak value holding section 56 holds the ultrasonic impedance value Z3 at the elapsed time (the gradual decrease restart point) t3 as a tentative peak value. At this time, the held tentative peak value Z2 is updated to the ultrasonic impedance value Z3 at the elapsed time t3, and the updated tentative peak value Z3 is held together with the elapsed time t3.

Moreover, in the step S113, changes with time of the ultrasonic impedance value Z are compared relative to the updated tentative peak value Z3 until the reference time ΔT3 passes from the elapsed time (the gradual decrease restart point) t3. At this time, the comparison processing is executed in accordance with the steps S121 to S126 shown in FIG. 12. Additionally, in the step S114, the ultrasonic impedance value Z3 at the gradual decrease restart point held as the updated tentative peak value is judged to be the target peak (the target peak value) caused due to the cut-and-divided.

In the ultrasonic treatment apparatus 1 according to this embodiment, the gradual decrease start point of the ultrasonic impedance value Z is detected, and the ultrasonic impedance value Z at the gradual decrease start point is held as the tentative peak value. Further, the changes with time of the ultrasonic impedance value Z after the gradual decrease start point are compared with the tentative peak value, thereby judging whether the held tentative peak value is the target peak as a detection target. Thus, the target peak can be appropriately detected irrespective of a magnitude of the target peak (the target peak value) caused due to the cut-and-divided. Therefore, in a treatment of the treated target H grasped between the treatment section 17 and the jaw 18 using the ultrasonic vibration, it is possible to appropriately judge whether the treatment target H has been appropriately cut-and-divided.

Furthermore, in the ultrasonic treatment apparatus 1 in this embodiment, as described above, even if a peak (e.g., Z2) caused due to contact of the contact portion 45 with the treated target H is produced before a target peak (e.g., Z3), it is judged that the peak (e.g., Z2) caused due to the contact of the contact portion 45 with the treatment target H is not the target peak. Thus, even if a peak (e.g., Z2) different from a target peak (e.g., Z3) is produced before the target peak (e.g., Z3), the target peak can be appropriately detected.

Modification of First Embodiment

As a modification of the first embodiment, a first modification will now be described with reference to FIG. 14 to FIG. 16. It is to be noted that like reference numerals denote parts equal to those in the first embodiment to omit a description thereof.

Figure 14:
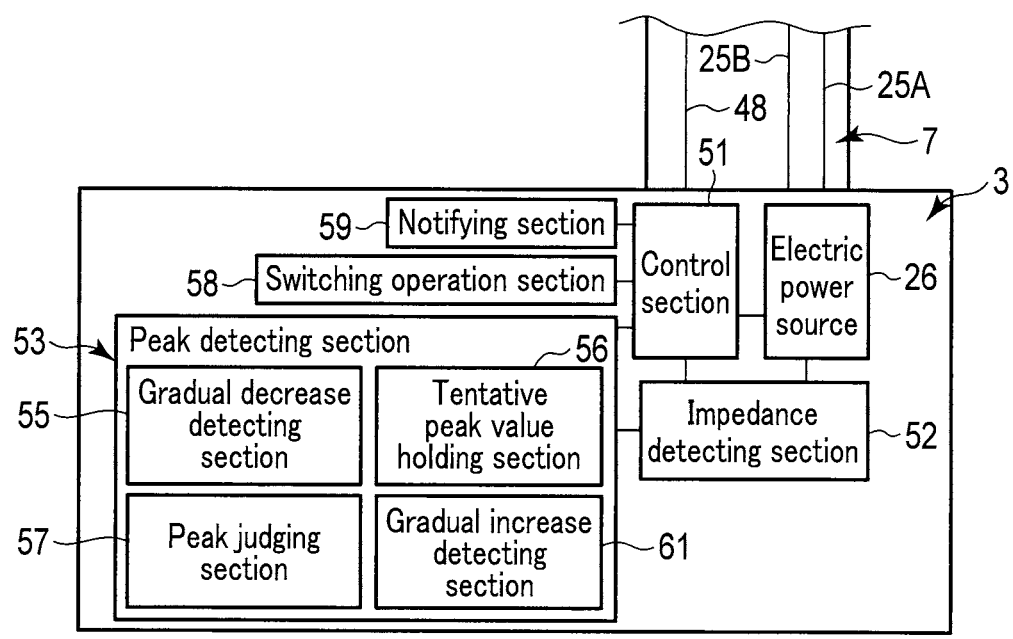
FIG. 14 is a schematic view showing a configuration of a control unit according to a first modification.

FIG. 14 is a view showing the control unit 3 according to this modification. In this modification, the peak detecting section 53 of the control unit 3 includes the gradual decrease detecting section 55, the tentative peak value holding section 56, the peak judging section 57, and the gradual increase detecting section 61 as well. Other structures are the same as the control unit 3 according to the first embodiment.

FIG. 15 is a view showing comparison processing (the step S113 of FIG. 11) of changes with time of the ultrasonic impedance value Z after a gradual decrease start point relative to a tentative peak value executed by the peak judging section 57. That is, FIG. 15 shows a method of comparing changes with time of the ultrasonic impedance value Z relative to the tentative peak value by the peak judging section 57 in a detection allowing state. As shown in FIG. 15, in this modification, the comparison of the step S122 in the first embodiment is not executed. However, in this modification, likewise, the steps S121 and S123 to S126 are executed like the first embodiment.

In this modification, when the ultrasonic impedance value Z starts to gradually increase after the gradual decrease start point, the gradual increase detecting section 61 detects a gradual increase start point at which a gradual increase starts. Thus, when a reference time ΔT is set in the step S121, whether the ultrasonic impedance value Z has gradually increased during elapse of the reference time ΔT from the gradual decrease start point is judged (a step S131). When the ultrasonic impedance value Z has not gradually increased, (the step S131—No), the processing advances to the step S123.

When the ultrasonic impedance value Z has gradually increased (the step S131—Yes), whether an increment ξreal of the ultrasonic impedance value Z from the gradual increase start point has become equal to or higher than a reference increment ξ is judged (a step S132). When the increment ξreal of the ultrasonic impedance value Z is smaller than the reference increment ξ (the step S132—No), the processing advances to the step S123. On the other hand, when the increment ξreal of the ultrasonic impedance value Z has become equal to or higher than the reference increment ξ, the processing advances to the step S126, and the judgment parameter Zflag is set to 0. Thus, in the step S114 of FIG. 11, it is judged that a tentative peak value which is the ultrasonic impedance value Z at the gradual decrease start point is not a target peak caused due to the cut-and-divided. It is to be noted that the reference increment ξ may be set in accordance with changes with time or the like of the ultrasonic impedance value Z, and it may be set to a specified value. Further, the reference increment ξ is a parameter for use in a judgment upon whether the tentative peak value is the target peak made by the peak judging section 57.

Figure 16:
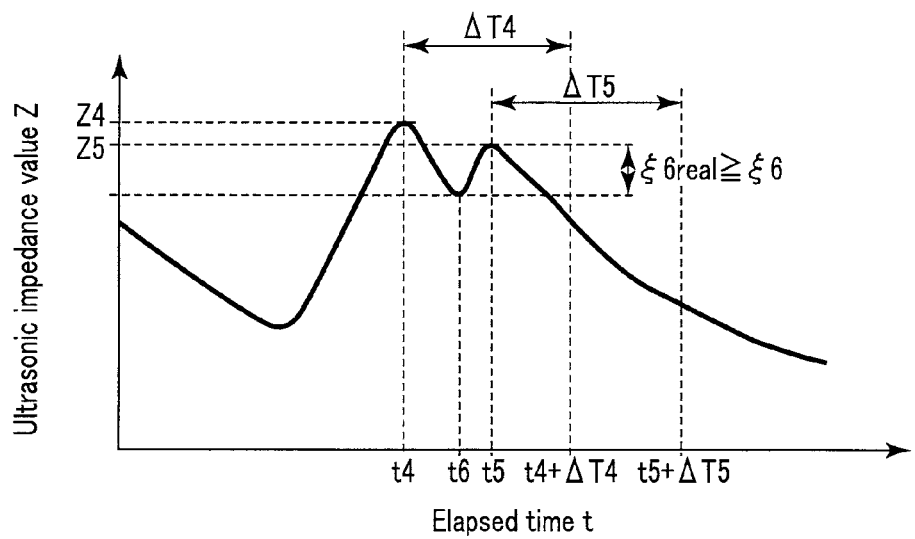
FIG. 16 is a schematic view showing an example of changes with time of the ultrasonic impedance value from an output start of vibration generating electric power from a electric power source according to a first modification.

FIG. 16 shows an example, which is different from FIG. 9 and FIG. 13, of changes with time of the ultrasonic impedance value Z from an output start of the vibration generating electric power P from the electric power source 26. In FIG. 16, like FIG. 9, an axis of ordinate represents the ultrasonic impedance value Z, and an axis of abscissa represents the elapsed time t from an output start of the vibration generating electric power P. As described in the first embodiment, a peak of the ultrasonic impedance value Z may be produced due to contact of the contact portion 45 with the treated target H before the target peak caused due to the cut-and-divided depending on circumstances. In this case, the target peak (a target peak value) caused due to the cutoff may be smaller than the peak (a peak value) caused due to contact of the contact portion 45 with the treated target H. In the example shown in FIG. 16, the ultrasonic impedance value Z becomes a peak (a peak value) Z4 due to contact of the contact portion 45 with the treated target H. Furthermore, at an elapsed time t5 following an elapsed time t4, the ultrasonic impedance value Z becomes a target peak (a target peak value) Z5 due to the cut-and-divided of the treated target H. Moreover, in the example shown in FIG. 16, the target peak Z5 is smaller than the peak Z4.

When the ultrasonic impedance value Z changes with time as shown in FIG. 16, the elapsed time t4 is detected as a gradual decrease start point of the ultrasonic impedance value Z in the step S111, and the peak Z4 is held as a tentative peak value in the step S112. In this embodiment, since the steps S131 and S132 are carried out, even if the ultrasonic impedance value Z changes with time as shown in FIG. 16, it is judged in the judgment of the step S114 that the peak Z4 held as the tentative peak value is not the target peak caused due to the cut-and-divided.

That is, when the ultrasonic impedance value Z changes with time as shown in FIG. 16, a reference time ΔT4 is set in the step S121. A length of the reference time ΔT4 is set to be equal to a length from the elapsed time t4 to the elapsed time t5 or longer than the length from the elapsed time t4 to the elapsed time t5. Moreover, the gradual increase detecting section 61 detects an elapsed time t6 as the gradual increase start point. The gradual increase start point t6 is produced after the elapsed time t4 and before the elapsed time t5. Thus, in the step S131, the ultrasonic impedance value Z is judged to have gradually increased.

Here, in the example shown in FIG. 16, an increment ξ6real of the ultrasonic impedance value Z from the elapsed time t6 which is the gradual increase start point becomes equal to or higher than a reference increment ξ6. Thus, in the step S132, the increment ξ6real of the ultrasonic impedance value Z is judged to be equal to or higher than the reference increment 46. Moreover, the judgment parameter Zflag is set to 0 in the step S126, and in the step S114 of FIG. 11, it is judged that the peak Z4 is not the target peak (the target peak value) caused due to the cut-and-divided.

Additionally, in the example shown in FIG. 16, after the increment ξ6real of the ultrasonic impedance value Z from the elapsed time (the gradual increase start point) t6 has become equal to or higher than the reference increment ξ6, the ultrasonic impedance value Z starts again to gradually decrease. In this case, in the step S111, the gradual decrease detecting section 55 detects the elapsed time t5 that is the gradual decrease start point at which gradual decrease starts again (a gradual decrease restart point). Further, in the step S112, the tentative peak value holding section 56 holds the ultrasonic impedance value Z5 at the elapsed time (the gradual decrease restart point) t5 as a tentative peak value. At this time, the held tentative peak value Z4 is updated to the ultrasonic impedance value Z5 at the elapsed time t5, and the updated tentative peak value Z5 is held.

Furthermore, in the step S113, changes with time of the ultrasonic impedance value are compared relative to the updated tentative peak value Z5 until the reference time ΔT5 passes from the elapsed time (the gradual decrease start point) t5. At this time, the comparison processing is executed in accordance with the steps S121, S123 to 126, S131, and S132 shown in FIG. 12. Moreover, in the step S114, the ultrasonic impedance value Z5 at the gradual decrease restart point held as the updated tentative peak value is judged to be the target peak (the target peak value) caused due to the cut-and-divided.

In the ultrasonic treatment apparatus 1 according to this modification, as described above, even if a peak (e.g., Z4) caused due to contact of the contact portion 45 with the treated target H is produced before a target peak (e.g., Z5) and the target peak (e.g., Z5) is smaller than the peak (e.g., Z4) caused due to the contact of the contact portion 45 with the treated target H, the peak (e.g., Z4) caused due to contact of the contact portion 45 with the treated target H is judged not to be the target peak. Thus, even if a peak (e.g., Z4) different from the target peak (e.g., Z5) is produced before the target peak (e.g., Z4) and the target peak (e.g., Z5) is smaller than the peak (e.g., Z4) different from the target peak, the target peak can be appropriately detected.

It is to be noted that, as another modification, the control unit 3 of the ultrasonic treatment apparatus 1 may be applied in a state where both the step S122 of the first embodiment and the steps S131 and S132 of the first modification are executed.

Second Embodiment

A second embodiment according to the present invention will now be described with reference to FIG. 17 to FIG. 21. The second embodiment is provided by modifying the configuration of the first embodiment as follows. It is to be noted that like reference numerals denote parts equal to those in the first embodiment to omit a description thereof.

Figure 17:
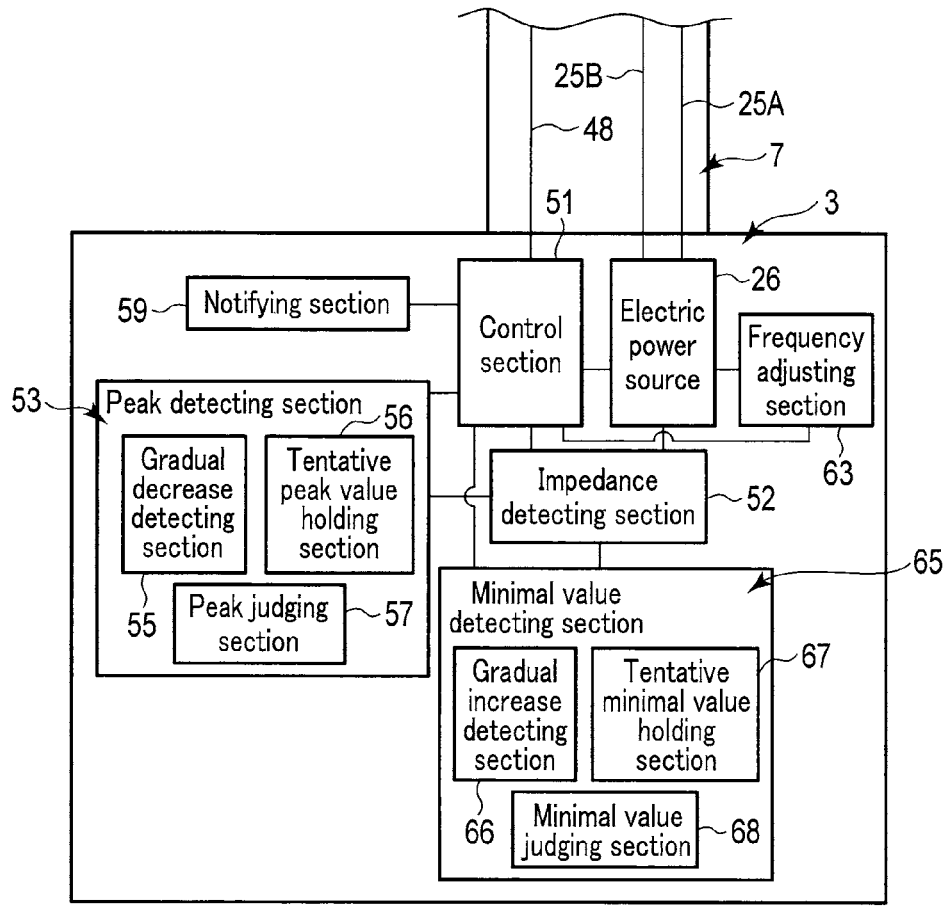
FIG. 17 is a schematic view showing a configuration of a control unit according to a second embodiment.

FIG. 17 is a view showing a control unit 3 according to this embodiment. In this embodiment, the control unit 3 according to this embodiment includes a frequency adjusting section 63 and a minimal value detecting section 65 in addition to an electric power source 26, a control section 51, an impedance detecting section 52, a peak detecting section 53, and a notifying section 59. The frequency adjusting section 63 is electrically connected to the electric power source 26 and the control section 51. Further, the minimal value detecting section 65 is electrically connected to the control section 51 and the impedance detecting section 52. Furthermore, the minimal value detecting section 65 includes a gradual increase detecting section 66, a tentative minimal value holding section 67, and a minimal value judging section 68. Moreover, in this embodiment, a switching operation section 58 is not provided. It is to be noted that each of the frequency adjusting section 63 and the minimal value detecting section 65 is formed of, e.g., a processor including a CPU or an ASIC, or a logic circuit such as an FPGA (Field Programmable Gate Array), and a memory (a memory section).

Figure 18:
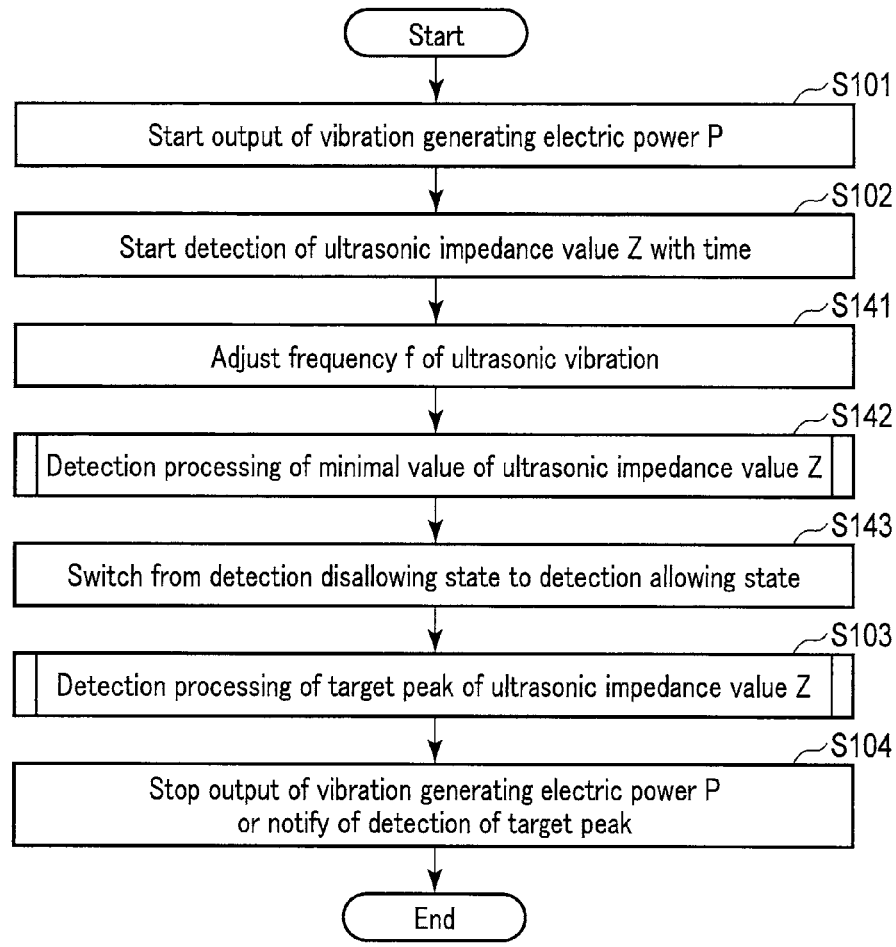
FIG. 18 is a flowchart showing an actuating state of a control unit from an output start of a vibration generating electric power unit according to the second embodiment.

FIG. 18 is a view showing an actuating state of the control unit 3 from an output start of a vibration generating electric power P in this embodiment. As shown in FIG. 18, in this embodiment, like the first embodiment, output of the vibration generating electric power P from the electric power source 26 is started in a step S101, and detection of an ultrasonic impedance value Z of the vibration generating electric power P with time is started in a step S102. However, in this embodiment, after an output start of the vibration generating electric power P from the electric power source 26, adjustment of a frequency f of an ultrasonic vibration is performed by the frequency adjusting section 63 (a step S141).

Figure 19:
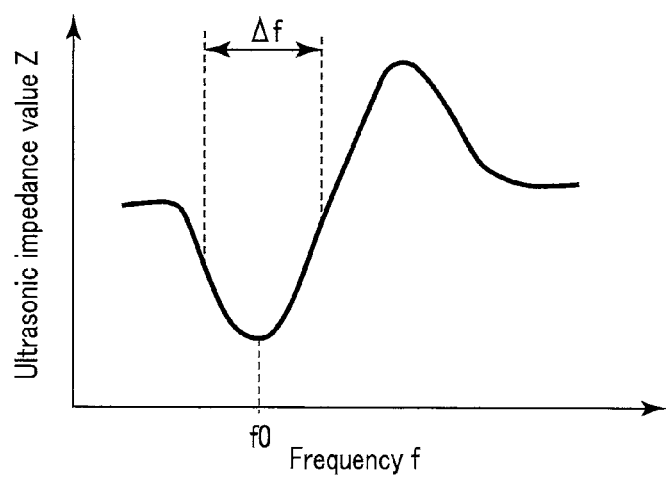
FIG. 19 is a schematic view showing a relationship between a frequency near a resonance frequency of an ultrasonic vibration and an ultrasonic impedance value in the second embodiment.

FIG. 19 is a view showing a relationship between a frequency (a frequency of a vibration generating current I) f of the ultrasonic vibration and the ultrasonic impedance value Z in a resonance frequency and a nearby the resonance frequency. As shown in FIG. 19, when the frequency f of the ultrasonic vibration changes, the ultrasonic impedance value Z varies. The frequency adjusting section 63 adjusts the frequency of the vibration generating current I based on the relationship between the frequency f of the ultrasonic vibration and the ultrasonic impedance value Z. Consequently, the frequency f of the ultrasonic vibration is adjusted. In the relationship between the ultrasonic impedance value Z and the frequency f, with a resonance frequency f0, the ultrasonic impedance value Z becomes minimal (minimum). Thus, the frequency adjusting section 63 adjusts the frequency f of the ultrasonic vibration to the resonance frequency f0. Moreover, a treatment to incise the treated target H while coagulating the same is given by use of the ultrasonic vibration having the resonance frequency f0.

The adjustment of the frequency f of the ultrasonic vibration is carried out by PLL (Phase Locked Loop) control. That is, the frequency f with which the ultrasonic impedance value Z becomes minimum (minimal) in a predetermined frequency range Δf of the ultrasonic vibration is detected as the resonance frequency f0. Additionally, the vibration generating electric power P from the electric power source 26 is adjusted to a state where the ultrasonic vibration having the resonance frequency f0 is produced.

Figure 20:
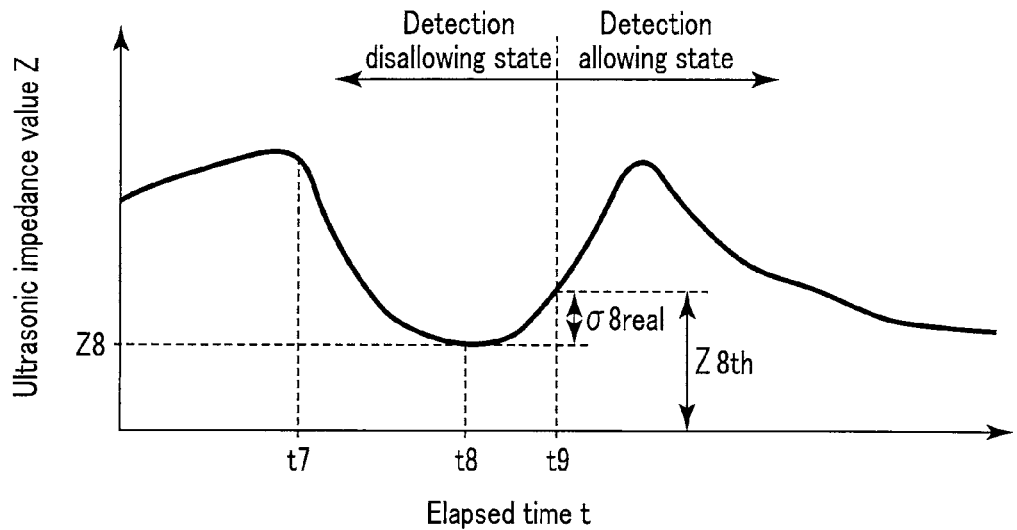
FIG. 20 is a schematic view showing an example of changes with time of the ultrasonic impedance value from an output start of the vibration generating electric power from an electric power source according to the second embodiment.

FIG. 20 is a view showing an example of changes with time of the ultrasonic impedance value when the frequency f of the ultrasonic vibration is adjusted. In FIG. 20, an axis of ordinate represents the ultrasonic impedance value Z, and an axis of abscissa represents an elapsed time t from an output start of the vibration generating electric power P. In a case where the frequency f of the ultrasonic vibration is adjusted, the ultrasonic impedance value Z is gradually decreased due to the adjustment of the frequency f before a target peak caused due to cut-and-divided. Further, in the vicinity of a time point at which the frequency f is adjusted to the resonance frequency f0, the ultrasonic impedance value Z becomes a minimal value. In the example shown in FIG. 20, at an elapsed time t7, the adjustment of the frequency f of the ultrasonic vibration begins. Furthermore, at an elapsed time t8, the ultrasonic impedance value Z becomes a minimal value Z8. Here, in the example shown in FIG. 20, the elapsed time t7 is an adjustment start point, and the elapsed time t8 is a minimal point.

As shown in FIG. 18, in this embodiment, after the adjustment start point when the adjustment of the frequency f of the ultrasonic vibration is started, the minimal value detecting section 65 executes detection processing of a minimal value that allows the ultrasonic impedance value Z to become minimal with time (a step S142). At this time, the minimal point at which the ultrasonic impedance value Z becomes a minimal value may be detected. Here, after the adjustment start when the adjustment of the frequency f of the ultrasonic vibration is started, a time point when the minimal value is first detected by the minimal value detecting section 65 is defined as a minimal detection point. At the minimal detection point when the minimal value of the ultrasonic impedance value Z is detected, the control section 51 switches from a detection disallowing state where a detection of the target peak is not performed to a detection allowing state where the detection of the target peak is executed (a step S143). That is, the control section 51 maintains the detection disallowing state until the minimal detection point. When the state is switched to the detection allowing state, like the first embodiment, detection processing of the target peak caused due to the cut-and-divided is executed (a step S103). That is, the peak detecting section 53 (the gradual decrease detecting section 55, the tentative peak value holding section 56, and the peak judging section 57) is controlled to a state where the detection of the target peak is not executed until the minimal detection point.

Figure 21:
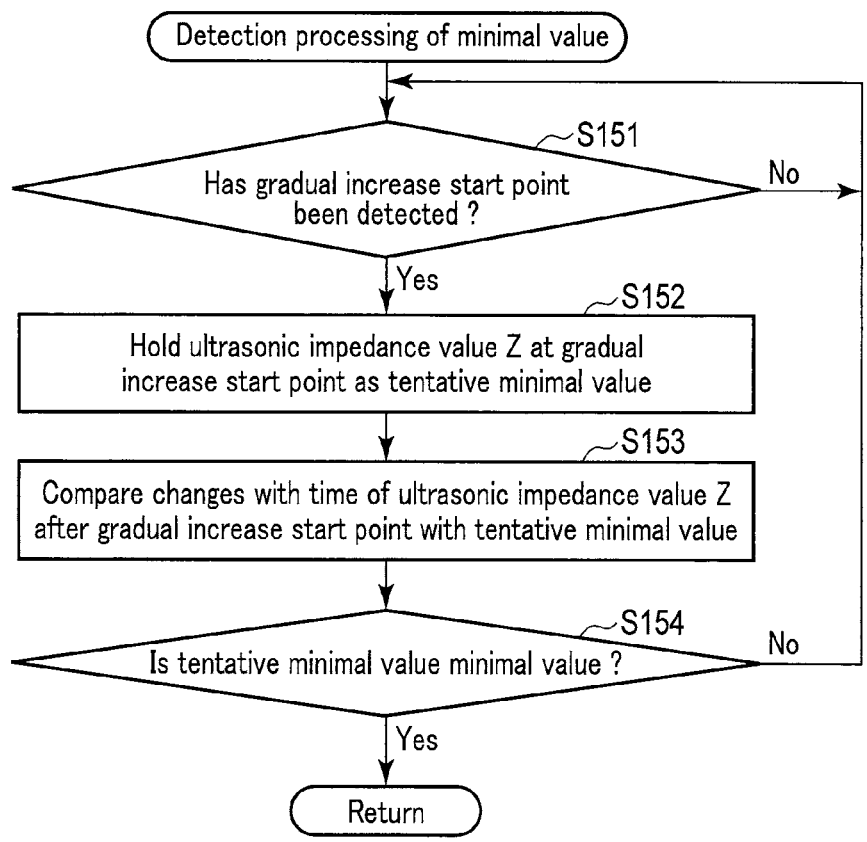
FIG. 21 is a flowchart showing detection processing of a minimal value executed by a minimal value detecting section according to the second embodiment.

FIG. 21 is a view showing detection processing (the step S142 in FIG. 18) of the minimal value of the ultrasonic impedance value Z executed by the minimal value detecting section 65. That is, FIG. 21 shows a method of detecting the minimal value. As shown in FIG. 21, at the time of detecting the minimal value, the gradual increase detecting section 66 first detects a gradual increase start point at which the ultrasonic impedance value Z starts to gradually increase based on a detection result of the ultrasonic impedance value Z provided by the impedance detecting section 52 (a step S151). In the example shown in FIG. 20, the elapsed time t8 is detected as the gradual increase start point. When the gradual increase start point has been detected (the step S151—Yes), the tentative minimal value holding section 67 holds the ultrasonic impedance value Z at the detected gradual increase start point as a tentative minimal value (a step S152). In the example shown in FIG. 20, the ultrasonic impedance value Z8 at the elapsed time t8 is held as the tentative minimal value.

Further, the minimal value judging section 68 compares changes with time of the ultrasonic impedance value Z after the gradual increase start point relative to the held tentative minimal value (a step S153). In the example shown in FIG. 20, changes with time of the ultrasonic impedance value Z after the elapsed time t8 are compared with an ultrasonic impedance value Z8 held as the tentative minimal value. Furthermore, based on the comparison of the changes with time of the ultrasonic impedance value Z relative to the tentative minimal value, the minimal value judging section 68 judges whether the tentative minimal value is the minimal value (a step S154). In the example shown in FIG. 20, whether the ultrasonic impedance value Z8 held as the tentative minimal value is the minimal value is judged. At this time, whether the detected gradual increase start point is the minimal time may be judged.

The comparison of the ultrasonic impedance value Z relative to the tentative minimal value and the judgment on the minimal value are performed based on, e.g., whether or not an increment areal of the ultrasonic impedance value Z from the gradual increase start point is equal to or higher than a reference increment σ. In the example shown in FIG. 20, at a time point when an increment σ8real of the ultrasonic impedance value Z from the elapsed time t8 which is the gradual increase start point reaches a reference increment σ8, a tentative minimal value Z8 is judged to be the minimal value. Moreover, the comparison of the ultrasonic impedance value Z relative to the tentative minimal value and the judgment on the minimal value may be carried out based on, e.g., whether the ultrasonic impedance value Z becomes a reference value Zth or more after the gradual increase start point. In this case, in the example shown in FIG. 20, after the elapsed time t8 which is the gradual increase start point, the tentative minimal value Z8 is judged to be the minimal value at the time point when the ultrasonic impedance value reaches a reference value Z8th.

When the tentative minimal value is judged to be the minimal value, the minimal value is detected. In the example shown in FIG. 20, the ultrasonic impedance value Z8 is detected as the minimal value. Additionally, an elapsed time t9 after the elapsed time t8 is a minimal detection point at which the minimal value Z8 is detected. Further, the reference increment σ and the reference value Zth are parameters for use in a judgment upon whether the detection disallowing state is switched to the detection allowing state by the control section 51. The reference increment σ and the reference value Zth are not set to specified magnitudes, and they may be set in accordance with changes with time or the like of the ultrasonic impedance value Z.

In the ultrasonic treatment apparatus 1 according to this embodiment, even if the ultrasonic impedance value Z is gradually decreased due to the adjustment of the frequency f before the target peak caused by the cut-and-divided, the peak detecting section is in the detection disallowing state (a non-detection state) where the detection of the target peak (detection processing) is not executed until the minimal detection point (e.g., t9) at which the minimal value (e.g., Z8) is first detected after the adjustment start point (e.g., t7). Thus, even if the ultrasonic impedance value Z is gradually decreased before the target peak caused due to the cut-and-divided, the target peak can be appropriately detected, i.e., determined.

Modification of Second Embodiment

As a modification of the second embodiment, a second modification will now be described with reference to FIG. 22 and FIG. 23. It is to be noted that like reference numerals denote parts equal to those in the second embodiment to omit a description thereof.

In this modification, like the second embodiment, the control unit 3 includes the electric power source 26, the control section 51, the impedance detecting section 52, the peak detecting section 53, the notifying section 59, and the frequency adjusting section 63. However, in this modification, the control unit 3 is not provided with the minimal value detecting section 65.

Figure 22:
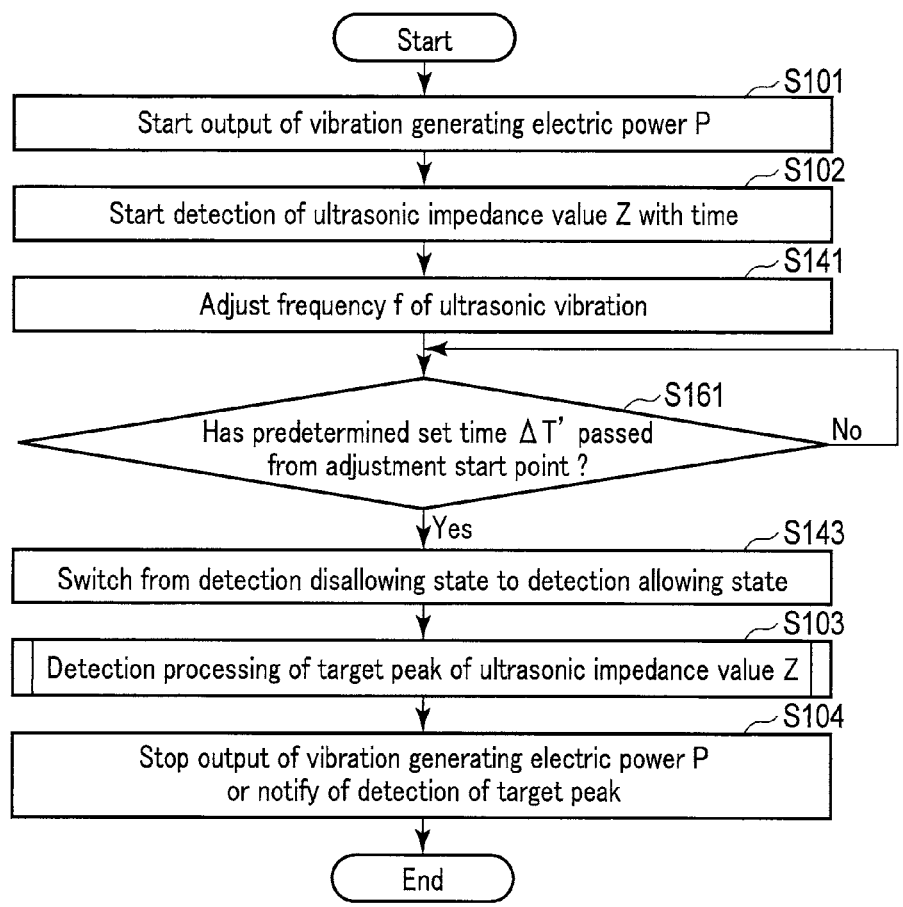
FIG. 22 is a flowchart showing an actuating state of a control unit from an output start of a vibration generating electric power according to a second modification.

FIG. 22 is a view showing an actuating state of the control unit 3 from an output start of the vibration generating electric power P in this modification. As shown in FIG. 22, in this modification, like the second embodiment, output of the vibration generating electric power P from the electric power source 26 is started in a step S101, and detection of the ultrasonic impedance value Z of the vibration generating electric power P with time is started in a step S102. Further, after the output start of the vibration generating electric power P from the electric power source 26, adjustment of the frequency f of the ultrasonic vibration is carried out by the frequency adjusting section 63 (a step S141). The adjustment of the frequency f is carried out in the same manner as the second embodiment.

Figure 23:
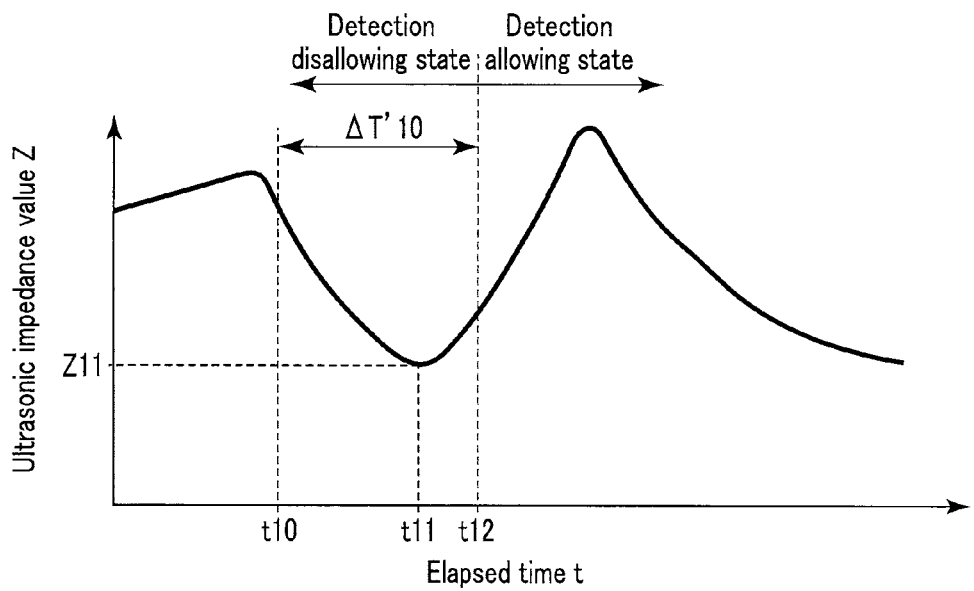
FIG. 23 is a schematic view showing an example of changes with time of an ultrasonic impedance value from an output start of the vibration generating electric power from an electric power source according to the second modification.

FIG. 23 is a view showing an example of changes with time of the ultrasonic impedance value Z in this modification. In FIG. 23, an axis of ordinate represents the ultrasonic impedance value Z, and an axis of abscissa represents the elapsed time t from an output start of the vibration generating electric power P. In this modification, like the second embodiment, since the adjustment of the frequency f of the ultrasonic vibration is performed, the ultrasonic impedance value Z is gradually decreased due to the adjustment of the frequency f before a target peak caused due to the cut-and-divided. Furthermore, in the vicinity of a time point when the frequency f is adjusted to the resonance frequency f0, the ultrasonic impedance value Z becomes a minimal value. In the example shown in FIG. 23, at an elapsed time t10, the adjustment of the frequency f of the ultrasonic vibration is started. Moreover, at an elapsed time t11, the ultrasonic impedance value Z becomes a minimal value Z11. That is, in the example shown in FIG. 23, the elapsed time t10 is an adjustment start point, and the elapsed time t11 is a minimal point.

However, in this modification, as different from the second embodiment, since the minimal value detecting section 65 is not provided, the detection processing (the step S142 in FIG. 18) of the minimal value of the ultrasonic impedance value Z is not executed. Instead, as show in FIG. 22, whether a predetermined set time ΔT' has passed from the adjustment start point at which the adjustment of the frequency f of the ultrasonic vibration is started is judged by the control section 51 (a step S161).

Additionally, when the predetermined set time ΔT' has passed from the adjustment start point (the step S161—Yes), the detection disallowing state where the detection of the target peak is not executed is switched to the detection allowing state where the detection of the target peak is executed (a step S143). Here, assuming that a time point at which the predetermined set time ΔT' passed from the adjustment start point is a startup point, the control section 51 switches the detection disallowing state where the detection of the target peak is not executed to the detection allowing state where the detection of the target peak is executed at the startup point (the step S143). That is, the control section 51 maintains the detection disallowing state until the startup point. Upon switching to the detection allowing state, like the second embodiment, the detection of the target peak caused due to the cut-and-divided is executed (a step S103). That is, the peak detecting section 53 (the gradual decrease detecting section 55, the tentative peak value holding section 56, and the peak judging section 57) is controlled to the state where the detection of the target peak is not executed until the startup point. In the example shown in FIG. 23, an elapsed time t12 after the elapsed time t11 is the startup point. Thus, a predetermined set time ΔT'10 is longer than a length from the elapsed time t10 which is the adjustment start point to the elapsed time t11 which is the minimal point. Here, the predetermined set time ΔT' is a parameter for use in a judgment upon whether the detection disallowing state is switched to the detection allowing state by the control section 51. The predetermined set time ΔT' is not set to a specified magnitude, and it may be set in accordance with changes with time or the like of the ultrasonic impedance value Z.

In the ultrasonic treatment apparatus 1 according to this modification, even if the ultrasonic impedance value Z is gradually decreased due to the adjustment of the frequency f before the target peak caused by the cut-and-divided, the detection disallowing state where the detection of the target peak (the detection processing) is not executed is provided until the startup point (e.g., t12) at which the predetermined set time ΔT' passed from the adjustment start point (e.g., t10). Furthermore, the predetermined set time ΔT' is longer than a length from the adjustment start point (e.g., t10) to the minimal point (e.g., t11). Thus, like the second embodiment, even if the ultrasonic impedance value Z is gradually decreased before the target peak caused by the cut-and-divided, the target peak can be appropriately detected.

Moreover, as a modification of the second embodiment, a third modification will now be described with reference to FIG. 24 and FIG. 25. It is to be noted that like reference numerals denote parts equal to those in the second embodiment to omit a description thereof.

In this modification, like the second embodiment, the control unit 3 includes the electric power source 26, the control section 51, the impedance detecting section 52, the peak detecting section 53, the notifying section 59, and the frequency adjusting section 63. However, in this modification, the control unit 3 is not provided with the minimal value detecting section 65. Moreover, in this modification, the impedance detecting section 52 detects the frequency f of the ultrasonic vibration with time.

Figure 24:
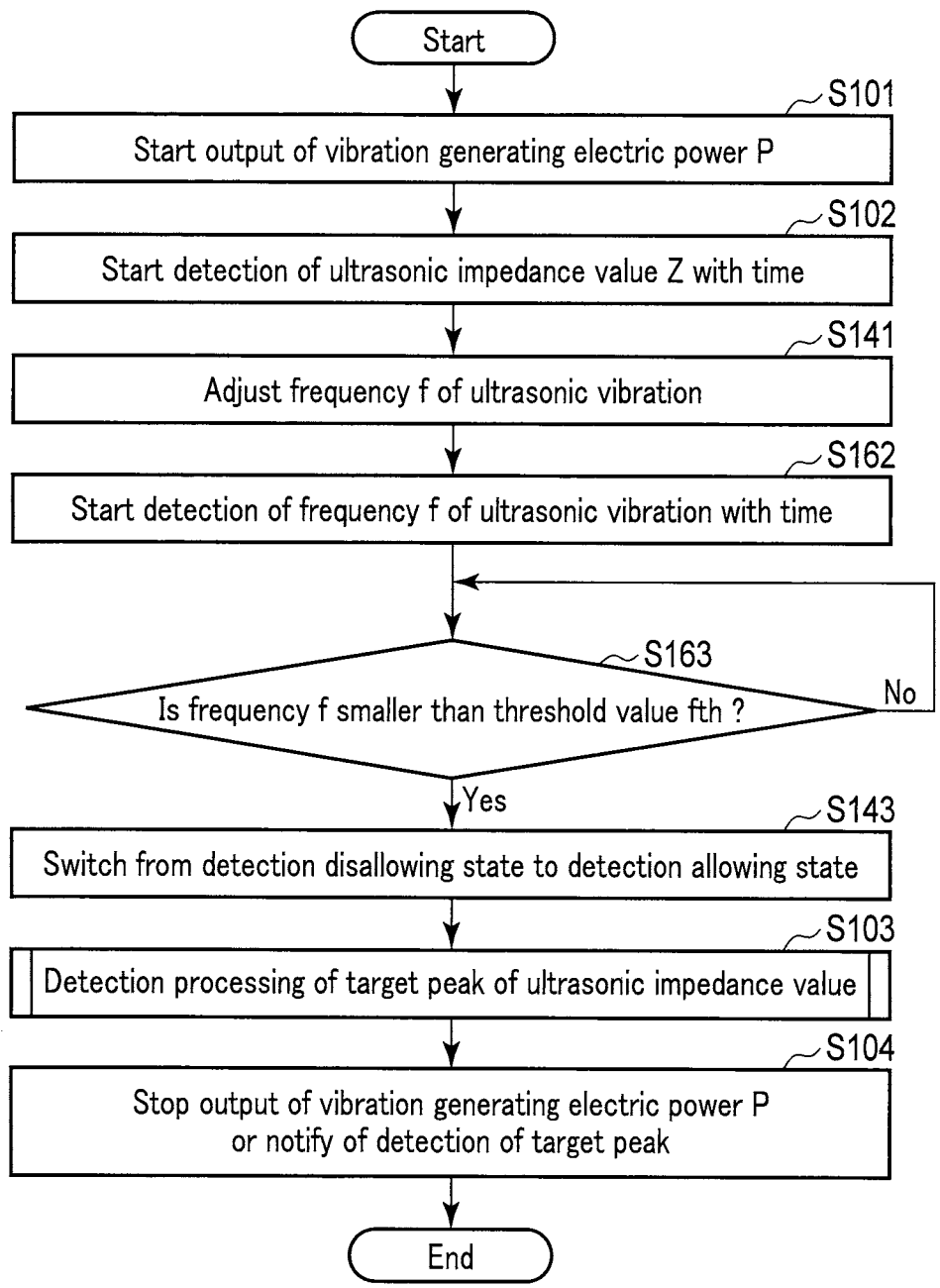
FIG. 24 is a flowchart showing an actuating state of a control unit from an output start of a vibration generating electric power according to a third modification.

FIG. 24 is a view showing an actuating state of the control unit 3 from an output start of the vibration generating electric power P. As shown in FIG. 24, in this modification, like the second embodiment, output of the vibration generating electric power P from the electric power source 26 is started in a step S101, and detection of the ultrasonic impedance value Z of the vibration generating electric power P with time is started in a step S102. Additionally, after an output start of the vibration generating electric power P from the electric power source 26, adjustment of the frequency f of the ultrasonic vibration is performed by the frequency adjusting section 63 (a step S141). The adjustment of the frequency f is performed in the same manner as the second embodiment.

Further, in this modification, the impedance detecting section 52 starts detecting the frequency f of the ultrasonic vibration with time (a step S162). The impedance detecting section 52 detects changes with time of a vibration generating current I and a vibration generating voltage V. Furthermore, the frequency f of the ultrasonic vibration is detected based on a phase difference or the like of the vibration generating current I and the vibration generating voltage V.

FIG. 25 is a view showing an example of changes with time of the ultrasonic impedance value Z and changes with time of the frequency f of the ultrasonic vibration in this modification. In FIG. 25, an axis of ordinate represents the ultrasonic impedance value Z and the frequency f, and an axis of abscissa represents the elapsed time t from an output start of the vibration generating electric power P.

Further, a solid line indicates changes with time of the ultrasonic impedance value Z, and an alternate long and short dash line indicates changes with time of the frequency f. In this modification, like the second embodiment, since the frequency f of the ultrasonic vibration is adjusted, the ultrasonic impedance value Z gradually decreases due to the adjustment of the frequency f before a target peak caused by the cut-and-divided.

However, in this modification, as different from the second embodiment, since the minimal value detecting section 65 is not provided, the detection processing (the step S142 in FIG. 18) of a minimal value of the ultrasonic impedance value Z is not executed. Instead, as shown in FIG. 24, after an adjustment start of the frequency f of the ultrasonic vibration, whether the frequency f of the ultrasonic vibration is smaller than a threshold value fth is judged by the control section 51 (a step S163). When the vibration generating electric power P is supplied to the ultrasonic transducer (the vibration generating section) 22 and the ultrasonic vibration is produced, a temperature of the ultrasonic vibrator 22 increases. When the temperature of the ultrasonic transducer 22 increases, the frequency (a resonance frequency) f of the ultrasonic vibration decreases. Thus, when the treated target is cut-and-divided by the ultrasonic vibration, the temperature of the ultrasonic transducer increases, and the frequency f of the ultrasonic vibration decreases.

Thus, in this modification, when the frequency f of the ultrasonic vibration is smaller than the threshold value fth (the step S163—Yes), the detection disallowing state where the detection of the target peak is not executed is switched to the detection allowing state where the detection of the target peak is executed (a step S143). In this modification, the control section 51 switches the detection disallowing state where the detection of the target peak is not executed to the detection allowing state where the detection of the target peak is executed at a time point when the frequency f falls below the threshold value fth (the step S143). That is, the control section 51 maintains the detection disallowing state until the frequency f of the ultrasonic vibration falls below the threshold value fth. When the state is switched to the detection allowing state, like the second embodiment, the detection of the target peak caused by the cut-and-divided is executed (a step S103). That is, the peak detecting section 53 (the gradual decrease detecting section 55, the tentative peak value holding section 56, and the peak judging section 57) is controlled to a state where the detection of the target peak is not executed until the frequency f falls below the threshold value fth.

In the example shown in FIG. 25, at an elapsed time t13, the frequency f falls below a threshold value f13th. Consequently, the detection disallowing state is switched to the detection allowing state. When the state is switched to the detection allowing state, the ultrasonic impedance Z14 at an elapsed time t14 is detected as the target peak caused by the cut-and-divided. Here, the threshold value fth of the frequency f is a parameter for use in a judgment upon whether the detection disallowing state is switched to the detection allowing state by the control section 51. The threshold value fth is not set to a specified magnitude, and it may be set in accordance with changes with time or the like of the ultrasonic impedance value Z.

In the ultrasonic treatment apparatus 1 according to this modification, even if the ultrasonic impedance value Z is gradually decreased due to the adjustment of the frequency f before the target peak caused by the cut-and-divided, the detection disallowing state where the detection of the target peak (the detection processing) is executed is provided until the frequency f falls below the threshold value fth. Thus, like the second embodiment, even if the ultrasonic impedance value Z is gradually decreased before the target peak caused by the cutoff, the target peak can be appropriately detected.

It is to be noted that, as another modification, the detection processing of a minimal value and the switching at the minimal detection point in the second embodiment may be applied to the control unit 3 of the ultrasonic treatment apparatus 1 according to the first modification. Furthermore, the switching at the startup point in the second modification may be applied to the control unit 3 of the ultrasonic treatment apparatus 1 according to the first modification. Moreover, the switching of the detection allowing state based on the frequency f in the third modification may be applied to the control unit 3 of the ultrasonic treatment apparatus 1 according to the first modification.

Modification of First Embodiment and Second Embodiment

As a modification of the first embodiment and the second embodiment, a fourth modification will now be described with reference to FIG. 26 to FIG. 28. It is to be noted that like reference numerals denote parts equal to those in the first embodiment and the second embodiment to omit a description thereof.

FIG. 26 is a view showing an electrical connection state of the ultrasonic treatment instrument, the transducer unit 5, and the control unit 3. As shown in FIG. 26, in this modification, like the second embodiment, the control unit 3 includes the electric power source 26, the control section 51, the impedance detecting section 52, the peak detecting section 53, the notifying section 59, the frequency adjusting section 63, and the minimal value detecting section 65. However, in this modification, the control unit 3 is provided with an output adjusting section 77 formed of a touch panel or the like. In the output adjusting section 77, an operation of adjusting a magnitude (an output level) of the vibration generating current I output from the electric power source 26 is input. It is to be noted that the control section 51 controls an output state of the vibration generating electric power P by constant-current control to maintain the vibration generating current I constant at the output level adjusted by the output adjusting section 77. In this modification, the impedance detecting section 52 detects the magnitude (the output level) of the vibration generating current I with time.

Further, in this modification, an information memory section (a probe information memory section) 71 which is a nonvolatile memory such as an ROM is provided inside the handle unit 6. The information memory section 71 is fixed to, e.g., the tubular case portion 11 of the handle unit 6. The information memory section 71 stores at least information concerning a type of the ultrasonic probe 9. For example, the information memory section 71 stores an identification number indicative of a type of the ultrasonic probe 9. It is to be noted that the information memory section 71 may store information concerning the ultrasonic treatment instrument 2 (the handle unit 6 or the like) including the ultrasonic probe 9. When the transducer unit 5 is coupled with the handle unit 6 and the cable 7 is connected to the control unit 3, the information memory section 71 is electrically connected to the control section 51 of the control unit 3 through a signal path 72. The signal path portion 72 is extended through the inside of the handle unit 6, the inside of the transducer case 21, and the inside of the cable 7.

Furthermore, in this modification, an information memory section (a transducer information memory section) 73 that is a nonvolatile memory such as an ROM is provided inside the transducer case 21. The information memory section 73 is fixed to, e.g., the vibrator case 21. The information memory section 73 stores at least information concerning a type of the ultrasonic transducer (the vibration generating section) 22. For example, the information memory section 73 stores an identification number indicative of a type of the ultrasonic transducer 22. It is to be noted that the information memory section 73 stores information concerning the transducer unit 5 (the horn member 23 or the like) including the ultrasonic transducer 22. When the vibrator unit 5 is coupled with the handle unit 6 and the cable 7 is connected to the control unit 3, the information memory section 73 is electrically connected to the control section 51 of the control unit 3 through a signal path 75. The signal path portion 75 is extended through the inside of the transducer case 21 and the inside of the cable 7.

The control section 51 of the control unit 3 includes an identifying section 76. The identifying section 76 is formed of, e.g., an electronic circuit of a processor. The identifying section 76 reads information stored in the information memory section 71 through the signal path portion 72. Moreover, based on the information read from the information memory section 71, a type of the ultrasonic probe 9 coupled with the ultrasonic transducer 22 is identified. When the type of the ultrasonic probe 9 is identified, a shape, a dimension, and others of the ultrasonic probe 9 are also detected. Additionally, the identifying section 76 reads information stored in the information memory section 73 through the signal path portion 75. Further, based on the information read from the information memory section 73, a type of the ultrasonic transducer 22 to which the vibration generating electric power P is supplied from the electric power source 26 is identified. It is to be noted that the identifying section 76 may be a separated body from the control section 51.

Figure 27:
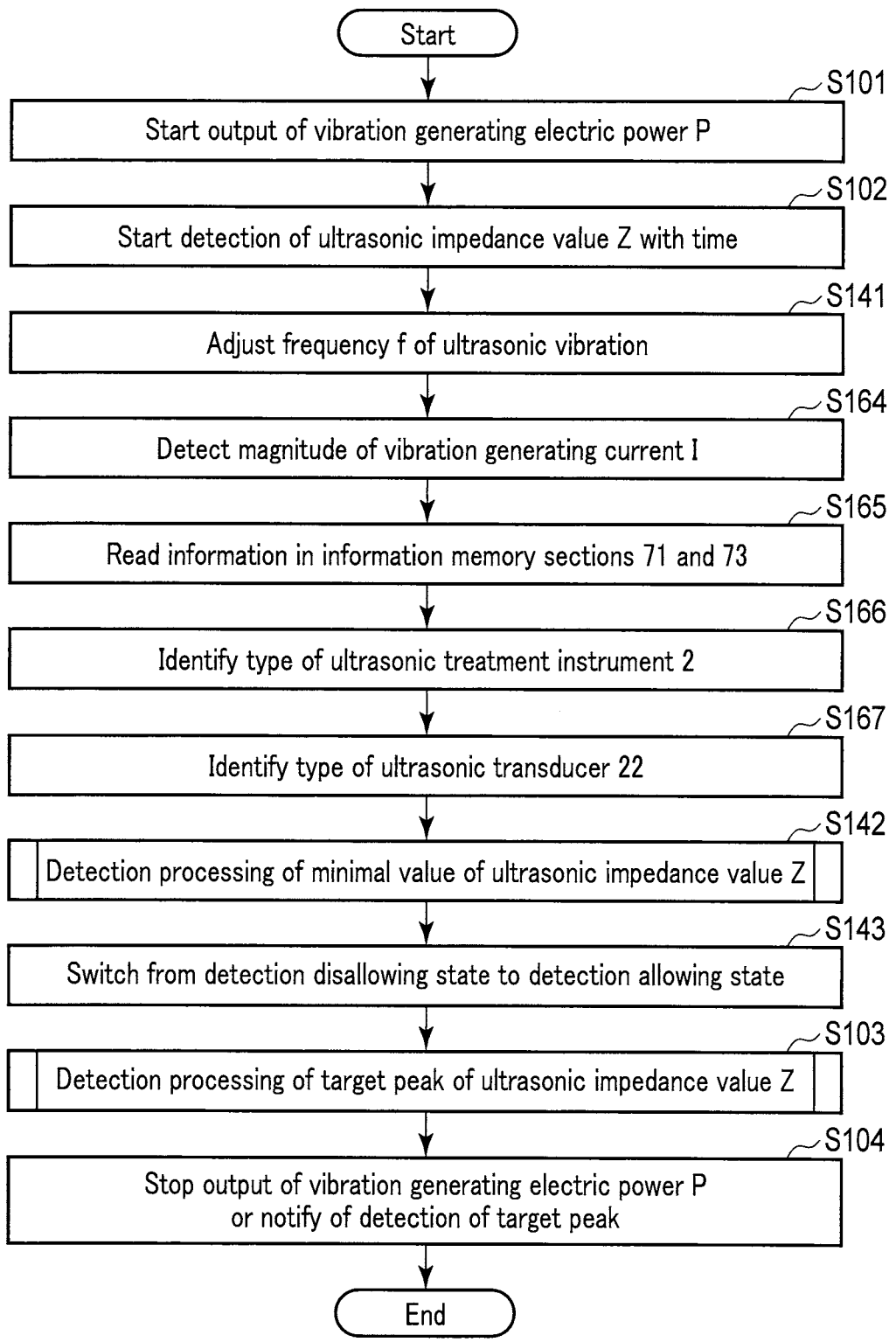
FIG. 27 is a flowchart showing an actuating state of a control unit from an output start of a vibration generating electric power according to the fourth modification.

FIG. 27 is a view showing an actuating state of the control unit 3 from an output start of the vibration generating electric power P in this modification. As shown in FIG. 27, in this modification, like the second embodiment, output of the vibration generating electric power P from the electric power source 26 is started in a step S101, and detection of the ultrasonic impedance value Z of the vibration generating electric power P with time is started in a step S102. Furthermore, after the output start of the vibration generating electric power P from the electric power source 26, the frequency f of the ultrasonic vibration is adjusted by the frequency adjusting section 63 (a step S141). The adjustment of the frequency f is carried out in the same manner as the second embodiment.

In this modification, the impedance detecting section 52 detects a magnitude of the vibration generating current I (a step S164). Consequently, an output level of the vibration generating current I adjusted by the output adjusting section 77 is detected. Moreover, the identifying section 76 reads information stored in the information memory section 71 and information stored in the information memory section 73 (a step S165). The identifying section 76 identifies a type of the ultrasonic treatment instrument 2 (the ultrasonic probe 9, the handle unit 6, and the like) based on the information read from the information memory section (the probe information memory section) 71 (a step S166). Consequently, a type of the ultrasonic probe 9 coupled with the ultrasonic transducer (the vibration generating section) 22 is identified, and a dimension, (a length in a direction parallel to the longitudinal axis), a shape, and others of the ultrasonic probe are detected. Additionally, the identifying section 76 identifies a type of the ultrasonic transducer 22 based on the information read from the information memory section (the transducer information memory section) 73 (a step S167).

Further, like the second embodiment, when the minimal value detecting section 65 executes the detection processing of a minimal value of the ultrasonic impedance value Z (a step S142) and the minimal value of the ultrasonic impedance Z is detected, the control section 51 switches the detection disallowing state to the detection allowing state where a detection of a target peak is executed (a step S143). When the state is switched to the detection allowing state, the peak detecting section 53 executes the detection processing of the target peak of the ultrasonic impedance value Z (a step S103), and output of the vibration generating electric power P is stopped or detection of the target peak is notified upon detecting the target peak (a step S104).

In the detection processing of the minimal value (the step S142), the reference increment a, the reference value Zth, and others described in the second embodiment are set based on an identification result of a type of the ultrasonic treatment instrument 2 (the ultrasonic probe 9) and an identification result of a type of the ultrasonic transducer 22. Furthermore, in the detection processing of the minimal value (the step S142), the reference increment σ, the reference value Zth, and others are set based on a detection result of a magnitude (an output level) of the vibration generating current I. That is, the control section 51 sets a parameter for use in a judgment upon whether the detection disallowing state is switched to the detection allowing state based on identification results of a type of the ultrasonic treatment instrument 2 (the ultrasonic probe 9) and a type of the ultrasonic transducer 22 provided by the identifying section 76 and a detection result of an output level of the vibration generating current I provided by the impedance detecting section 52.

In the detection processing of the target peak (the step S103), the reference increment ε, the reference time ΔT, and others described in the first embodiment are set based on an identification result of a type of the ultrasonic treatment instrument 2 (the ultrasonic probe 9) and an identification result of a type of the ultrasonic transducer 22. Moreover, in the detection processing of the target peak (the step S103), the reference decrement ε, the reference time ΔT, and others are set based on a detection result of a magnitude (an output level) of the vibration generating current I. That is, the peak judging section 57 sets a parameter for use in a judgment upon whether a tentative peak value is a target peak based on identification results of a type of the ultrasonic treatment instrument 2 (the ultrasonic probe 9) and a type of the ultrasonic transducer 22 provided by the identifying section 76 and a detection result of an output level of the vibration generating current I provided by the impedance detecting section 52.

The memory section forming a part of the control section 51, the peak detecting section 53, and the minimal value detecting section 65 stores a table showing set values of parameters for a type of the ultrasonic treatment instrument 2, a type of the ultrasonic transducer 22, and an output level of the vibration generating current I. FIG. 28 is a view showing an example of a table stored in the memory section of the control unit 3. FIG. 28 is a table showing set values of parameters when the vibration generating current I is output on an output level 1. As shown in FIG. 28, when the vibration generating current I is on the output level 1, for example, set values of the parameters are stored in a case where a type of the ultrasonic treatment instrument 2 (the ultrasonic probe 9) is Type J1 to J3 and a case where the information memory section 71 is not provided in the ultrasonic treatment tool 2, respectively. Further, when the vibration generating current I is on the output level 1, for example, set values of the parameters are stored in a case where a type of the ultrasonic transducer 22 is Type K1 to K3 and a case where the information memory section 73 is not provided in the transducer unit 5. Thus, when the vibration generating current I is on the output level 1, set values L1 to L16 are stored in accordance with a type of the ultrasonic treatment instrument 2 and a type of the ultrasonic transducer 22. When the vibration generating current I is on an output level other than the output level 1, there is the same table showing set values of the parameters as that in FIG. 28, and the parameters according to this output level are stored.

The peak judging section 57 sets parameters (the reference decrement s and the reference time ΔT) for use in a judgment upon whether a tentative peak value is a target peak to set values L corresponding to identification results of a type of the ultrasonic treatment instrument 2 (the ultrasonic probe 9) and a type of the ultrasonic transducer 22 provided by the identifying section 76 and a detection result of an output level of the vibration generating current I provided by the impedance detecting section 52 based on the stored table. Likewise, the control section 51 sets parameters (the reference increment a and the reference value Zth) for use in a judgment upon whether the detection disallowing state is switched to the detection allowing state to set values L corresponding to identification results L of a type of the ultrasonic treatment tool 2 (the ultrasonic probe 9) and a type of the ultrasonic vibrator 22 provided by the identifying section 76 and a detection result of an output level of the vibration generating current I provided by the impedance detecting section 52 based on the stored table. Consequently, a target peak is appropriately detected, and the detection disallowing state is appropriately switched to the detection allowing state in accordance with a type of the ultrasonic probe 9, a type of the ultrasonic transducer 22, and an output level of the vibration generating current I.

It is to be noted that the parameters for use in the judgment upon whether the tentative peak value is the target peak in the first modification which is a modification of the first embodiment may be set like the fourth modification. In this case, the peak judging section 57 sets the reference decrement ϵ, the reference time ΔT, and the reference increment ξ based on identification results of a type of the ultrasonic treatment instrument 2 (the ultrasonic probe 9) and a type of the ultrasonic transducer 22 provided by the identifying section 76 and a detection result of an output level of the vibration generating current I provided by the impedance detecting section 52. Further, the parameters for use in the judgment upon whether the detection disallowing state is switched to the detection allowing state in each of the second modification and the third modification that are the modifications of the second embodiment may be set like the fourth modification. In this case, the control section 51 sets the predetermined set time ΔT' or sets the threshold value fth of the frequency f based on identification results of a type of the ultrasonic treatment instrument 2 (the ultrasonic probe 9) and a type of the ultrasonic transducer 22 provided by the identifying section 76 and a detection result of an output level of the vibration generating current I provided by the impedance detecting section 52.

Furthermore, in a given modification, the parameters for use in the judgment upon whether a tentative peak value is a target peak may be set based on at least one of an identification result of a type of the ultrasonic treatment instrument 2 (the ultrasonic probe 9), an identification result of a type of the ultrasonic transducer 22, and a detection result of an output level of the vibration generating current I provided by the impedance detecting section 52. Likewise, in a given modification, the parameters for use in the judgment upon whether the detection disallowing state is switched to the detection allowing state may be set based on at least one of an identification result of a type of the ultrasonic treatment instrument 2 (the ultrasonic probe 9), an identification result of a type of the ultrasonic transducer 22, and a detection result of an output level of the vibration generating current I provided by the impedance detecting section 52.

Moreover, as a modification of the first embodiment and the second embodiment, a fifth modification will now be described with reference to FIG. 29 and FIG. 30. It is to be noted that like reference numerals denote parts equal to those in the first embodiment and the second embodiment to omit a description thereof.

FIG. 29 is a view showing an electrical connection state of the transducer unit 5 and the control unit 3 according to this modification. As shown in FIG. 29, in this modification, like the second embodiment, the control unit 3 includes the electric power source 26, the control section 51, the impedance detecting section 52, the peak detecting section 53, the notifying section 59, the frequency adjusting section 63, and the minimal value detecting section 65.

In this modification, an information memory section (a number-of-times memory section) 81 that is a nonvolatile memory such as an ROM is provided in the transducer case 21. The information memory section 81 is fixed to, e.g., the transducer case 21. The information memory section 81 stores, for example, at least the number of times N of a heat sterilization processing (e.g., autoclave sterilization) executed in the transducer unit 5 including the ultrasonic transducer (the vibration generating section) 22. The vibrator unit 5 is coupled with the handle unit 6, and the cable 7 is connected to the control unit 3, thereby electrically connecting the information memory section 81 to the control section 51 of the control unit 3 through a signal path 82. The signal path portion 82 is extended through the inside of the transducer case 21 and the inside of the cable 7.

The control section 51 of the control unit 3 includes a number-of-times update section 83. When the heat sterilization processing was performed in the ultrasonic transducer 22, the number-of-times update section 83 adds 1 to the number of times N stored in the information memory section 81, and updates the number of times N of the executed heat sterilization treatment. It is to be noted that a configuration and a method of updating the number of times N of execution of the heat sterilization treatment stored in the information memory section 81 is described in Reference Literature 1 (International Publication No. 2014/125983) in detail, and the number of times N is updated in the same manner in this modification. Thus, a detailed description of the configuration and the method of updating the number of times N of execution of the heat sterilization processing will be omitted. Moreover, the identifying section 76 may be separated body from the control section 51.

Figure 30:
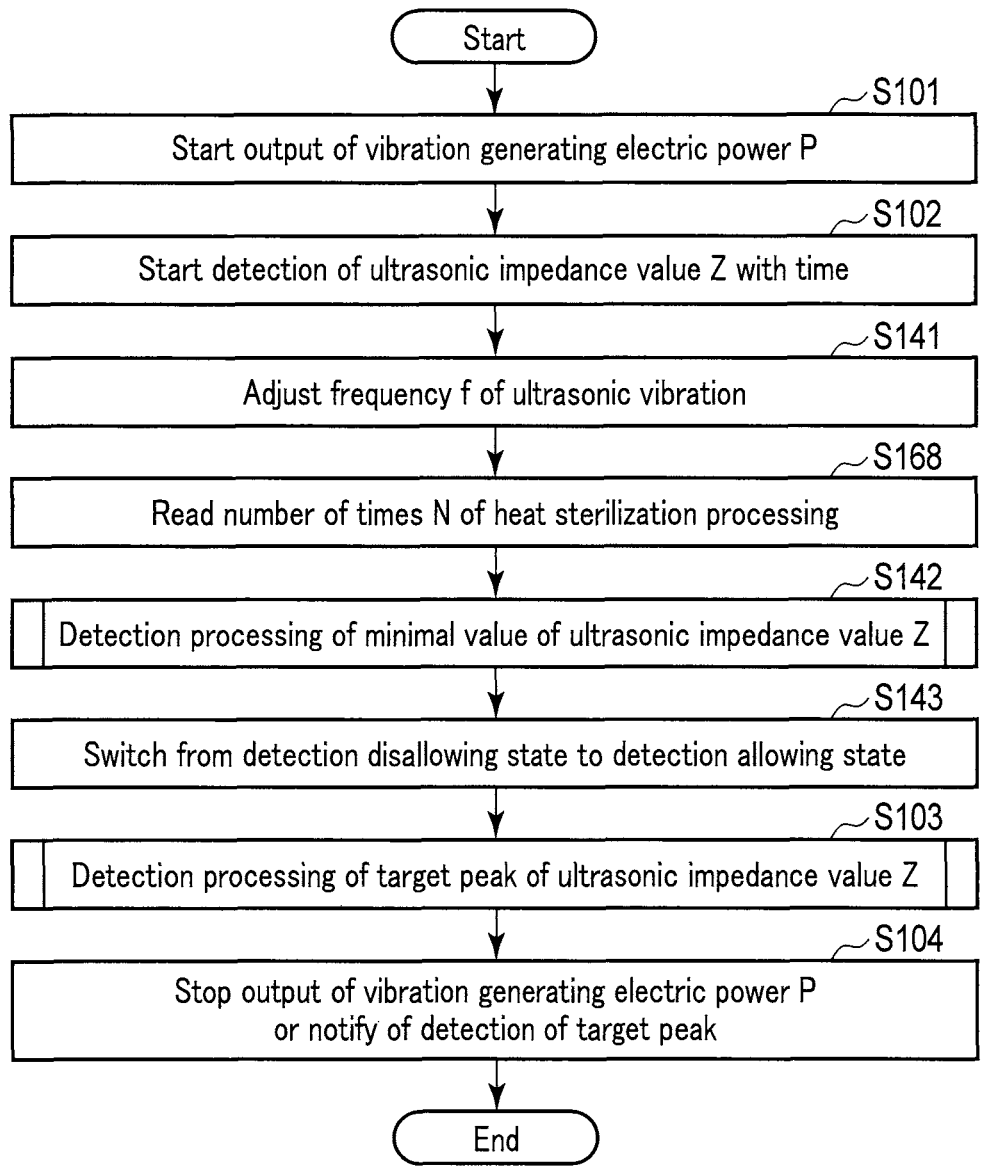
FIG. 30 is a flowchart showing an actuating state of the control unit from an output start of a vibration generating electric power according to the fifth modification.

FIG. 30 is a view showing an actuating state of the control unit 3 from an output start of the vibration generating electric power P in this modification. As shown in FIG. 30, in this modification, like the second embodiment, output of the vibration generating electric power P from the electric power source 26 is started in a step S101, and detection of the ultrasonic impedance value Z of the vibration generating electric power P with time is started in a step S102. Further, after an output start of the vibration generating electric power P from the electric power source 26, the frequency f of the ultrasonic vibration is adjusted by the frequency adjusting section 63 (a step S141). The adjustment of the frequency f is performed in the same manner as the second embodiment.

In this modification, the control section 51 reads the number of times of execution of the heat sterilization processing stored in the information memory section 81 (a step S168). Furthermore, like the second embodiment, the minimal value detecting section 65 executes the detection processing of a minimal value of the ultrasonic impedance value Z (a step S142), and the control section 51 switches the detection disallowing state to the detection allowing state where the detection of a target peak is executed upon detecting the minimal value of the ultrasonic impedance Z (a step S143). Moreover, when the state is switched to the detection allowing state, the peak detecting section 53 executes the detection processing of a target peak of the ultrasonic impedance value Z (a step S103), and output of the vibration generating electric power P is stopped or the detection of the target peak is notified upon detecting the target peak (a step S104).

In the detection processing of the minimal value (the step S142), based on the number of times N of execution of the heat sterilization processing stored in the information memory section 81, the reference increment σ, the reference value Zth, and others described in the second embodiment are set. That is, the control section 51 sets parameters for use in a judgment upon whether the detection disallowing state is switched to the detection allowing state based on the number of times N of the execution of the heat sterilization processing. In the detection processing of a target peak (the step S103), based on the number of times N of execution of the heat sterilization treatment stored in the information memory section 81, the reference increment $\epsilon$, the reference time $\Delta T$, and others described in the first embodiment are set. That is, the peak judging section 57 sets parameters for use in a judgment upon whether a tentative peak value is a target peak based on the number of times N of the execution of the heat sterilization processing stored in the information memory section 81.

The memory section forming a part of the control section 51, the peak detecting section 53, and the minimal value detecting section 65 stores a table showing set values of parameters for the number of times N of the heat sterilization treatment. The peak judging section 57 sets the parameters (the reference decrement $\epsilon$ and the reference time $\Delta T$) for use in the judgment upon whether the tentative peak value is the target peak to set values corresponding to the number of times N of execution of the heat sterilization processing stored in the information memory section 81 based on the stored table. Likewise, the control section 51 sets the parameters (the reference increment a and the reference value Zth) for use in the judgment upon whether the detection disallowing state is switched to the detection allowing state to set values L corresponding to the number of times N of execution of the heat sterilization processing stored in the information memory section 81 based on the stored table. Consequently, the target peak is appropriately detected, and the detection disallowing state is appropriately switched to the detection allowing state in accordance with the number of times N of the heat sterilization processing executed in the ultrasonic transducer 22, i.e., how the ultrasonic transducer has been deteriorated since manufacture.

It is to be noted that the parameters for use in the judgment upon whether the tentative peak value is the target peak in the first modification that is the modification of the first embodiment may be set in the same manner as the fifth modification. In this case, the peak judging section 57 sets the reference decrement $\epsilon$, the reference time $\Delta T$, and the reference increment $\xi$ based on the number of times N of execution of the heat sterilization processing stored in the information memory section 81. Additionally, the parameters for use in the judgment upon whether the detection disallowing state is switched to the detection allowing state in each of the second modification and the third modification that are the modifications of the second embodiment may be set in the same manner as the fifth embodiment. In this case, the control section sets the predetermined set time $\Delta T'$ based on the number of times N of execution of the heat sterilization processing stored in the information memory section 81. Alternatively, the threshold value fth of the frequency f is set.

Further, in a given modification, the parameters for use in the judgment upon whether the tentative peak value is the target peak may be set based on the number of times N of execution of the heat sterilization processing stored in the information memory section 81 in addition to at least one of an identification result of a type of the ultrasonic treatment instrument 2 (the ultrasonic probe 9), an identification result of a type of the ultrasonic transducer 22, and a detection result of an output level of the vibration generating current I provided by the impedance detecting section 52. Likewise, in a given modification, the parameters for use in the judgment upon whether the detection disallowing state is switched to the detection allowing state may be set based on the number of times N of execution of the heat sterilization processing stored in the information memory section 81 in addition to at least one of an identification result of a type of the ultrasonic treatment instrument 2 (the ultrasonic probe 9), an identification result of a type of the ultrasonic transducer 22, and a detection result of an output level of the vibration generating current I provided by the impedance detecting section 52.

Third Embodiment

A third embodiment according to the present invention will now be described with reference to FIG. 31 to FIG. 35. The third embodiment is provided by modifying the configuration of the first embodiment as follows. It is to be noted that like reference numerals denote parts equal to those in the first embodiment to omit a description thereof.

In this embodiment, like the first embodiment, a control unit 3 includes an electric power source 26, a control section 51, an impedance detecting section 52, a peak detecting section 53, a switching operation section 58, and a notifying section 59. However, in this modification, the electric power source 26 can output a high-frequency electric power P' in addition to a vibration generating electric power P. In this embodiment, when an operation signal is transmitted to the control section 51 by input of an energy operation using an energy operation input button 16, output of the vibration generating electric power P from the electric power source 26 is started, and the high-frequency electric power P' is also output. It is to be noted that, in the electric power source 26, a portion that outputs the vibration generating electric power P and a portion that outputs the high-frequency electric power P' may be integrally provided, or they may be separately provided. Furthermore, in the electric power source 26, for example, electric power from, e.g., a receptacle outlet or a direct-current power source is converted into the vibration generating electric power P and the high-frequency electric power P' by a conversion circuit or the like, and the converted electric power is output.

Figure 31:
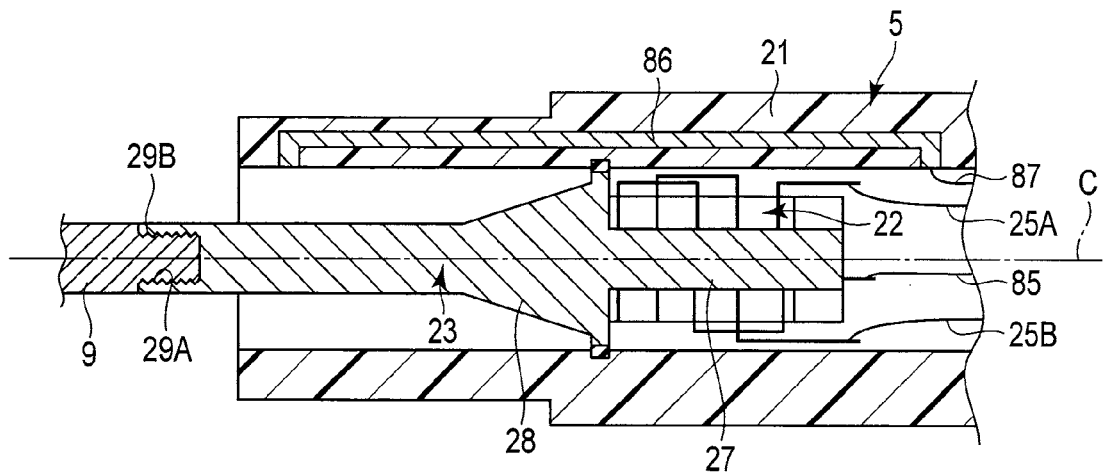
FIG. 31 is a longitudinal cross-sectional view schematically showing a configuration of a transducer unit according to a third embodiment.

FIG. 31 is a view showing a configuration of a transducer unit 5 according to this embodiment. As shown in FIG. 31, in this embodiment, one end of an electrical wiring 85 is connected to a horn member 23. The electrical wiring 85 is extended through the inside of a cable 7, and the other end thereof is connected to the electric power source 26. The high-frequency electric power P' output from the electric power source 26 is supplied to a treatment section 17 through the electrical wiring 85, the horn member 23, and an ultrasonic probe 9. When the high-frequency electric power P' is supplied to the treatment section 17, the treatment section 17 functions as an electrode.

Moreover, in this embodiment, a conductive portion 86 is provided to a transducer case 21. One end of an electrical wiring 87 is connected to the conductive portion 86. The electrical wiring 87 is extended through the inside of the cable 7, and the other end thereof is connected to the electric power source 26. The high-frequency electric power P' output from the electric power source 26 is supplied to a jaw 18 through the electrical wiring 87, the conductive portion 86 of the transducer case 21, a movable tubular portion (not shown) of a sheath 8. When the high-frequency electric power P' is supplied to the jaw 18, a grasp member 42 of the jaw 18 functions as an electrode having an electric potential different from that of the treatment section 17.

In a state where the high-frequency electric power P' is supplied to the treatment section 17 and the jaw 18, an electric potential of the treatment section 17 is different from an electric potential of the grip member 42. Thus, when the high-frequency electric power. P' is supplied to the treatment section 17 and the jaw 18 in a state where a treated target H is grasped between the treatment section 17 and the jaw 18, a high-frequency current I' flows through the treated target H. Here, an electric potential difference between the treatment section 17 and the grasp member 42 of the jaw 18 is a high-frequency voltage V'.

In this embodiment, in a state where the high-frequency electric power P' is output from the electric power source 26, the impedance detecting section 52 detects a high-frequency impedance value Z' of the high-frequency electric power P' with time. Thus, in this embodiment, the impedance detecting section 52 detects an ultrasonic impedance value Z with time, and also detects the high-frequency impedance value Z' with time. The high-frequency impedance value Z' is represented by Expression (2).

[Expression 2]

$$Z' = V'/I' = V^2/P' \quad (2)$$

Thus, detecting the high-frequency electric power P', the high-frequency voltage V', and the high-frequency current I' with time enables detecting changes with time of the high-frequency impedance value Z'. It is to be noted that, in the impedance detecting section 52, a portion that detects the ultrasonic impedance value Z and a portion that detects the high-frequency impedance value Z' may be integrally provided, or they may be separately provided.

Figure 32:
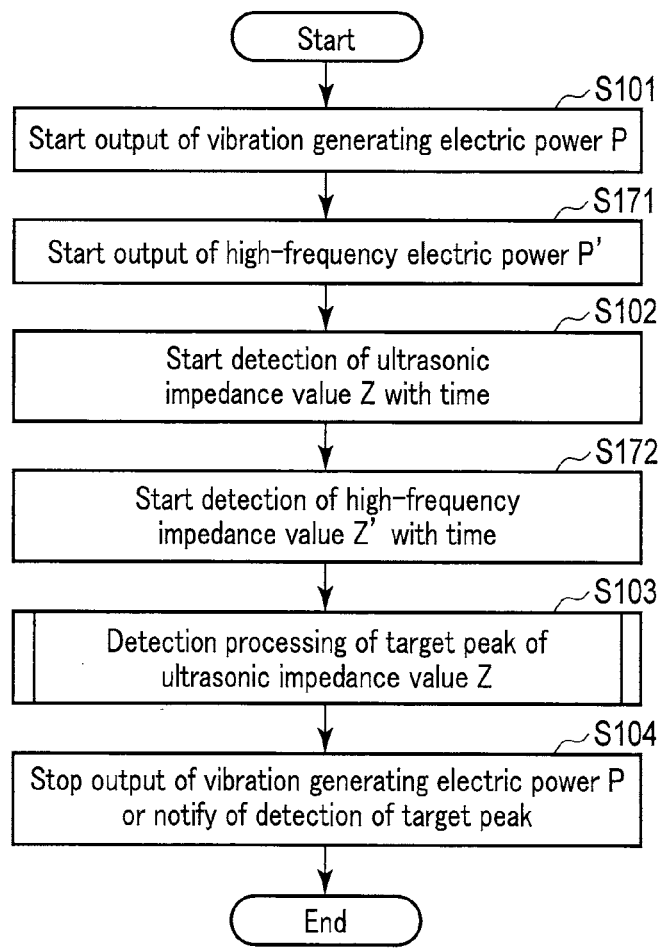
FIG. 32 is a flowchart showing an actuating state of a control unit from an output start of a vibration generating electric power according to the third embodiment.

FIG. 32 is a view showing an actuating state of the control unit 3 after an output start of the vibration generating electric power P in this embodiment. In this embodiment, output of the high-frequency electric power P' is started (as step S171) simultaneously with an output start of the vibration generating electric power P (a step S101). Further, the impedance detecting section 52 starts detection of the high-frequency impedance value Z' of the high-frequency electric power P' with time (a step S172) simultaneously with detection of the ultrasonic impedance value Z of the vibration generating electric power P with time (a step S102). Furthermore, in a step S103, detection processing of a target peak of the ultrasonic impedance value Z caused by cut-and-divided of the treated target H is performed. However, in this embodiment, the target peak is detected based on changes with time of the ultrasonic impedance value Z as well as changes with time of the high-frequency impedance value Z'.

In this embodiment, like the first embodiment, in detection of the target peak, a gradual decrease start point at which the ultrasonic impedance value Z starts to gradually decrease is detected in a step S111, and the ultrasonic impedance value Z at the detected gradual decrease start point is held as a tentative peak value (see FIG. 11). Moreover, changes with time of the ultrasonic impedance value Z after the gradual decrease start point are compared with the held tentative peak value in a step S113, and whether the tentative peak value is the target peak caused due to the cut-and-divided of the treated target H is judged in a step S114 (see FIG. 11). However, in this embodiment, the comparison processing of the changes with time of the ultrasonic impedance value relative to the tentative peak value and the judgment on whether it is the target peak are carried out based on the changes with time of the high-frequency impedance value Z' in addition to the changes with time of the ultrasonic impedance value Z.

Figure 33:
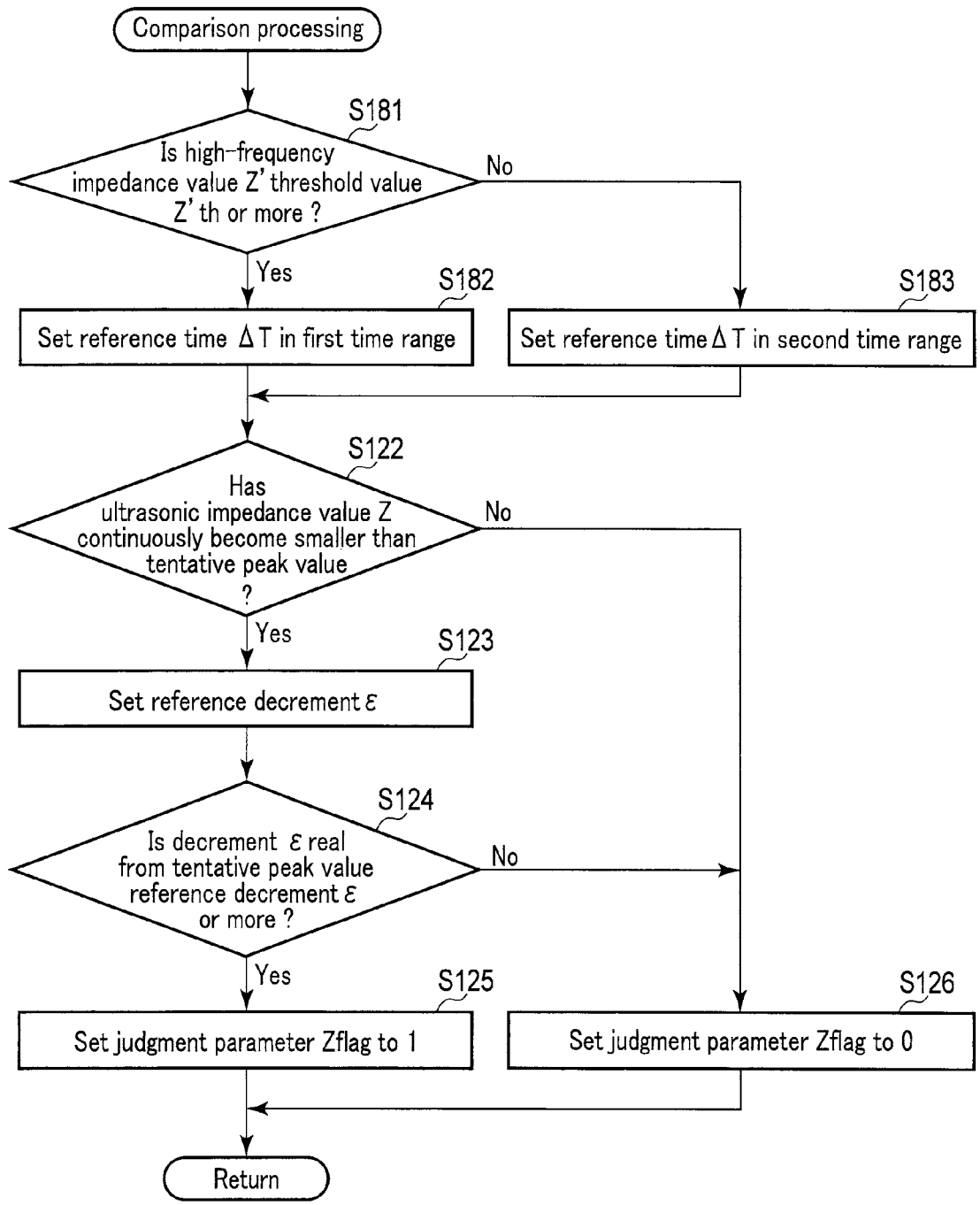
FIG. 33 is a flowchart showing comparison processing of changes with time of an ultrasonic impedance value relative to a tentative peak value executed by a peak judging section according to the third embodiment.

FIG. 33 is a view showing comparison processing of changes with time of the ultrasonic impedance value Z after the gradual decrease start point relative to the tentative peak value carried out by the peak judging section 57 (the step S113 in FIG. 11). That is, FIG. 33 shows a method of comparing the changes with time of the ultrasonic impedance value Z relative to the tentative peak value by the peak judging section 57 in the detection allowing state. As shown in FIG. 33, in this embodiment at the time of comparing the changes with time of the ultrasonic impedance value Z relative to the tentative peak value, first, whether the high-frequency impedance value Z' at the detected gradual decrease start point of the ultrasonic impedance value Z is equal to or higher than a threshold value Z'th is judged (a step S181).

In this embodiment, based on the judgment in the step S181, a reference time ΔT during which the changes with time of the ultrasonic impedance value Z are compared with the tentative peak value is set. That is, a length of the reference time ΔT changes in accordance with the changes with time of the high-frequency impedance value Z' in addition to the changes with time of the ultrasonic impedance value Z. Since the length of the reference time ΔT changes in accordance with the changes with time of the high-frequency impedance value Z', a magnitude of a reference decrement s also changes in accordance with the changes with time of the high-frequency impedance value Z'. That is, in this embodiment, the length of the reference time ΔT and the magnitude of the reference decrement a are set based on the changes with time of the high-frequency impedance value Z' in addition to the changes with time of the ultrasonic impedance value Z.

When the high-frequency impedance value Z' at the gradual decrease start point of the ultrasonic impedance value Z is the threshold value Z'th or more (the step S181—Yes), the reference time ΔT is set in a first time range (a step S182). On the other hand, when the high-frequency impedance value Z' at the gradual decrease start point of the ultrasonic impedance value Z is smaller than the threshold value Z'th (the step S181—No), the reference time ΔT is set in a second time range longer than the first time range (a step S183). That is, the peak judging section 57 sets the length of the reference time ΔT based on whether the high-frequency impedance value Z' at the gradual decrease start point of the ultrasonic impedance value Z is the threshold value Z'th or more. Additionally, the reference time ΔT when the high-frequency impedance value Z' is smaller than the threshold value Z'th is set to be longer than the reference time ΔT when the high-frequency impedance value Z' is the threshold value Z'th or more.

When the reference time ΔT is set in the step S182 or the step S183, comparison is performed to judge whether the ultrasonic impedance value Z has continuously become smaller than a tentative peak value during the reference time ΔT after the gradual decrease start point in a step S122 like the first embodiment. Further, in a step S123, the reference decrement ϵ of the ultrasonic impedance value Z is set. At this time, the reference decrement ϵ is set in accordance with the length of the reference time ΔT. Furthermore, in a step S124, comparison is performed to judge whether a decrement ϵreal of the ultrasonic impedance value Z from the tentative peak value during elapse of the reference time ΔT from the gradual decrease start point is the reference decrement ϵ or more. Based on the comparisons in the step S122 and the step S124, a judgment parameter Zflag is set to 1 (a step S125), or the judgment parameter Zflag is set to 0 (a step S126). Moreover, like the first embodiment, in the step S114 in FIG. 11, whether the tentative peak value is the target peak caused due to the cut-and-divided of the treated target H is judged.

Each of FIG. 34 and FIG. 35 shows an example of changes with time of the ultrasonic impedance value Z and changes with time of the high-frequency impedance value Z' from an output start of the vibration generating electric power P and output of the high-frequency electric power P' from the electric power source 26. In each of FIG. 34 and FIG. 35, an axis of ordinate represents the ultrasonic impedance value Z and the high-frequency impedance value Z', and an axis of abscissa represents an elapsed time t from the output start of the vibration generating electric power P (the output start of the high-frequency electric power P'). Further, in each of FIG. 34 and FIG. 35, a solid line indicates the ultrasonic impedance value Z, and an alternate long and short dash line indicates the high-frequency impedance value Z'. FIG. 34 shows an example when a degree of wettability (wet properties) of the treated target H is low, i.e., the treated target H is not wet, and FIG. 35 shows an example when a degree of wettability of the treated target H is high.

In the example shown in FIG. 34, an elapsed time t15 is detected as a gradual decrease start point of the ultrasonic impedance value Z in a step S111, and an ultrasonic impedance value Z15 at the elapsed time t15 is held as a tentative peak value in a step S112. As described in the first embodiment, when the treated target H is not wet, a peak or the like of the ultrasonic impedance value Z due to contact of a contact portion 45 with the treated target H is not produced before the target peak caused by the cut-and-divided. Actually, the ultrasonic impedance value Z15 held as the tentative peak value is the target peak caused by the cut-and-divided.

When the degree of wettability of the treated target H is low, the high-frequency current I' is hard to flow through the treated target H held between the treatment section 17 and the jaw 18. Thus, the high-frequency impedance value Z' is high. Actually, in the example shown in FIG. 34, the high-frequency impedance value Z'15 is the threshold value Z'th or more at the gradual decrease start point t15 of the ultrasonic impedance value Z. Therefore, in the example shown in FIG. 34, in the step S182, the reference time ΔT is set to ΔT15 in the first time range, and the set reference time ΔT15 is short.

When the short reference time ΔT15 is set, whether the tentative peak value Z15 has been the target peak after the gradual decrease start point t15 is rapidly judged. Thus, after a target peak point (e.g., t15) when the ultrasonic impedance value Z becomes the target peak (e.g., Z15), the target peak (e.g., Z15) is rapidly detected. That is, in this embodiment, using the changes with time of the high-frequency impedance value Z' in detection of the target peak enables rapidly detecting the target peak (e.g., Z15) after the target peak time (e.g., t15) when the degree of wettability (wet properties) of the treated target H is low.

On the other hand, in the example shown in FIG. 35, an elapsed time t16 is detected as a gradual decrease start point of the ultrasonic impedance value Z in the step S111, and an ultrasonic impedance value Z16 at the elapsed time t16 is held as the tentative peak value in the step S112. As described above in the first embodiment, when the degree of wettability of the treated target H is high, a peak of the ultrasonic impedance value Z due to contact of the contact portion 45 with the treated target H is produced before the target peak caused by the cut-and-divided. Actually, the ultrasonic impedance value Z16 held as the tentative peak value is not the target peak caused due to the cut-and-divided but the peak caused due to the contact of the contact portion 45 with the treated target H.

When the degree of wettability of the treated target H is high, the high-frequency current I' is easy to flow through the treated target H grasped between the treatment section 17 and the jaw 18. Thus, the high-frequency impedance value Z' decreases. Actually, in the example shown in FIG. 35, at a gradual decrease start point t16 of the ultrasonic impedance value Z, the high-frequency impedance value Z'16 becomes smaller than the threshold value Z'th. Therefore, in the example shown in FIG. 35, in the step S183, the reference time ΔT is set to ΔT16 in the second time range, and the set reference time ΔT16 is long.

When the long reference time ΔT16 is set, in the step S111, an elapsed time t17 is detected as a gradual decrease restart point before the reference time ΔT16 from the gradual decrease start point t16 passes. Furthermore, in the step S112, the held tentative peak value Z16 is updated to an ultrasonic impedance value Z17 at the elapsed time (the gradual decrease restart point) t17, and the updated tentative peak value Z17 is held. That is, when the reference time ΔT is set to be long, a peak (e.g., Z16) caused due to contact of the contact portion 45 with the treated target H is readily judged not to be a target peak, even if the peak (e.g., Z16) caused due to the contact of the contact portion 45 with the treated target H is produced before the target peak (e.g., Z17). That is, in this modification, using changes with time of the high-frequency impedance value Z' in detection of the target peak enables readily judging that a peak (e.g., Z16) different from the target peak (e.g., Z17) is not the target peak (e.g., Z17), especially when the degree of wettability (wet properties) of the treated target H is high.

Modification of Third Embodiment

It is to be noted that the configuration using changes with time of the high-frequency impedance value Z' according to the third embodiment can be applied to all of the first modification, the second embodiment, the second modification, and the third modification. Moreover, the high-frequency electric power P' supplied to the treatment section 17 and the jaw 18 may be used for a treatment. In this case, when the high-frequency current I' flows through the grasped treated target H, the treated target (a biological tissue) H is denatured, and coagulation of the treated target H is promoted.

(Other Modifications)

A sixth modification that is a modification of the foregoing embodiments or the like will now be described with reference to FIG. 36 and FIG. 37. FIG. 36 is a view showing the treatment section 17 and the jaw 18 according to this modification. As shown in FIG. 36, in this modification, the contact portion 45 of the pad member 43 of the jaw 18 includes a first contact surface 91 and a second contact surface 92. The first contact surface 91 is made of, e.g., PTFE (polytetrafluoroethylene). The second contact surface 92 is made of a material harder than the first contact surface 91, and made of, e.g., PI (polyimide). In this modification, the second contact surface 92 is provided in a substantially central region of the jaw 18 in the longitudinal direction. Additionally, the first contact surface 91 is provided on each of both sides (the distal side and the proximal side) of the second contact surface 92 in the longitudinal direction of the jaw 18.

FIG. 37 shows an example of changes with time of the ultrasonic impedance value Z from an output start of the vibration generating electric power P from the electric power source 26. In FIG. 37, an axis of ordinate represents the ultrasonic impedance value Z, and an axis of abscissa represents an elapsed time t from the output start of the vibration generating electric power P. Further, in FIG. 37, a solid line indicates an example when the contact portion 45 is made of PTFE alone over the entire length in the longitudinal direction like the foregoing embodiments and the like, and an alternate long and short dash line indicates an example when the contact portion 45 includes the first contact surface 91 and the second contact surface 92 like this modification.

As shown in FIG. 37, in the example where the contact portion 45 is made of PTFE alone over the entire length in the longitudinal direction, an ultrasonic impedance value Z18 at an elapsed time t18 becomes a target peak. On the other hand, in the example where the contact portion 45 includes the first contact surface 91 and the second contact surface 92, an ultrasonic impedance value Z19 at an elapsed time t19 becomes a target peak, and the ultrasonic impedance value Z at the target peak is high. In this modification, providing the second contact surface 92 made of the hard material to a part of the contact portion 45 raises a time-dependent increase rate of the ultrasonic impedance value Z up to the target peak caused due to the cut-and-divided, thereby increasing the ultrasonic impedance value Z at the target peak. That is, in the changes with time of the ultrasonic impedance value Z, the target peak is prominently shown. Consequently, a detection accuracy of the target peak of the ultrasonic impedance value Z can be improved.

Furthermore, in the foregoing embodiments and others, the notifying section 59 is a lamp, a buzzer, or the like provided in the control unit 3, but it is not restricted thereto. For example, in a given modification, the notifying section 59 may be provided in a display section (not shown) of an endoscope system (not shown) used together with the ultrasonic treatment apparatus 1. In this case, when the target peak is detected, an index indicating that the target peak has been detected is shown in the display section.

Moreover, in the foregoing embodiments and others, the switching operation section 58 is provided in the control unit 3, but it is not restricted thereto. For example, in a given modification, the switching operation section 58 to which a switching operation between the detection allowing state and the detection disallowing state is input may be provided to the handle unit 6 of the ultrasonic treatment instrument 2.

In the foregoing embodiments and modifications, the ultrasonic treatment apparatus (1) includes the impedance detecting section (52) configured to detect the ultrasonic impedance value (Z) of the vibration generating electric power (P) with time in a state where the vibration generating electric power (P) is output from the electric power source (26), and the gradual decrease detecting section (55) configured to detect the gradual decrease start point at which the ultrasonic impedance value (Z) starts to gradually decrease based on a detection result of the impedance detecting section (52). Additionally, the ultrasonic treatment apparatus (1) includes the tentative peak value holding section (56) configured to hold the ultrasonic impedance value (Z) at the detected gradual decrease start point as a tentative peak value, and the peak judging section (57) configured to judge whether the held tentative peak value is a target peak which is a detection target by comparing changes with time of the ultrasonic impedance value (Z) after the gradual decrease start point relative to the held tentative peak value.

REFERENCE EXAMPLE

Figure 38:
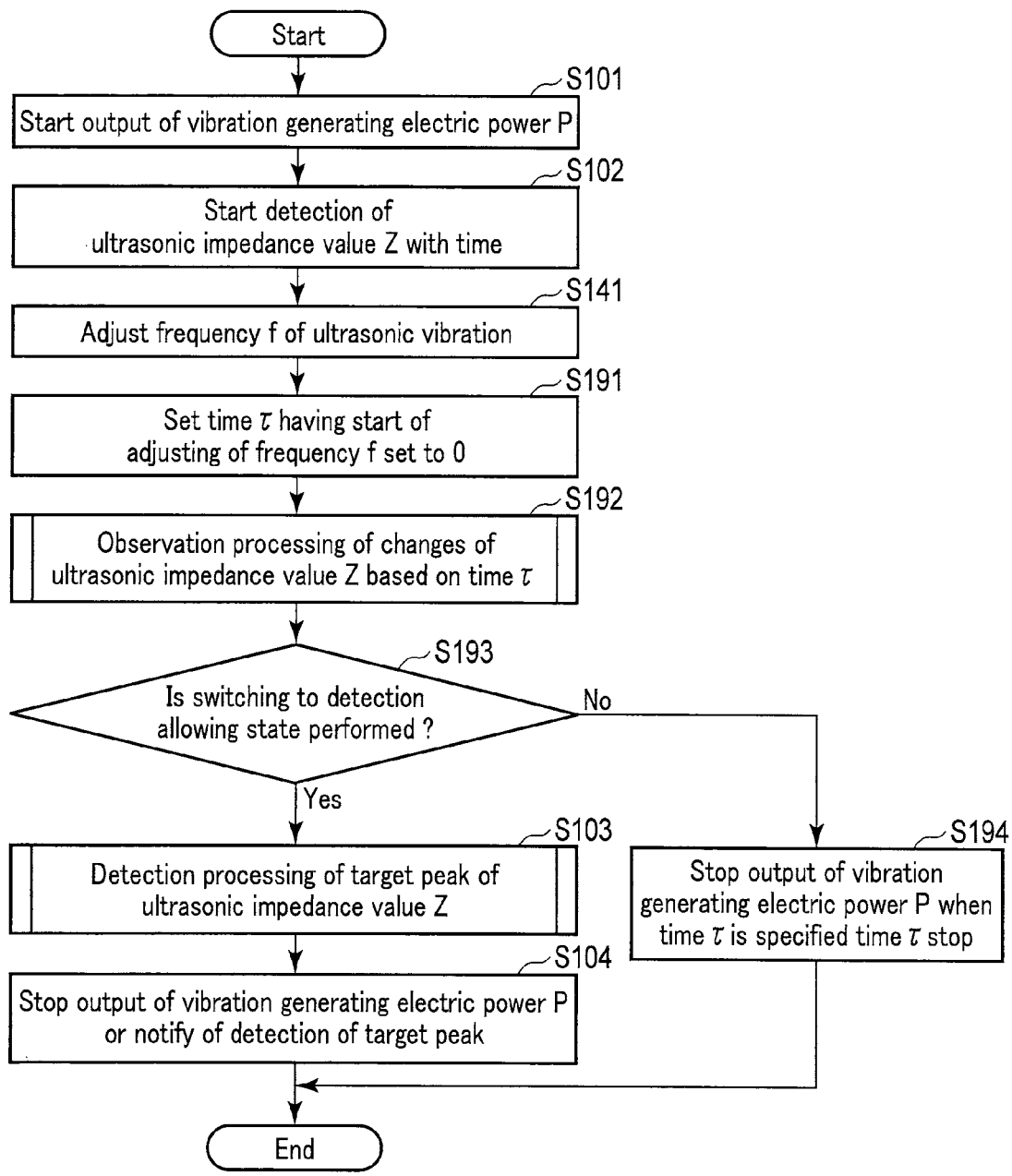
FIG. 38 is a flowchart showing an actuating state of a control unit from an output start of a vibration generating electric power according to a first reference example.

A reference example concerning the foregoing embodiments or the like will now be described. A first reference example will be first described in conjunction with FIG. 38 to FIG. 40. FIG. 38 is a view showing an actuating state of the control unit from an output start of the vibration generating electric power P. As shown in FIG. 38, in this reference example, like the second embodiment, when the vibration generating electric power P is output (a step S101), detection of the ultrasonic impedance value Z with time is started (a step S102), and a frequency f of the ultrasonic vibration is adjusted by the frequency adjusting section 63 (a step S141). However, in this reference example, there is set a time τ where an adjustment start (an adjustment start point) of the frequency f is 0 (a step S191). Further, observation processing of changes of the ultrasonic impedance value Z based on the time τ is executed (a step S192). Furthermore, the control section 51 judges whether the detection disallowing state is switched to the detection allowing state based on an observation result of the step S192 (a step S193).

Figure 39:
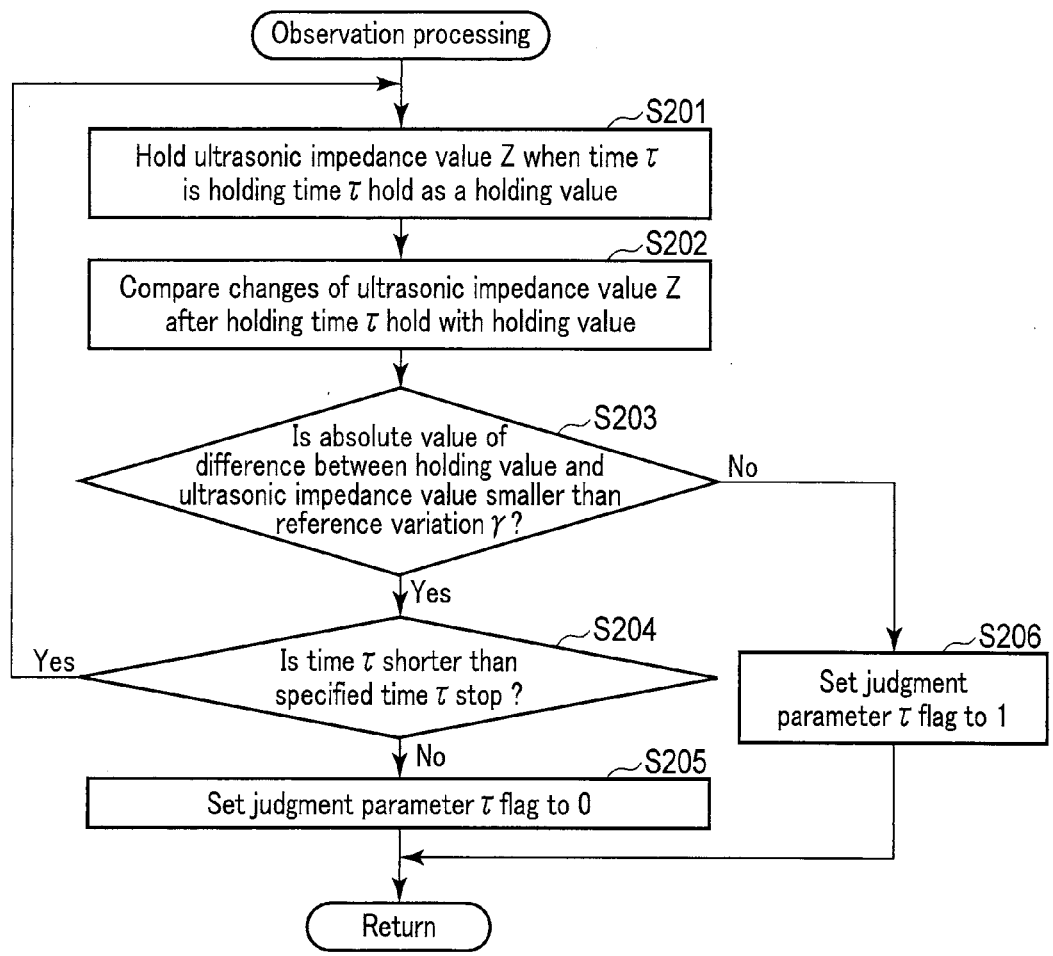
FIG. 39 is a flowchart showing observation processing of changes of an ultrasonic impedance value executed by the control section and others according to the first reference example based on a time where an adjustment start of a frequency is zero.
Figure 40:
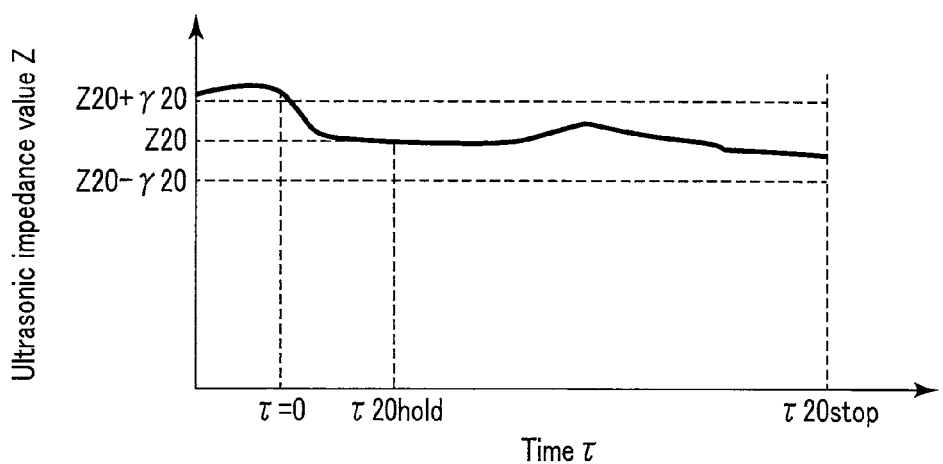
FIG. 40 is a schematic view showing an example of changes with time of the ultrasonic impedance value from an output start of the vibration generating electric power from an electric power source according to the first reference example.

FIG. 39 is a view showing the observation processing (the step S192 of FIG. 38) of changes of the ultrasonic impedance value Z performed by the control section 51 or the like based on the time τ where the adjustment start of the frequency f is zero. That is, FIG. 39 shows a method of observing changes of the ultrasonic impedance value Z based on the time τ. Furthermore, FIG. 40 is a view showing an example of changes of the ultrasonic impedance value Z. In FIG. 40, an axis of ordinate represents the ultrasonic impedance value Z, and an axis of abscissa represents the time τ where the adjustment start of the frequency is 0.

As shown in FIG. 40, for example, when an amplitude of the ultrasonic vibration is large, the ultrasonic impedance value Z hardly changes from an adjustment start of the frequency f in a treatment according to circumstances. In this case, even though the treated target is cut-and-divided, a target peak of the ultrasonic impedance value Z caused due to the cut-and-divided is not produced. Furthermore, before the cut-and-divided of the treated target, a minimal value of the ultrasonic impedance value Z is not produced either. Thus, in a configuration where output of the vibration generating electric power P is stopped based on detection of the target peak, when the ultrasonic impedance value Z changes like the example shown in FIG. 40, the vibration generating electric power P is output even after the cut-and-divided of the treated target. That is, since the target peak due to the cutoff is not produced even though the treated target is cut-and-divided, the treatment section 17 vibrates in a state where the contact portion 45 is in contact with the treatment section 17 after the cut-and-divided (after the target peak time point).

Thus, in this reference example, the observation processing of the ultrasonic impedance value Z based on the time τ is executed in the step S192. As shown in FIG. 39, in the observation processing of the ultrasonic impedance value Z based on the time τ (the step S192), the ultrasonic impedance value Z when the time τ is a holding time τhold is held as a holding value (a step S201). Here, the holding time τhold is a time point, e.g., when the 100 ms (milliseconds) passed from the adjustment start of the frequency f (τ=0). In the example shown in FIG. 40, an ultrasonic impedance value Z20 at a holding time τ20hold is held as a holding value. Moreover, changes of the ultrasonic impedance value Z after the holding time τhold are compared with the holding value (a step S202).

As a result of the comparison in the step S202, whether an absolute value of a difference between the holding value and the ultrasonic impedance value Z is smaller than a reference variation γ is judged (a step S203). That is, when the holding value is Zhold, whether Expression (3) is achieved is judged.

[Expression 3]

$$|Z-Zhold|<\gamma \quad (3)$$

When the absolute value of the difference between the holding value and the ultrasonic impedance value Z is smaller than the reference variation γ (the step S203—Yes), whether the time τ is smaller than a specified time τstop is judged (a step S204). That is, whether the specified time τstop has passed from the adjustment start of the frequency f is judged. Here, the specified time Tstop is, e.g., approximately 0 to 5 s (seconds). When the time τ is shorter than the specified time τstop (the step S204—Yes), the processing returns to the step S201, and the steps S201 to S203 are performed again. Here, judgment parameter τflag for use in a judgment of the step S193 in FIG. 38 is set. When the time τ is longer than the specified time τstop (the step S204—No), the judgment parameter τflag is set to 0 (a step S205).

Additionally, when the absolute value of the difference between the holding value and the ultrasonic impedance value Z is the reference variation γ or more (the step S203—No), the judgment parameter τflag is set to 1 (a step S206). In the example shown in FIG. 40, an absolute value of a difference between a holding value Z20 and the ultrasonic impedance value Z is always smaller than a reference variation γ20 between a holding time τ20hold and a specified time τ20stop. That is, the ultrasonic impedance value Z does not become (Z20+γ20) or more, and does not become (Z20−γ20) or less either. Here, (Z20+γ20) is, 0 to 200Ω, and approximately 100Ω is preferred. Thus, in the example shown in FIG. 40, the judgment parameter τflag is set to 0. In a step S193, a judgment is made based on the judgment parameter τflag.

When the judgment parameter τflag is 1, the detection disallowing state is judged to be switched to the detection allowing state (the step S193—Yes). When the state is switched to the detection allowing state, like the second embodiment, the detection processing of the target peak is performed (a step S103). Further, when the target peak is detected, output of the vibration generating electric power P is stopped, or detection of the target peak is notified (a step S104). On the other hand, when the judgment parameter τflag is 0, the state is judged not to be switched to the detection allowing state (the step S193—No), and the detection disallowing state is maintained. Furthermore, when the time τ reaches the specified time tstop, output of the vibration generating electric power P is stopped (a step S194).

As described above, in this reference example, even if switching to the detection allowing state is not performed and the target peak is not detected, output of the vibration generating electric power P is stopped at the specified time τstop. Thus even if the target peak is not detected (e.g., the example of FIG. 40), wear of the contact portion 45 of the jaw 18 caused due to the ultrasonic vibration is effectively prevented.

Figure 41:
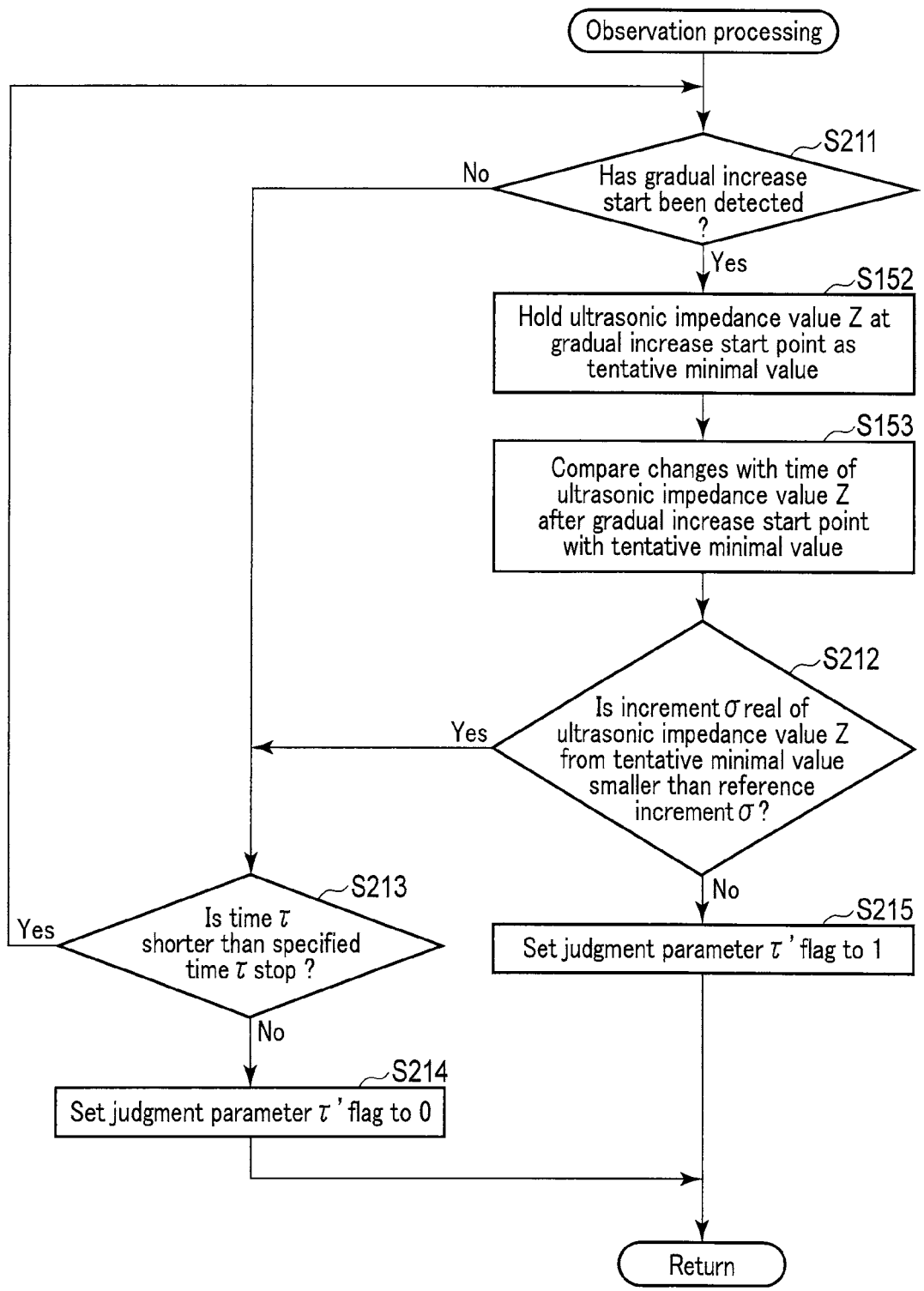
FIG. 41 is a flowchart showing observation processing of changes of an ultrasonic impedance value executed by a control section and a minimal value detecting section according to a second reference example based on a time where an adjustment start of a frequency is zero.

It is to be noted that, as shown in FIG. 41 to FIG. 43 as a second reference example, in the observation processing of the ultrasonic impedance value Z based on the time τ (the step S192 in FIG. 38), processing different from that of the first reference example may be executed. FIG. 41 is a view showing the observation processing (the step S192 in FIG. 38) of changes of the ultrasonic impedance value Z performed by the control section 51 and the minimal value detecting section 65 based on the time τ where the adjustment start of the frequency f is zero. Furthermore, FIG. 42 is a view showing an example of changes of the ultrasonic impedance value Z, and FIG. 43 is a view showing an example of changes of the ultrasonic impedance value Z which is different from FIG. 42. In each of FIG. 42 and FIG. 43, an axis of ordinate represents the ultrasonic impedance value Z, and an axis of abscissa represents the time τ where the adjustment start of the frequency f (the adjustment start point) is 0.

As shown in FIG. 42, in a treatment, the ultrasonic impedance value continuously gradually decreases from the adjustment start of the frequency f and does not restart the gradual increase according to circumstances. Moreover, as shown in FIG. 43, even though the ultrasonic impedance value Z gradually decreases from the adjustment start of the frequency f and then restarts the gradual increase, an increment areal based on the gradual increase is smaller than the reference increment σ and a minimal value is not detected by the minimal value detecting section 65 according to circumstances. The above-described change of the ultrasonic impedance value Z occurs in, e.g., a situation where the treated target is placed only between the distal portion of the treatment section 17 and the distal portion of the jaw 18 and no treated target is present between the proximal portion of the treatment section 17 and the proximal portion of the jaw 18. In this case, like the first reference example, even if the treated target is cut-and-divided, the target peak is not produced in the ultrasonic impedance value Z due to the cut-and-divided. Additionally, before the treated target is cut off, a minimal value is not produced in the ultrasonic impedance value Z either.

Thus, in this reference example, in the step S192 in FIG. 38, the ultrasonic impedance value Z is observed based on the time τ as follows. As shown in FIG. 41, after the adjustment start of the frequency f, whether a start of the gradual increase of the ultrasonic impedance value Z has been detected is judged (a step S211). When the gradual increase has been started (the step S211—Yes), the ultrasonic impedance value Z at the start of the gradual increase is held as a tentative minimal value (a step S152). Further, changes with time of the ultrasonic impedance value Z after the gradual increase start point are compared with the tentative minimal value (a step S153). The steps S152 and S153 are carried out in the same manner as the second embodiment.

Whether an increment σreal of the ultrasonic impedance value from the tentative minimal value is smaller than the reference increment σ is judged based on a result of the comparison of the step S153 (a step S212). When the start of the gradual increase is not detected (the step S211—No), and when the increment areal based on the gradual increase is smaller than the reference increment σ (the step S212—Yes), whether the time τ is shorter than the specified time τstop is judged (a step S213). That is, whether the specified time τstop has elapsed from the adjustment start of the frequency f is judged. Here, the specified time τstop is, e.g., approximately 0 to 5 s (seconds). When the time τ is shorter than the specified time τstop (the step S213—Yes), the processing returns to the step S211, and the step S211 alone is performed again, or the steps S211, S152, S153, and S212 are sequentially carried out. Here, a judgment parameter τ'flag for use in the judgment of the step S193 in FIG. 38 is set. When the time τ is longer than the specified time τstop (the step S213—No), the judgment parameter τ'flag is set to 0 (a step S214).

Moreover, when the increment of the ultrasonic impedance value Z from the tentative minimal value is the reference increment σ or more (the step S212—Yes), the judgment parameter τ'flag is set to 1 (a step S215). In the example shown in FIG. 42, the ultrasonic impedance value continuously gradually decreases during a specified time τ21stop from the adjustment start of the frequency f (τ=0). That is, in the step S211, no gradual increase is detected. Thus, in the example shown in FIG. 42, the judgment parameter τ'flag is set to 0.

Additionally, in the example shown in FIG. 43, after the adjustment start of the frequency f (τ=0), the ultrasonic impedance value temporarily gradually increases, but an increment σ22real is smaller than a reference increment σ22. That is, an ultrasonic impedance value Z22 is held as a tentative minimal value in the step S152, but in the step S212, the increment σ22real of the ultrasonic impedance value Z from the tentative minimal value Z22 is judged to be smaller than the reference increment σ22. Here, the reference increment σ22 is, e.g., 0 to 200Ω, and approximately 50Ω, is preferred. Thus, in the example shown in FIG. 43, the judgment parameter τ'flag is set to 0. In the step S193, the judgment is made based on the judgment parameter τ'flag.

When the judgment parameter τ'flag is 1, the detection disallowing state is judged to be switched to the detection allowing state (the step S193—Yes). On the other hand, when the judgment parameter τ'flag is 0, switching to the detection allowing state is not performed (the step S193—No), and the detection disallowing state is held. Further, when the time τ has reached the specified time τstop, output of the vibration generating electric power P is stopped (the step S194). In this reference example, even if the ultrasonic impedance value changes like the example shown in FIG. 42 or the example shown in FIG. 43, output of the vibration generating electric power P is stopped at the specified time τstop, and wear of the contact portion 45 of the jaw 18 caused due to the ultrasonic vibration is effectively prevented.

It is to be noted that, in the step S192 in FIG. 38, both the processing described in the first reference example and the processing described in the second reference example may be carried out. In this case, only when τflag is 1 and τ'flag is 1, the detection disallowing state is judged to be switched to the detection allowing state in the step S193.

Furthermore, a third reference example will now be described with reference to FIG. 44 to FIG. 47. FIG. 44 is a view showing an actuating state of the control unit from an output start of the vibration generating electric power P in this reference example. As shown in FIG. 44, in this reference example, like the second embodiment, when the vibration generating electric power P is output (a step S101), detection of the ultrasonic impedance value Z with time is started (a step S102), and the frequency adjusting section 63 adjusts the frequency f of the ultrasonic vibration (a step S141). Moreover, the minimal value detecting section 65 executes detection processing of a minimal value of the ultrasonic impedance value Z (a step S142), and the detection disallowing state is switched to the detection allowing state (a step S143). However, in this reference example, there is set a time Y where a point of switching to the detection allowing state is 0 (a step S221). Additionally, observation processing of changes of the ultrasonic impedance value Z based on the time Y is carried out (a step S222). Further, the control section 51 judges whether a target peak has been detected based on an observation result of the step S222 (a step S223).

FIG. 45 is a view showing the observation processing of changes of the ultrasonic impedance value Z based on the time Y defining the point to switch to the detection allowing state as zero which is executed by the control section 51 and the peak detecting section 53 (a step S222 in FIG. 44). That is, FIG. 45 shows a method of observing changes of the ultrasonic impedance value Z based on the time Y. Furthermore, FIG. 46 is a view showing an example of changes of the ultrasonic impedance value Z, and FIG. 47 is a view showing an example of changes of the ultrasonic impedance value Z different from FIG. 46. In each of FIG. 46 and FIG. 47, an axis of ordinate represents the ultrasonic impedance value Z, and an axis of abscissa represents the time Y using the point to switch to the detection allowing state as 0.

As shown in FIG. 46, in a treatment, after switching to the detection allowing state, the ultrasonic impedance value Z continuously gradually increases and does not start to gradually decrease according to circumstances. Moreover, as shown in FIG. 47, even if the gradual decrease is started after switching to the detection allowing state, the ultrasonic impedance value Z hardly decreases from a start of the gradual decrease, and the peak detecting section 53 does not detect a target peak according to circumstances. In this case, even if the treated target is cut-and-divided, no target peak is produced in the ultrasonic impedance value Z by the cut-and-divided.

Thus, in this reference example, in the step s222 in FIG. 44, the observation processing of the ultrasonic impedance value Z based on the time Y is carried out as follows. As shown in FIG. 45, in the step S222, first, whether the start of the gradual decrease of the ultrasonic impedance value Z has been detected after switching to the detection allowing state is judged (a step S231). When the gradual decrease has been started (the step S231—Yes), the ultrasonic impedance value Z at the gradual decrease start point is held as a tentative peak value (a step S112). Additionally, comparison processing of changes with time of the ultrasonic impedance value Z after the gradual decrease start point relative to the tentative peak value is performed (a step S113). Further, whether the tentative peak value is a target peak is judged based on a result of the comparison in the step S113 (a step S114). The steps S112 to S114 are performed in the same manner as the first embodiment. It is to be noted that the comparison processing of changes with time of the ultrasonic impedance value Z relative to the tentative peak value (the step S113) may be carried out in the same manner as the first embodiment (see FIG. 12), or may be carried out in the same manner as the first modification (see FIG. 15).

When the tentative peak value is judged not to be the target peak (the step S114—No), the processing returns to the step S231, and the step S231 alone is performed again, or the steps S231, S112, S113, and S114 are sequentially performed. When the start of the gradual decrease is not detected (the step S231—No), and when the tentative peak value is judged not to be the target peak (the step S114—No) and then the gradual decrease is not detected (the step S231—No), whether the time Y is shorter than a specified time Ystop is judged (a step S232). That is, whether the specified time Ystop has elapsed from the point to switch to the detection allowing state is judged. When the time Y is shorter than the specified time Ystop (the step S232—Yes), the processing returns to the step S231, and the step S231 alone is performed again, or the steps S231, S112, S113, and S114 are sequentially performed. Here, a judgment parameter Yflag for use in the judgment in the step S223 of FIG. 44 is set. When the time Y is longer than the specified time Ystop (the step S232—No), the judgment parameter Yflag is set to 0 (a step S233).

Further, when the tentative peak value held in the step S112 is judged to be the target peak (the step S114—Yes), the judgment parameter Yflag is set to 1 (a step S234). In the example shown in FIG. 46, the ultrasonic impedance value continuously gradually increases during a specified time Y23stop from the point to switch to the detection allowing state (Y=0). That is, in the step S231, the gradual decrease is not detected. Thus, in the example shown in FIG. 46, the judgment parameter Yflag is set to 0.

Furthermore, in the example shown in FIG. 47, after the point to switch to the detection allowing state (Y=0), the ultrasonic impedance value temporarily gradually decreases, but a decrement ϵ24real during a reference time ΔY24 from a gradual decrease start point Y24 is smaller than a reference decrement ϵ24. That is, although the ultrasonic impedance value Z24 is held as a tentative peak value in the step S112, the tentative peak value Z24 is determined not to be a target peak in the step S114. Further, after the gradual decrease start point Y24, the ultrasonic impedance value Z does not restart to gradually decrease. Thus, after the tentative peak value Z24 is judged not to be the target peak in the step S114, the gradual decrease is not detected again in a step S231. Thus, in the example shown in FIG. 47, the judgment parameter Yflag is set to 0. In the step S223, a judgment is made based on the judgment parameter Yflag. It is to be noted that, in the example shown in FIG. 47, after the gradual decrease start point Y24, the tentative peak value Z24 is not updated, and the tentative peak value Z24 is continuously held.

When the judgment parameter Yflag is 1, the target peak is judged to have been detected (the step S223—Yes). When the target peak has been detected, like the first embodiment, output of the vibration generating electric power P is stopped, or detection of the target peak is notified (a step S104). On the other hand, when the judgment parameter Yflag is 0, the target peak is judged not to have been detected (the step S223—No). Furthermore, when the time Y reaches the specified time Ystop, output of the vibration generating electric power P is stopped (a step S224). As described above, in this reference example, even if the ultrasonic impedance value changes like the example in FIG. 46 or the example in FIG. 47, output of the vibration generating electric power P is stopped at the specified time Ystop, thereby effectively avoiding wear of the contact portion 45 of the jaw 18 caused due to the ultrasonic vibration.

Hereinafter, characteristic matters will be added.

Statement (Added Statement 1)

A control unit provided in an ultrasonic treatment apparatus, the ultrasonic treatment apparatus including a vibration generating section which is configured to generate an ultrasonic vibration by supplying a vibration generating electric power, a treatment section to which the ultrasonic vibration generated in the vibration generating section is transmitted and which is configured to perform a treatment by use of the transmitted ultrasonic vibration, and a jaw which is openable and closable relative to the treatment section and which includes a contact portion contactable with the treatment section in a state where the jaw is closed relative to the treatment section, the control unit being configured to control a supply of the vibration generating electric power to the vibration generating section, the control unit comprising:

an electric power source which is configured to output the vibration generating electric power;

an impedance detecting section which is configured to detect an ultrasonic impedance value of the vibration generating electric power with time in a state where the vibration generating electric power is output from the electric power source;

a gradual decrease detecting section which is configured to detect a gradual decrease start point to start gradual decrease of the ultrasonic impedance value on the basis of a detection result in the impedance detecting section;

a tentative peak value holding section which is configured to hold the ultrasonic impedance value at the detected gradual decrease start point as a tentative peak value; and a peak judging section which is configured to judge whether the held tentative peak value is a target peak of a detection target by comparing, relative to the held tentative peak value, changes with time of the ultrasonic impedance value after the gradual decrease start point.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment apparatus comprising:

an electric power source which is configured to output vibration generating electric power;

a vibration generating section which is configured to generate an ultrasonic vibration by supplying the vibration generating electric power from the electric power source;

a treatment section to which the ultrasonic vibration generated in the vibration generating section is transmitted, and which is configured to perform a treatment by use of the transmitted ultrasonic vibration;

a jaw which is openable and closable relative to the treatment section, and which includes a contact portion contactable with the treatment section in a state where the jaw is closed relative to the treatment section;

an impedance detecting section which is configured to detect an ultrasonic impedance value of the vibration generating electric power with time, in a state where the vibration generating electric power is output from the electric power source;

a gradual decrease detecting section which is configured to detect a gradual decrease start point to start gradual decrease of the ultrasonic impedance value on the basis of a detection result in the impedance detecting section;

a tentative peak value holding section which is configured to hold the ultrasonic impedance value at the detected gradual decrease start point as a tentative peak value; and a peak judging section which is configured to judges whether the held tentative peak value is a target peak of a detection target by comparing, relative to the held tentative peak value, changes with time of the ultrasonic impedance value after the gradual decrease start point.

2. The ultrasonic treatment apparatus according to claim 1, wherein the peak judging section is configured to judge whether the tentative peak value is the target peak based on whether the ultrasonic impedance value is continuously smaller than the tentative peak value after the gradual decrease start point.

3. The ultrasonic treatment apparatus according to claim 1, wherein the peak judging section is configured to judge that the tentative peak value at the gradual decrease start point is not the target peak, when the ultrasonic impedance value becomes the tentative peak value or more after the gradual decrease start point.

4. The ultrasonic treatment apparatus according to claim 1,
wherein the gradual decrease detecting section is configured to detect a gradual decrease restart point at which gradual decrease begins again, when the ultrasonic impedance value restarts to gradually decrease after the ultrasonic impedance value has become the tentative peak value or more,
the tentative peak value holding section is configured to update the held tentative peak value to the ultrasonic impedance value detected at the gradual decrease restart point, and configured to hold the updated peak value, and
the peak judging section is configured to judge whether the updated tentative peak value is the target peak value by comparing changes with time of the ultrasonic impedance value after the gradual decrease restart point relative to the updated tentative peak value.

5. The ultrasonic treatment apparatus according to claim 1,
wherein the peak judging section is configured to judge whether the tentative peak is the target peak based on whether a decrement of the ultrasonic impedance value from the tentative peak value during elapse of a reference time from the gradual decrease start point is a reference decrement or more.

6. The ultrasonic treatment apparatus according to claim 5,
wherein the peak judging section is configured to set a length of the reference time and a magnitude of the reference decrement based on the ultrasonic impedance value at the gradual decrease start point which is the tentative peak value.

7. The ultrasonic treatment apparatus according to claim 5,
wherein the peak judging section is configured to set a length of the reference time and a magnitude of the reference decrement based on an average value of the ultrasonic impedance value during a period from an output start of the vibration generating electric power from the electric power source to the gradual decrease start point.

8. The ultrasonic treatment apparatus according to claim 5, further comprising:
an ultrasonic probe which includes the treatment section, is coupled with the vibration generating section, and configured to transmit the ultrasonic vibration generated in the vibration generating section toward the treatment section;
an information memory section in which at least information concerning a type of the ultrasonic probe is stored; and
an identifying section which is configured to identify the type of the ultrasonic probe coupled with the vibration generating section by reading the information stored in the information memory section,
wherein the peak judging section is configured to set a length of the reference time and a magnitude of the reference decrement based on an identification result in the identifying section.

9. The ultrasonic treatment apparatus according to claim 5, further comprising:
an information memory section in which at least information concerning a type of the vibration generating section is stored; and
an identifying section which is configured to identify the type of the vibration generating section, to which the vibration generating electric power is supplied from the electric power source, by reading the information stored in the information memory section,
wherein the peak judging section is configured to set a length of the reference time and a magnitude of the reference decrement based on an identification result in the identifying section.

10. The ultrasonic treatment apparatus according to claim 5,
wherein the impedance detecting section is configured to detect a magnitude of a vibration generating current output from the electric power source with time, and
the peak judging section is configured to set a length of the reference time and a magnitude of the reference decrement based on a detection result of the vibration generating current in the impedance detecting section.

11. The ultrasonic treatment apparatus according to claim 5, further comprising:
an information memory section in which at least the number of times of a heat sterilization processing executed in the vibration generating section is stored; and
a number-of-times updating section which is configured to update the number of times of execution of the heat sterilization processing stored in the information memory section, when the heat sterilization processing is executed in the vibration generating section,
wherein the peak judging section is configured to set a length of the reference time and a magnitude of the reference decrement based on the number of times of the execution of the heat sterilization processing stored in the information memory section.

12. The ultrasonic treatment apparatus according to claim 1, further comprising:
a gradual increase detecting section which is configured to detect a gradual increase start point at which gradual increase starts, when the ultrasonic impedance value starts to gradually increase after the gradual decrease start point,
wherein the peak judging section is configured to judge that the tentative peak value at the gradual decrease start point is not the target peak, when an increment of the ultrasonic impedance value from the gradual increase start point has become a reference increment or more.

13. The ultrasonic treatment apparatus according to claim 1, further comprising:
a control section which is configured to switch between a detection disallowing state where a detection of the target peak is not executed and a detection allowing state where the detection of the target peak is executed by controlling the gradual decrease detecting section, the tentative peak value holding section and the peak judging section.

14. The ultrasonic treatment apparatus according to claim 13, further comprising:
a frequency adjusting section which is configured to adjust a frequency of the ultrasonic vibration based on a relationship between the frequency of the ultrasonic vibration and the ultrasonic impedance value after an output start of the vibration generating electric power from the electric power source; and
a minimal value detecting section which is configured to detect a minimal value, at which the ultrasonic impedance value becomes minimal with time, based on a detection result in the impedance detecting section, wherein, when a time point at which the minimal value is first detected by the minimal value detecting section after an adjustment start of the frequency of the ultrasonic vibration by the frequency adjusting section is defined as a minimal detection point, the control section is configured to maintain the detection disallowing state until the minimal detection point by controlling the gradual decrease detecting section, the tentative peak value holding section and the peak judging section.

15. The ultrasonic treatment apparatus according to claim 14, wherein the minimal value detecting section includes:

a gradual increase detecting section which is configured to detect a gradual increase start point at which the ultrasonic impedance value starts to gradually increase based on a detection result in the impedance detecting section;

a tentative minimal value holding section which is configured to hold the ultrasonic impedance value at the detected gradual increase start point as a tentative minimal value; and a minimal value judging section which is configured to judge whether the tentative minimal value is the minimal value by comparing changes with time of the ultrasonic impedance value after the gradual increase start point relative to the held tentative minimal value.

16. The ultrasonic treatment apparatus according to claim 13, further comprising:

a frequency adjusting section which is configured to adjust a frequency of the ultrasonic vibration based on a relationship between the frequency of the ultrasonic vibration and the ultrasonic impedance value after an output start of the vibration generating electric power from the electric power source;

wherein, when a time point where a predetermined set time has passed from an adjustment start of the frequency of the ultrasonic vibration by the frequency adjusting section is defined as a startup point, the control section is configured to maintain the detection disallowing state until the startup point by controlling the gradual decrease detecting section, the tentative peak value holding section and the peak judging section.

17. The ultrasonic treatment apparatus according to claim 13, further comprising:

a frequency adjusting section which is configured to adjust a frequency of the ultrasonic vibration based on a relationship between the frequency of the ultrasonic vibration and the ultrasonic impedance value after an output start of the vibration generating electric power from the electric power source;

wherein the impedance detecting section is configured to detect the frequency of the ultrasonic vibration with time, and the control section is configured to maintain the detection disallowing state until the frequency of the ultrasonic vibration falls below a threshold value by controlling the gradual decrease detecting section, the tentative peak value holding section and the peak judging section after an adjustment start of the frequency of the ultrasonic vibration by the frequency adjusting section.

18. The ultrasonic treatment apparatus according to claim 13, further comprising:

an ultrasonic probe which includes the treatment section, is coupled with the vibration generating section, and configured to transmit the ultrasonic vibration generated in the vibration generating section toward the treatment section;

an information memory section in which at least information concerning a type of the ultrasonic probe is stored; and an identifying section which is configured to identify the type of the ultrasonic probe coupled with the vibration generating section by reading the information stored in the information memory section, wherein the control section is configured to set a parameter for use in a judgment of whether the detection disallowing state is switched to the detection allowing state based on an identification result in the identifying section.

19. The ultrasonic treatment apparatus according to claim 13, further comprising:

an information memory section in which at least information concerning a type of the vibration generating section is stored; and an identifying section which is configured to identify the type of the vibration generating section, to which the vibration generating electric power is supplied from the electric power source, by reading the information stored in the information memory section, wherein the control section is configured to set a parameter for use in a judgment of whether the detection disallowing state is switched to the detection allowing state based on an identification result in the identifying section.

20. The ultrasonic treatment apparatus according to claim 13, wherein the impedance detecting section is configured to detect a magnitude of a vibration generating current output from the electric power source with time, and the control section is configured to set a parameter for use in a judgment of whether the detection disallowing state is switched to the detection allowing state based on a detection result of the vibration generating current in the impedance detecting section.

21. The ultrasonic treatment apparatus according to claim 13, further comprising:

an information memory section in which at least the number of times of a heat sterilization processing executed in the vibration generating section is stored; and a number-of-times updating section which is configured to update the number of times of execution of the heat sterilization processing stored in the information memory section, when the heat sterilization processing is executed in the vibration generating section, wherein the control section is configured to set a parameter for use in a judgment of whether the detection disallowing state is switched to the detection allowing state based on the number of times of execution of the heat sterilization processing stored in the information memory section.

22. The ultrasonic treatment apparatus according to claim 13, further comprising:

a switching operation section to which a switching operation between the detection disallowing state and the detection allowing state is input, wherein the control section is configured to control the gradual decrease detecting section, the tentative peak value holding section and the peak judging section to the detection disallowing state or the detection allowing state based on the switching operation in the switching operation section.

23. The ultrasonic treatment apparatus according to claim 1, further comprising:
an ultrasonic probe which includes the treatment section, is coupled with the vibration generating section, and configured to transmit the ultrasonic vibration generated in the vibration generating section toward the treatment section;
an information memory section in which at least information concerning a type of the ultrasonic probe is stored; and
an identifying section which is configured to identify the type of the ultrasonic probe coupled with the vibration generating section by reading the information stored in the information memory section,
wherein the peak judging section is configured to set a parameter for use in a judgment of whether the tentative peak value is the target peak based on an identification result in the identifying section.

24. The ultrasonic treatment apparatus according to claim 1, further comprising:
an information memory section in which at least information concerning a type of the vibration generating section is stored; and
an identifying section which identifies the type of the vibration generating section, to which the vibration generating electric power is supplied from the electric power source, by reading the information stored in the information memory section,
wherein the peak judging section is configured to set a parameter for use in a judgment of whether the tentative peak value is the target peak based on an identification result in the identifying section.

25. The ultrasonic treatment apparatus according to claim 1,
wherein the impedance detecting section is configured to detect a magnitude of a vibration generating current output from the electric power source with time, and
the peak judging section is configured to set a parameter for use in a judgment of whether the tentative peak value is the target peak, based on a detection result of the vibration generating current in the impedance detecting section.

26. The ultrasonic treatment apparatus according to claim 1, further comprising:
an information memory section in which at least the number of times of the heat sterilization processing executed in the vibration generating section is stored; and
a number-of-times updating section which is configured to update the number of times of execution of the heat sterilization processing stored in the information memory section, when the heat sterilization processing is executed in the vibration generating section,
wherein the peak judging section is configured to set a parameter for use in a judgment of whether the tentative peak value is the target peak, based on the number of times of the execution of the heat sterilization processing stored in the information memory section.

27. The ultrasonic treatment apparatus according to claim 1,
wherein the treatment section and the jaw function as electrodes by supply of a high-frequency electric power,
the electric power source is configured to output the high-frequency electric power supplied to the treatment section and the jaw,
the impedance detecting section is configured to detect a high-frequency impedance value of the high-frequency electric power with time, in a state where the high-frequency electric power is output from the electric power source, and
the peak judging section is configured to judge whether the tentative peak value is the target peak, based on changes with time of the high-frequency impedance value in addition to the changes with time of the ultrasonic impedance value.

28. The ultrasonic treatment apparatus according to claim 27,
wherein the peak judging section is configured to judge whether the tentative peak is the target peak, based on whether a decrement of the ultrasonic impedance value from the tentative peak value during elapse of a reference time from the gradual decrease start point is a reference decrement or more, and
the peak judging section is configured to set a length of the reference time and a magnitude of the reference decrement, based on changes with time of the high-frequency impedance value.

29. The ultrasonic treatment apparatus according to claim 28,
wherein the peak judging section is configured to set the length of the reference time based on whether the high-frequency impedance value at the gradual decrease start point is a threshold value or more, and configured to set the reference time when the high-frequency impedance value is smaller than the threshold value longer than that when the high-frequency impedance value is the threshold value or more.

30. The ultrasonic treatment apparatus according to claim 1, further comprising:
a control section which is configured to stop or decrease output of the vibration generating electric power from the electric power source, when the peak judging section judges the tentative peak value at the gradual decrease start point to be the target peak.

\* \* \* \* \*